(12) United States Patent
Kwon et al.

(10) Patent No.: US 6,355,476 B1
(45) Date of Patent: *Mar. 12, 2002

(54) NUCLEIC ACID ENCODING MIP-1α LYMPHOKINE

(75) Inventors: Byoung Se Kwon, Carmel; Hal E. Broxmeyer, Indianapolis, both of IN (US)

(73) Assignee: Advanced Research and TechnologyInc, Indianapolis, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 82 days.

(21) Appl. No.: 07/922,996

(22) Filed: Jul. 30, 1992

Related U.S. Application Data

(63) Continuation-in-part of application No. 07/267,577, filed on Nov. 7, 1988, now abandoned.

(51) Int. Cl.$^7$ .......................... C07K 14/52; C12N 15/19
(52) U.S. Cl. .................. 435/320.1; 435/69.1; 536/23.1; 536/23.5; 530/300; 530/324
(58) Field of Search ................ 435/69.5, 91, 172.3, 435/320.1, 235.1, 69.1, 18, 29, 41, 56, 73; 536/27, 23.1, 23.5; 530/300, 350, 324

(56) References Cited

U.S. PATENT DOCUMENTS 5,817,763 A * 10/1998 Cerami et al.

OTHER PUBLICATIONS

Supps et al Proc Natl Acad Sci USA vol. 78 pp 6613–6617 (1981).*

Lewin Science vol. 237 p. 1570 (1987).*

Reeck et al Cell vol. 50 p. 667 (1987).*

Kwon et al Proc. Natl Acad Sci. USA vol. 86 pp 1963–1967 (1989).*

Brown et al T. Immunol. vol. 142 pp. 679–687 (1989).*

*Hematopoietic Growth Factors in Clinical Applications, Chapter 1,* Marcel Dekker, Inc., New York, NY, pp. 3–24, (1990).

Broxmeyer, H.E., "Suppressor Cytokines and Regulation of Myelopoiesis", *The American Journal of Pediatric Hematology/Oncology,* 14 (1), pp. 22–30, (1992).

Broxmeyer, H.E., et al., "Enhancing and Suppressing Effects of Recombinant Murine Macrophage Inflammatory Proteins on Colony Formation In Vitro by Bone Marrow Myeloid Progenitor Cells", *Blood,* 76 (6), pp. 1110–1116, (Sep. 15, 1990).

Broxmeyer, H.E., et al., "Macrophage Inflammatory Protein (MIP) –1β Abrogates the Capacity of MIP–1α to Suppress Myeloid Progenitor Cell Growth", *The Journal of Immunology,* 147 (8), pp. 2586–2594, (Oct. 15, 1991).

Broxmeyer, H.E., et al., "Myelopoietic Enhancing Effects of Murine Macrophage Inflammatory Proteins 1 and 2 on Colony Formation In Vitro by Murine and Human Bone Marrow Granulocyte/Macrophage Progenitor Cells", *Journal of Experimental Medicine,* 170, pp. 1583–1594, (Nov. 1989).

Fahey III, T.J., et al., "Cytokine Production in a Model of Wound Healing: The Appearance of MIP–1, MIP–2, Cachectin/TNF and IL–I", *Cytokine,* (22), pp. 92–99, (Mar. 1990).

Kwon, B.S., et al., "Expression Characteristics of Two Potential T Cell Mediator Genes", *Cellular Immunology,* 121, pp. 001–009, (1989).

Kwon, B.S., et al., "Isolation of initial characterization of multiple species of T–lymphocyte subset cDNA clones", *Proceedings of the National Academy of Sciences,* 84, pp. 2896–2900, (May 1987).

Miller, M. D., et al., "A Novel Polypeptide Secreted by Activated Human T Lymphocytes", *The Journal of Immunology,* 143 (9), pp. 2907–2916, (Nov. 1, 1989).

* cited by examiner

*Primary Examiner*—Claire M. Kaufman
(74) *Attorney, Agent, or Firm*—Schwegman, Lundberg, Woessner & Kluth, P.A.

(57) ABSTRACT

Full length cDNAs, L2G25B and 4-1BB, were isolated and sequenced. The cDNA L2G25B encodes for the lymphokine, macrophage inflammatory protein-1α or MIP-1α. The studies disclosed herein suggest that MIP-1α and MIP-β can, through rapid action, modulate early myeloid progenitor cell proliferation. Recombinant proteins have been produced for the cytokine, L2G25BP (Macrophage Inflammatory Protein-1α, MIP-1α). By employing the recombinant protein (rMIP-1α), receptors for MIP-1α were identified on Con A-stimulated and unstimulated CTLL-R8, a T-cell line, and LPS-stimulated RAW 264.7, a macrophage-cell line. Purified recombinant murine macrophage inflammatory protein-1 alpha (rmuMIP-α), was assessed for effects on proliferation of granulocyte-macrophage (CFU-GM), erythroid (BFU-E), and multipotential (CFU-GEMM) progenitor cells. The results suggest that rmuMIP-1α has myelosuppressive activity in vivo. The cDNA clone, called 4-1BB, is an inducible receptor-like sequence found in both cytolytic and helper T-cells.

4 Claims, 47 Drawing Sheets

```
                          -47  TTTTCTG TTCTGCTGAC AAGCTCACCC TCTGTCACCT GCTCAACATC  -1
  1  ATG AAG GTC TCC ACC ACT GCC CTT GCT GTT CTT CTC TGT ACC ATG ACA CTC TGC AAC CAA   60
  1  Met Lys Val Ser Thr Thr Ala Leu Ala Val Leu Leu Cys Thr Met Thr Leu Cys Asn Gln   20

61  GTC TTC TCA GCG CCA TAT GGA GCT GAC ACC CCG ACT GCC TGC TGC TTC TCC TAC AGC CGG  120
 21  Val Phe Ser Ala Pro Tyr Gly Ala Asp Thr Pro Thr Ala Cys Cys Phe Ser Tyr Ser Arg   40

121  AAG ATT CCA CGC CAA TTC ATC GTT GAC TAT TTT GAA ACC AGC AGC CTT TGC TCC CAG CCA  180
 41  Lys Ile Pro Arg Gln Phe Ile Val Asp Tyr Phe Glu Thr Ser Ser Leu Cys Ser Gln Pro   60

181  GGT GTC ATT TTC CTG ACT AAG AGA AAC CGG CAG ATC TGC GCT GAC TCC AAA GAG ACC TGG  240
 61  Gly Val Ile Phe Leu Thr Lys Arg Asn Arg Gln Ile Cys Ala Asp Ser Lys Glu Thr Trp   80

241  GTC CAA GAA TAC ATC ACT GAC CTG GAA CTG AAT GCC TGA GAG TCT TGG AGG CAG CCA GGA  300
 81  Val Gln Glu Tyr Ile Thr Asp Leu Glu Leu Asn Ala ---

301  ACC CCC CAA ACC TCC ATG GGT CCC GTG TAG AGC AGG GGC TTG AGC CCC GGA ACA TTC CTG  360
361  CCA CCT GCA TAG CTC CAT CTC CTA TAA GCT GTT TGC TGC CAA GTA GCC ACA TCG AGG GAC  420
421  TCT TCA CTT GAA ATT TTA TTT AAT TTA ATC CTA TTG GTT TAA TAC TAT TTA ATT TTG TAA  480
481  TTT ATT TTA TTG TCA TAC TTG TAT TTG TGA CTA TTT ATT CTG AAA GAC TTC AGG ACA CGT  540
541  TCC TCA ACC CCC ATC TCC CTC CCA GTT GGT CAC ACT GTT TGG TGA CAG CTA TTC TAG GTA  600
601  GAC ATG ATG ACA AAG TCA TGA ACT GAC AAA TGT ACA ATA GAT GCT TTG TTT ATA CCA GAG  660
661  AAG TAA TAA ATA TGC CCT TTA ACA AGT GAA AAA AAA
```

FIG. 2A

```
L2G25B (1)  Met Lys Val Ser Thr Thr Ala Leu Ala Val Leu Leu Cys Thr Met Thr Leu Cys Asn Gln
              *       *   *   *       *   *   *   *   *   *   *   *   *       *   *   *   *
PLD78  (1)  Met Gln Val Ser Thr Ala Ala Leu Ala Val Leu Leu Cys Thr Met Ala Leu Cys Asn Gln

Val Phe Ser Ala Pro Tyr Gly Ala Asp Thr Pro Thr Ala Cys Cys Phe Ser Tyr  -  Ser
              *   *   *       *       *   *   *   *   *   *   *   *   *   *   *   *       *
              -  Phe Ser Ala Ser Leu Ala Ala Asp Thr Pro Thr Ala Cys Cys Phe Ser Tyr Thr Ser
                          Δ

Arg Lys Ile Pro Arg Gln  -  Phe Ile Val Asp Tyr Phe Glu Thr Ser Ser Leu Cys Ser
              *   *   *       *           *   *       *   *   *   *   *   *   *       *   *
            Arg Gln Ile Pro  -  Gln Asn Phe Ile Ala Asp Tyr Phe Glu Thr Ser Ser Gln Cys Ser

Gln Pro Gly Val Ile Phe Leu Thr Lys Arg Asn Arg Gln Ile Cys Ala Asp  -  Ser Lys
              *   *   *   *   *   *   *   *   *   *       *   *       *   *   *       *
            Lys Pro Gly Val Ile Phe Leu Thr Lys Arg Ser Arg Gln Val Cys Ala Asp Pro Ser  -

Glu Thr Trp Val Gln Glu Tyr Ile Thr Asp Leu Glu Leu Asn Ala (stop) (92)
              *   *   *   *   *       *       *   *   *   *   *       *
            Glu Glu Trp Val Gln Lys Tyr Val Ser Asp Leu Glu Leu Ser Ala (stop) (92)
```

FIG. 2B

```
-145                                                                                      ATGTC
-140    CATGAACTGC TGAGTGGATA AACAGCACGG GATATCTCTG TCTAAAGGAA TATTACTACA CCAGGAAAAG
 -70    GACACATTCG ACAACAGGAA AGGAGCCTGT CACAGAAAAC CACAGTGTCC TGTGCATGTG ACATTTCGCC

1    ATG GGA AAC AAC TGT TAC AAC GTG GTG GTC ATT GTG CTG CTG CTA GTG GGC TGT GAG AAG   60
   1    Met Gly Asn Asn Cys Tyr Asn Val Val Val Ile Val Leu Leu Leu Val Gly Cys Glu Lys   20

61    GTG GGA GCC GTG CAG AAC TCC TGT GAT AAC TGT CAG CCT GGT ACT TTC TGC AGA AAA TAC  120
  21    Val Gly Ala Val Gln Asn Ser Cys Asp Asn Cys Gln Pro Gly Thr Phe Cys Arg Lys Tyr   40

121    AAT CCA GTC TGC AAG AGC TGC CCT CCA AGT ACC TTC TCC AGC ATA GGT GGA CAG CCG AAC  180
  41    Asn Pro Val Cys Lys Ser Cys Pro Pro Ser Thr Phe Ser Ser Ile Gly Gly Gln Pro Asn   60

181    TGT AAC ATC TGC AGA GTG TGT GCA GGC TAT TTC AGG TTC AAG AAG TTT TGC TCC TCT ACC  240
  61    Cys Asn Ile Cys Arg Val Cys Ala Gly Tyr Phe Arg Phe Lys Lys Phe Cys Ser Ser Thr   80

241    CAC AAC GCG GAG TGT GAG TGC ATT GAA GGA TTC CAT TGC TTG GGG CCA CAG TGC ACC AGA  300
  81    His Asn Ala Glu Cys Glu Cys Ile Glu Gly Phe His Cys Leu Gly Pro Gln Cys Thr Arg  100

301    TGT GAA AAG GAC TGC AGG CCT GGC CAG GAG CTA ACG AAG CAG GGT TGC AAA ACC TGT AGC  360
 101    Cys Glu Lys Asp Cys Arg Pro Gly Gln Glu Leu Thr Lys Gln Gly Cys Lys Thr Cys Ser  120

361    TTG GGA ACA TTT AAT GAC CAG AAC GGT ACT GGC GTC TGT CGA CCC TGG ACG AAC TGC TCT  420
 121    Leu Gly Thr Phe Asn Asp Gln Asn Gly Thr Gly Val Cys Arg Pro Trp Thr Asn Cys Ser  140

421    CTA GAC GGA AGG TCT GTG CTT AAG ACC GGG ACC ACG GAG AAG GAC GTG GTG TGT GGA CCC  480
 141    Leu Asp Gly Arg Ser Val Leu Lys Thr Gly Thr Thr Glu Lys Asp Val Val Cys Gly Pro  160

481    CCT GTG GTG AGC TTC TCT CCC AGT ACC ACC ATT TCT GTG ACT CCA GAG GGA GGA CCA GGA  540
 161    Pro Val Val Ser Phe Ser Pro Ser Thr Thr Ile Ser Val Thr Pro Glu Gly Gly Pro Gly  180

541    GGG CAC TCC TTG CAG GTC CTT ACC TTG TTC CTG GCG CTG ACA TCG GCT TTG CTG CTG GCC  600
 181    Gly His Ser Leu Gln Val Leu Thr Leu Phe Leu Ala Leu Thr Ser Ala Leu Leu Leu Ala  200

601    CTG ATC TTC ATT ACT CTC CTG TTC TCT GTC CTC AAA TGG ATC AGG AAA AAA TTC CCC CAC  660
 201    Leu Ile Phe Ile Thr Leu Leu Phe Ser Val Leu Lys Trp Ile Arg Lys Lys Phe Pro His  220

661    ATA TTC AAG CAA CCA TTT AAG AAG ACC ACT GGA GCA GCT CAA GAG GAA GAT GCT TGT AGC  720
 221    Ile Phe Lys Gln Pro Phe Lys Lys Thr Thr Gly Ala Ala Gln Glu Glu Asp Ala Cys Ser  240

721    TGC CGA TGT CCA CAG GAA GAA GAA GGA GGA GGA GGA GGC TAT GAG CTG TGA TGTACTATC    780
 241    Cys Arg Cys Pro Gln Glu Glu Glu Gly Gly Gly Gly Gly Tyr Glu Leu ---
```

FIG. 3A

```
 781    CTAGGAGATG TGTGGGCCGA AACCGAGAAG CACTAGGACC CCACCATCCT GTGGAACAGC ACAAGCAACC    850

851    CCACCACCCT GTTCTTACAC ATCATCCTAG ATGATGTGTG GGCGCGCACC TCATCCAAGT CTCTTCTAAC    920

921    GCTAACATAT TTGTCTTTAC CTTTTTTAAA TCTTTTTTTA AATTTAAATT TTATGTGTGT GAGTGTTTTG    990

991    CCTGCCTGTA TGCACACGTG TGTGTGTGTG TGTGTGTGAC ACTCCTGATG CCTGAGGAGG TCAGAAGAGA   1060

1061    AACGGTTGGT TCCATAAGAA CTGGAGTTAT GGATGGCTGT GAGCCCGGnnn GATAGGTCGG GACGGAGACC   1130

1131    TGTCTTCTTA TTTTAACGTG ACTGTATAAT AAAAAAAAAA TGATATTTCG GAATTGTAG AGATTGTCCT    1200

1201    GACACCCTTC TAGTTAATGA TCTAAGAGGA ATTGTTGATA CGTAGTATAC TGTATATGTG TATGTATATG   1270

1271    TATATGTATA TATAAGACTC TTTTACTGTC AAAGTCAACC TAGAGTGTCT GGTTACCAGG TCAATTTTAT   1340

1341    TGGACATTTT ACGTCACACA CACACACACA CACACACACA CACGTTTATA CTACGTACTGT TATCGGTAT   1410

1411    TCTACGTCAT ATAATGGGAT AGGGTAAAAG GAAACCAAAG AGTGAGTGAT ATTATTGTGGA GGTGACAGA   1480

1481    CTACCCCTTC TGGGTACGTA GGGACAGACC TCCTTCGGAC TGTCTAAAAC TCCCCTTAGA AGTCTCGTCA   1550

1551    AGTTCCCGGA CGAAGAGGAC AGAGGAGACA CAGTCCGAAA AGTTATTTTT CCGGCAAATC CTTTCCCTGT   1620

1621    TTCGTGACAC TCCACCCCTT GTGGACACTT GAGTGTCATC CTTGCGCCGG AAGGTCAGGT GGTACCCGTC   1690

1691    TGTAGGGGCG GGGAGACAGA GCCGCGGGGG AGCTACGAGA ATCGACTCAC AGGGCGCCCC GGGCTTCGCA   1760

1761    AATGAAACTT TTTTAATCTC ACAAGTTTCG TCCGGGCTCG GCGGACCTAT GGCGTCGATC CTTATTACCT   1830

1831    TATCCTGGCG CCAAGATAAA ACAACCAAAA GCCTTGACTC CGGTACTAAT TCTCCCTGCC GGCCCCCGTA   1900

1901    AGCATAACGC GGCGATCTCC ACTTTAAGAA CCTGGCCGCG TTCTGCCTGG TCTCGCTTTC GTAAACGGTT   1970

1971    CTTACAAAAG TAATTAGTTC TTGCTTTCAG CCTCCAAGCT TCTGCTAGTC TATGGCAGCA TCAAGGCTGG   2040

2041    TATTTGCTAC GGCTGACCGC TACGCCGCCG CAATAAGGGT ACTGGGCGGC CGTCGAAGG CCCTTTGGTT    2110

2111    TCAGAAACCC AAGGCCCCCC TCATACCAAC GTTTCGACTT TGATTCTTGC CGGTACGTGG TGGTGGGTGC   2180

2181    CTTAGCTCTT TCTCGATAGT TAG AC
```

FIG. 3B

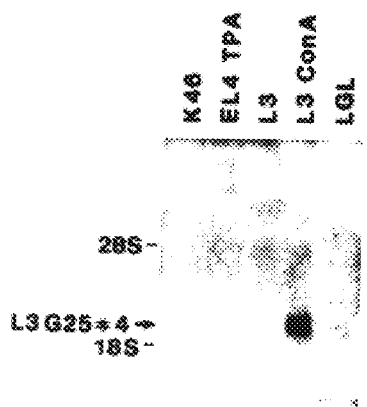
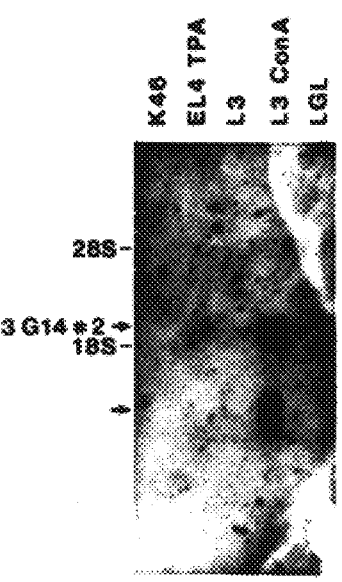
FIG. 4A  FIG. 4B  FIG. 4C
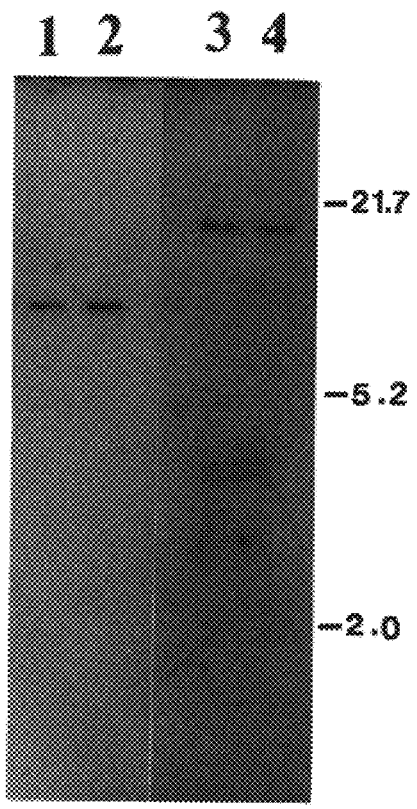
FIG. 5

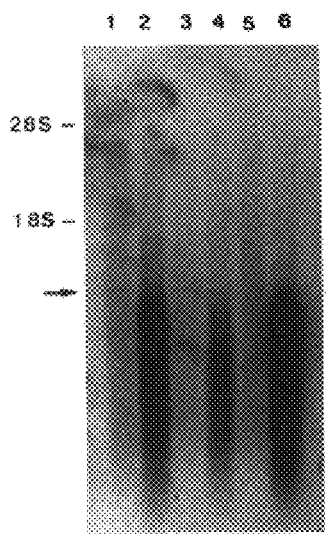
FIG. 8A
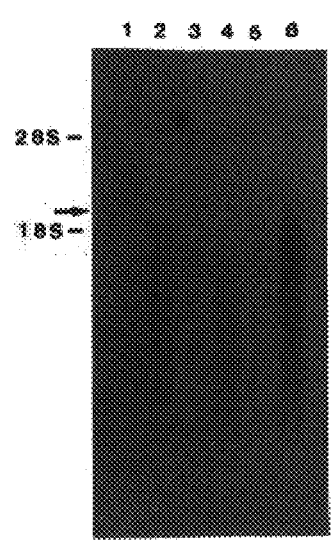
FIG. 8B
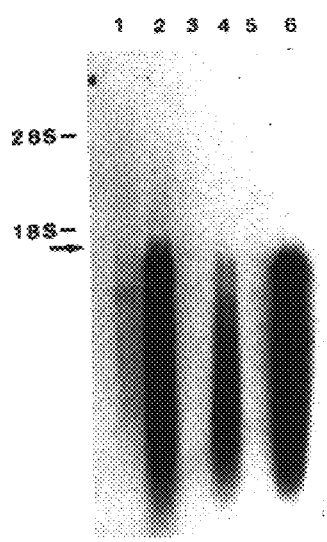
FIG. 8C
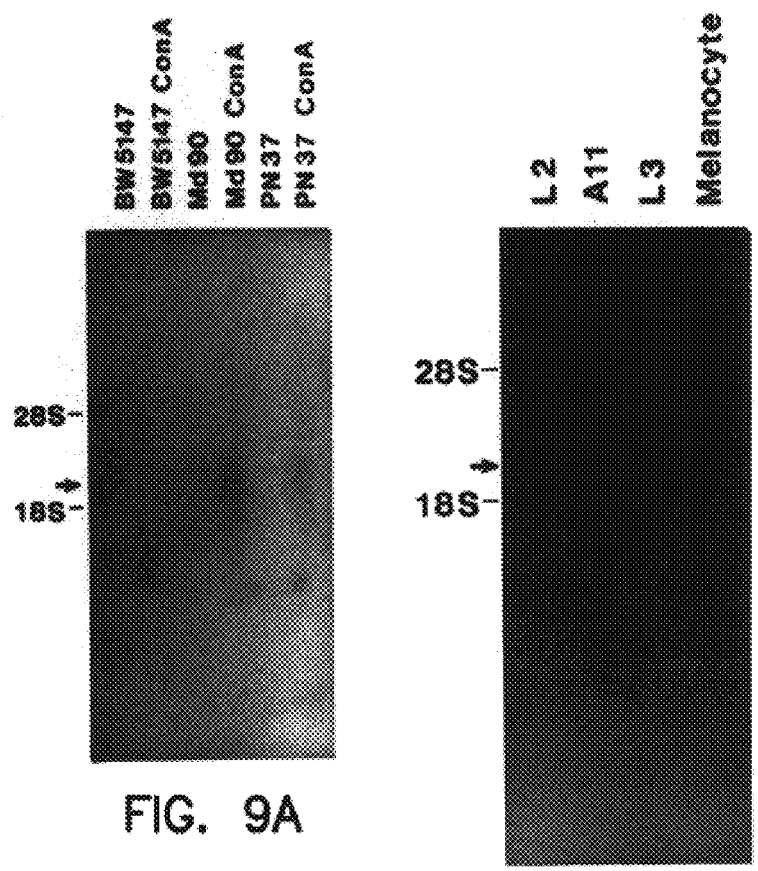
FIG. 9A
FIG. 9B Influence of MIP-1β, hemin, and inactive H-ferritin mutein on suppressive effects of MIP-1α and wildtype H-ferritin on myeloid colony formation[a]

| | Colony Formation | | | | | |
|---|---|---|---|---|---|---|
| | CFU-GM (huRGM-CSF, 100 U/ml + MGF, 50 ng/ml) | | BFU-E (Epo, 1 U/ml+ fusion protein, 2 ng/ml) | | CFU-GEMM (Epo, 1 U/ml + MGF 50 ng/ml) | |
| | −Hemin | +Hemin | −Hemin | +Hemin | −Hemin | +Hemin |
| Control medium | 103 ± 10 | 93 ± 3 | 56 ± 4 | 85 ± 3 | 47 ± 3 | 65 ± 3 |
| H-ferritin wildtype ($10^{-10}$ M) | 27 ± 2 (−74)[b,c] | 89 ± 9 (−4) | 31 ± 2 (−45)[c] | 88 ± 2 (+4) | 23 ± 1 (−51)[c] | 69 ± 2 (+6) |
| H-ferritin mutein 222 ($10^{-9}$ M) | 98 ± 6 (−5) | 106 ± 8 (+14) | 57 ± 3 (+1) | 90 ± 5 (+6) | 46 ± 3 (−2) | 69 ± 2 (+6) |
| MIP-1α (50 ng/ml) | 30 ± 1 (−71)[c] | 22 ± 3 (−76)[c] | 31 ± 2 (−45)[c] | 30 ± 2 (−65)[c] | 19 ± 2 (−60)[c] | 27 ± 4 (−58)[c] |
| MIP-1β (200 ng/ml) | 108 ± 5 (+5) | 92 ± 4 (−1) | 56 ± 3 (0) | 88 ± 4 (+4) | 46 ± 2 (−2) | 64 ± 3 (−2) |
| H-ferritin wildtype ($10^{-10}$ M) + MIP-1α (50 ng) | 27 ± 3 (−74)[c] | 19 ± 4 (−80)[c] | 29 ± 1 (−48)[c] | 29 ± 3 (−66)[c] | 21 ± 1 (−55)[c] | 22 ± 1 (−66)[c] |
| H-ferritin wildtype ($10^{-10}$ M) + H-ferritin mutein ($10^{-9}$ M) | 91 ± 3 (−12) | 90 ± 6 (−3) | 49 ± 5 (−13) | 83 ± 4 (−2) | 42 ± 3 (−11) | 66 ± 2 (+2) |
| MIP-1α (50 ng) + MIP-1β (200 ng) | 100 ± 4 (−3) | 97 ± 6 (+4) | 59 ± 2 (+5) | 87 ± 3 (+2) | 45 ± 3 (−4) | 67 ± 4 (+3) |
| H-ferritin wildtype ($10^{-10}$ M) + MIP-1β (200 ng) | 24 ± 1 (−77)[c] | 96 ± 4 (+3) | 30 ± 1 (−46)[c] | 87 ± 3 (+2) | 21 ± 1 (−55)[c] | 67 ± 3 (+3) |
| MIP-1α (50 ng) + H-ferritin mutein ($10^{-9}$ M) | 30 ± 2 (−71)[c] | 25 ± 3 (−73)[c] | 30 ± 2 (−46)[c] | 30 ± 2 (−65)[c] | 21 ± 2 (−55)[c] | 25 ± 4 (−62)[c] |
| MIP-1α (50 ng) + MIP-1β (200 ng) + H-ferritin wildtype ($10^{-10}$ M) | 28 ± 1 (−73)[c] | 105 ± 5 (+13) | 28 ± 2 (−50)[c] | 86 ± 3 (+1) | 21 ± 2 (−55)[c] | 67 ± 1 (+3) |
| H-ferritin wildtype ($10^{-10}$ M) + MIP-1α (50 ng) + H-ferritin mutein ($10^{-9}$ M) | 24 ± 3 (−77)[b] | 26 ± 4 (−72)[b] | 26 ± 4 (−54)[c] | 28 ± 2 (−67)[c] | 23 ± 4 (−51)[c] | 24 ± 1 (−63)[c] |
| H-ferritin wildtype ($10^{-10}$ M) + MIP-1α (50 ng) + MIP-1β (200 ng) | 98 ± 5 (−5) | 101 ± 6 (+9) | 56 ± 3 (0) | 85 ± 5 (0) | 46 ± 3 (−2) | 65 ± 3 (0) |

[a] NALDT⁻ cells were plated at $2.5 \times 10^4$/ml. The CFU-GM assay was set up in agar culture medium. Hemin (Kodak) was used at 0.1 mM.
[b] Values in parentheses are percent change from control medium.
[c] Significant percent change from control medium. $p < 0.001$; other numbers are not significantly different from control. $p > 0.05$.

FIG. 20

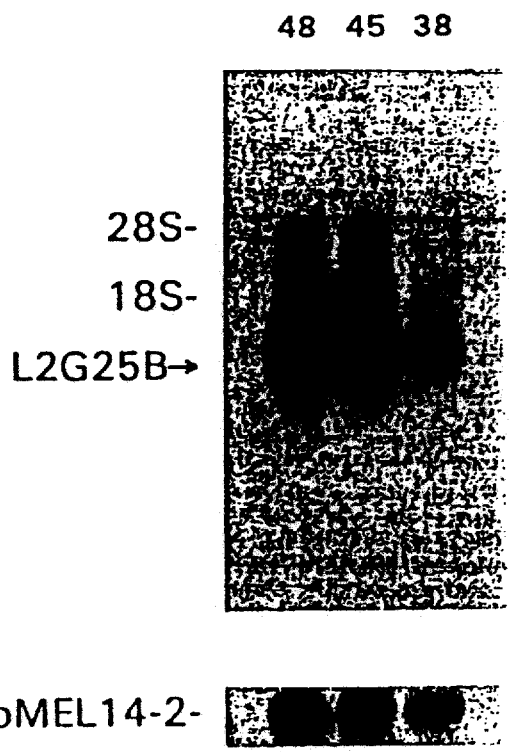
FIG. 21
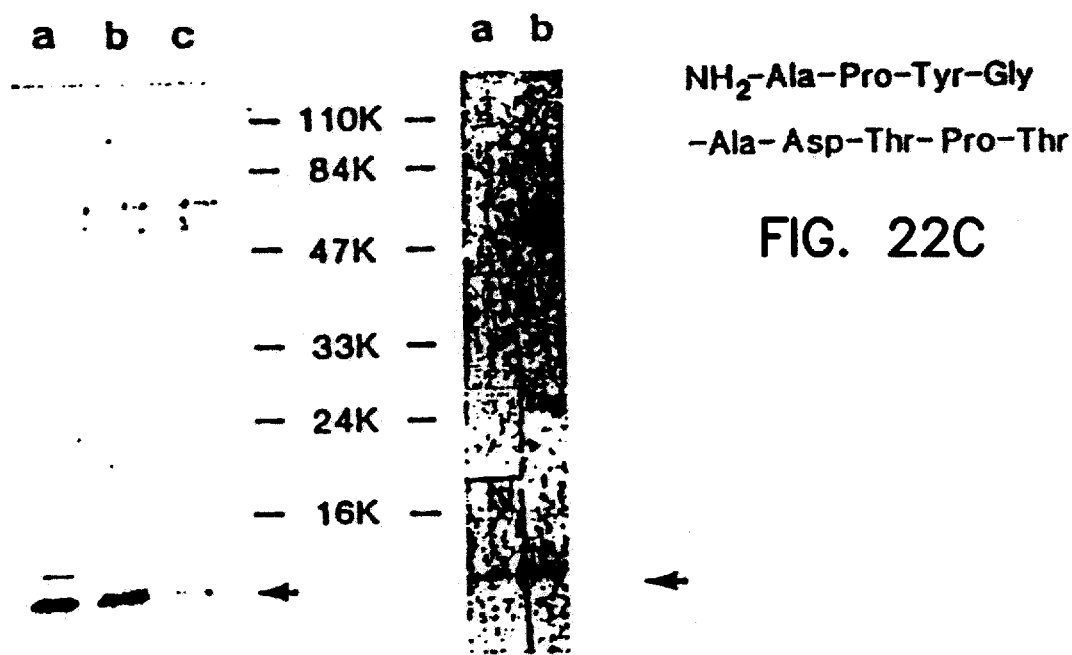
FIG. 22A    FIG. 22B
NH₂-Ala-Pro-Tyr-Gly
-Ala-Asp-Thr-Pro-Thr
FIG. 22C

```
4-1BB  (64)  C R V C A G Y F R F   K K · · F · C S S T H N A E C · C · E C
Sina   (71)  C P V C F D Y V · · · · · · I L Q C S S G H L V · C V S C
DG17   (25)  C P I C F E F I · Y K K Q I Y Q C K S G H H A · C K E C
```

FIG. 47

NUCLEIC ACID ENCODING MIP-1α LYMPHOKINE

This application is a continuation-in-part of application Ser. No. 07/267,577 filed Nov. 7, 1988, now abandoned.

The subject matter described herein was in part a subject invention of NIH Grants Nos. IR23AI23058-03, RO1 AI28175 and P60 KD20542 of which the present inventor was the Principal Investigator and either the Donald Guthrie Foundation for Medical Research Inc. of Guthrie Square, Sayre, Pa. 18849-1669 or Indiana University School of Medicine of Indianapolis, Ind. 46202, was the Grantee.

FIELD OF THE PRESENT INVENTION

Lymphokines are the proteins by which the immune cells communicate with each other. Scientists produce them in sufficient quantities for therapeutic use against immunologic diseases. The present invention relates particularly to previously unknown lymphokine and receptor proteins which were isolated and identified based on specific expression of the T cell genes using a technique identified by the present inventor in a publication (*Proc. Natl. Acad. Sci. USA*, 84, 2896–2900, May 1987, Immunology).

BACKGROUND OF THE PRESENT INVENTION

The immune system of humans and other species requires that white blood cells be made in the bone marrow, which white blood cells include phagocytes, lymphocytes and B cells. As presently understood, the phagocytes include macrophage cells which scavenge unwanted materials such as virus protein from the system. The lymphocytes include helper T cells and killer T cells and B cells as well as other cells, including those categorized as suppressor T cells.

The B cells produce the antibodies. The killer T cells physically pierce the cell and the helper T cells facilitate the whole process. In any event, the immune process is facilitated by lymphokines. Interleukin 1, secreted from macrophages activate the helper T cells and raise the body temperature causing fever which enhances the activity of the immune cells. The activated helper T cells produce Interleukin 2 and Interleukin stimulates the helper and killer T cells to grow and divide. The helper T cells also produce another lymphokine, B cell growth factor (BCGF), which causes B cells to multiply. As the number of B cells increases, the helper T cells produce another lymphokine known as the B cell differentiating factor (BCDF), which instructs some of the B cells to stop replicating and start producing antibodies. T cells also produce a lymphokine, gamma interferon (IF), which has multiple effects like Interleukin 2. Interferon helps activate killer T cells, enabling them to attack the invading organisms. Like BCGF, interferon increases the ability of the B cells to produce antibodies. Interferon also affects the macrophages to keep them at the site of the infection and help the macrophages to digest the cells they have engulfed. Gathering momentum with each kind of lymphokine signal between the macrophages and the T cells, the lymphokines amplify the immune system response and the virus protein or other foreign matter on the infected cells is overwhelmed. There are many other lymphokines, maybe a hundred or more, which participate in the immune process. Many lymphokines are known and many are not.

Lymphokines are sometimes called intercellular peptide signals. Among scientists there is widespread use of cloned cell lines as lymphokine producers and the isolation of lymphokine mRNA has become a common technique.

The protocol reported in the aforesaid publication can be used by scientists to detect virtually all of the lymphokines because the method is designed to detect virtually all the mRNA expressed differentially and the mRNA sequences of the immune cells are expressed differentially as they relate to the T cells and the killer T cells even though the level of expression is low and the quantity of the secreted lymphokine protein is low. The present inventor believes that the analysis described in the above identified publication can reveal biologically important molecules such as lymphokines because there are many indications that biologically important or active molecules are coded by the most scarce messages. An example is a transforming growth factor (TGF) which is present as only one of a million clones.

There are many known lymphokine proteins and they include the interferons, interleukin-1,2,3,4,5,6,7, colony-stimulating factors, lymphotoxin, tumor necrosis factor and erythropoietin, as well as others.

Most T cell factors have been classically identified by recognizing biologic activities in assays, purifying the protein information. An alternative approach is to isolate putative T cell genes based upon specific expression and then demonstrate the function of the unknown molecule. Using the aforesaid modified differential screening procedure, the present inventor has recently cloned a series of T cell subset-specific cDNAs from cloned helper T (HTL) L2 and cloned cytolytic T lymphocyte (CTL) L3.

SUMMARY OF THE PRESENT INVENTION

Apparent full length cDNAs corresponding to fourteen species of the 16 initial isolates were sequenced and were found to constitute five different species.

Three of the five were identical to previously reported cDNA sequences of proenkephalin, T cell replacing factor and HF gene (a serine esterase). The other two, represented as L2G25B and 4-1BB, were novel sequences of unknown function. The open reading frames of 4-1BB and L2G25B code for 245 and 92 amino acids, respectively. The predicted proteins of 4-1BB and L2G25B include 22 and 23 amino acid-long putative signal sequences, respectively. The protein backbones of mature proteins encoded by 4-1BB and L2G25B are composed of 234 amino acids with molecular weight of 25000 and 69 amino acids with molecular weight of 7880, respectively. 4-1BB contains two potential N-glycosylation sites while L2G25B has none. 4-1BB contains 23 cysteine residues in the putative mature protein.

The cDNA L2G25B encodes for the lymphokine, macrophage inflammatory protein-1α or MIP-1α. MIP-1α has been described in a paper entitled, "Enhancing and Suppressing Effects of Recombinant Murine Macrophage Inflammatory Proteins on Colony Formation In Vitro by Bone Marrow Myeloid Progenitor Cells", Hal E. Broxmeyer, Barbara Sherry, Li Lu, Scott Cooper, Kwi-Ok Oh, Patricia Tekamp-Olson, Byoung S. Kwon, and Anthony Cerami, *Blood*, 76, 111–1116, 1990 and is incorporated herein by reference. This was the first time the suppressing activity of MIP-1α was characterized. Natural MIP-1 was found and characterized as an inflammatory protein in 1988 (Wolpe, S. D., G. Davatelis, B. Sherry, B. Beutler, D. G. Hesse, H. T. Hguyen, L. L. Moldawer, C. F. Nathan, S. F. Lowry, and A. Cerami. 1988. Macrophages secrete a novel heparin-binding protein with inflammatory and neutrophil chemokinetic properties. *J. Exp. Med.*, 167, 570, incorporated herein by reference). The sequence for MIP-1α was also published in June 1988 (Davatelis, G., P. Tekamp-Olson, S. D. Wolpe, K. Hermsen, C. Luedke Gallegos, D.

Cort, J. Merryweather, and A. Cerami. 1988. Cloning and characterization of a cDNA for murine macrophage inflammatory protein (MIP), a novel monokine with inflammatory and chemokinetic properties. *J. Exp. Med.,* 167, 1939, incorporated herein by reference). The myelopoietic enhancing effects on colony formation in vitro by murine and human bone marrow granulocyte/macrophage progenitor cells was published in 1989 (Broxmeyer, H. E., B. Sherry, L. Lu, S. Cooper, C. Carow, S. D. Wolpe, and A. Cerami. 1989. Myelopoietic enhancing effects of murine macrophage inflammatory proteins and human bone marrow granulocyte/macrophage progenitor cells. *J. Exp. Med.,* 170, 1583, incorporated herein by reference). In 1990, Graham and Pragnell identified and characterized an inhibitor of hematopoietic stem cell proliferation which turned out to be MIP-1α. (Graham, G. J., E. G. Wright, R. Hewick, S. D. Wolpe, N. M. Wilke, D. Donaldson, S. Lorimore, and I. B. Pragnell. 1990. Identification and characterization of an inhibitor of haematopoietic stem cell proliferation. *Nature,* 344, 442, incorporated herein by reference). Graham and Pragnell have also published work on in vivo experiments of the suppressing effects of MIP-1α (David J. Dunlop, Eric G. Wright, Sally Lorimore, Gerald J. Graham, Tessa Holyoake, David J. Derr, Stephen D. Wolpe, and Ian B. Pragnell. 1992. Demonstration of Stem Cell Inhibition and Myeloprotective Effects of SCI/rhMIP-1α In Vivo, *Blood,* 79, No. 9, pp. 2221–2225, incorporated herein by reference).

The present invention includes the discovery of the cDNA sequence encoding for the protein later referred to as MIP-1α and the recombinant protein. A new use of a known human protein PLD78 has been discovered, wherein the new use is as a human lymphokine. The cDNA and fragments and derivatives thereof can be used as probes to isolate DNA sequences encoding for proteins similar to the lymphokine MIP-1α. A method of suppressing progenitor cell cycling in a human patient prior to chemotherapy treatment has been developed. An appropriate dose of MIP-1α is administered to the patient to suppress early myeloid progenitor cell cycling and thereby suppress stem cell colony formation. Once the patient's normal stem cell colonies are reduced, the chemotherapy treatment is administered. This method is based upon the work disclosed herein and the use of MIP-1α to suppress progenitor cell cycling in vivo in mice.

The effects of recombinant (r) mu, MIP-1β and MIP-2 on the suppressive activity of MIP-1α were tested using colony formation by hu and mu bone marrow BFU-E, CFU-GEMM and CFU-GM progenitor cells. MIP-1β, but not MIP-2, when added with MIP-1α to cells, blocked the suppressive effects of MIP-1α on both hu and mu BFU-E, CFU-GEMM and CFU-GM colony formation. Similar results were observed regardless of the early acting cytokines used: rhuGM-CSF plus rhuIL-3, and two recently described potent cytokines, a genetically engineered rhuGM-CSF/IL-3 fusion protein and MGF, a c-kit ligand. The more potent the stimuli, the greater the suppressive activity noted. Pulse treatment of hu bone marrow cells with MIP-1α at 4° C. for 1 hr. was as effective in inhibiting colony formation as continuous exposure of cells to MIP-1α, and the pulsing effect with MIP-1α could not be overcome by subsequent exposure of cells to MIP-1β. Also, pulse exposure of cells to MIP-1β blocked the activity of subsequently added MIP-1α. For specificity, the action of a non-related myelosuppressive factor H-ferritin, was compared. MIP-1α and H-ferritin were shown to act on similar target populations of early BFU-E, CFU-GEMM and CFU-GM. MIP-1β did not block the suppressive activity of H-ferritin. Also, hemin and an inactive rhuH-ferritin mutein counteracted the suppressive effects of the wildtype H-ferritin molecule, but did not block the suppressive effects of MIP-1α. These results show that MIP-1β's ability to block the action of MIP-α is specific. In addition, the results suggest that MIP-1α and MIP-β can, through rapid action, modulate early myeloid progenitor cell proliferation.

Recombinant proteins have been produced for the cytokine, L2G25BP (Macrophage Inflammatory Protein-1α, MIP-1α). By employing the recombinant protein (rMIP-1α), receptors for MIP-1α were identified on Con A-stimulated and unstimulated CTLL-R8, a T-cell line, and LPS-stimulated RAW 264.7, a macrophage-cell line. The $^{125}$I-rMIP-1α binds to the receptor in a specific and saturable manner. Scatchard analysis indicated a single class of high affinity receptor with a Kd of approximately $1.5\times10^{-9}$M and approximately 1200 binding sites per Con A stimulated CTLL-R8 cell, and a Kd of $0.9\times10^{-9}$M and approximately 380 binding sites per RAW 264.7 cell. $^{125}$I-rMIP-1α binding was inhibited by unlabeled rMIP-1α in a dose-dependent manner, but not by IL-1α or IL-2. rMIP-1α inhibited the proliferation of unstimulated CTLL-R8 cells. Rabbit anti rMIP-1α antibodies blocked the growth inhibitory effect of the rMIP-1α on CTLL-R8 cells.

Purified recombinant murine macrophage inflammatory protein-1 alpha (rmuMIP-1α), a cytokine with myelopoietic activity in vitro, was assessed in vivo by injection into C3H/HeJ mice for effects on proliferation (percentage of cells in S-phase) and absolute numbers of granulocyte-macrophage (CFU-GM), erythroid (BFU-E), and multipotential (CFU-GEMM) progenitor cells in the femur and spleen, and on nucleated cellularity in the bone marrow, spleen and blood. RmuMIP-1α rapidly decreased cycling rates (at 2–10 ug/mouse i.v.) and absolute numbers (at 5–10 ug/mouse i.v.) of myeloid progenitor cells in the marrow and spleen. These effects were dose- and time-dependent and reversible. Suppressive effects were noted within 3 to 24 hours for cell cycling and absolute numbers of progenitor cells in the marrow and spleen, and by 48 hours for circulating neutrophils. A study comparing the effects of i.v. injection of rmuMIP-1α versus rmuMIP-1β, a biochemically similar molecule but with no myelosuppressive effects in vitro, demonstrated myelosuppression in vivo by rmuMIP-1α but not by rmuMIP-1β. The results show that rmuMIP-1α has myelosuppressive activity in vivo and may be a used as an adjunct to treatments involving cytotoxic drugs because of its reversible suppressive effects on normal progenitor cell cycling.

Macrophage inflammatory protein-1α (MIP-1α) is a member of the intercrine family which consists of basic, heparin-binding, small molecular weight proteins. A T-cell line CTLL-R8 cell was shown to carry high affinity receptors for MIP-1α and the proliferation of the CTLL-R8 cells was inhibited by murine recombinant (mr) MIP-1α. Previous studies were extended to murine resting splenic T lymphocytes to determine whether the inhibition of T-cell proliferation is a general property of MIP-1α. The resting splenic T-cells carried approximately 680 high affinity binding sites for mrMIP1α. More than 90% of the primary T-cells carried the MIP-1α receptors. When the T-cells are stimulated with immobilized antiCD3 mAb in the presence of accessory cells, the MIP-1α receptor expression was down-regulated. The lowest binding was obtained 2 hrs after the antiCD3 mAb stimulation. This down-regulation was associated with the internalization of its own ligand which were produced upon antiCD3 mAb stimulation, mrMIP-1α inhibited the antiCD3 mAb-medicated proliferation of the murine splenic T lymphocytes. The maximum inhibition was obtained when the mrMIP-1α was added 30 min prior to the antiCD3 mAb stimulation. Slight inhibition of the T cell proliferation was observed when the mrMIP-1α was added 2 hrs prior to or at the same time as antiCD3 mAb stimulation. These results indicate that T lymphocytes are regulated negatively by MIP-1 a, which occurs when the T-cells are exposed to MIP-1α prior to the activation. The negative effect of MIP-1α appears to be mediated by the inhibition of IL-2 production, for both IL-2 contents in the T-cell supernatant and IL-2 mRNA levels, were reduced.

The cDNA clone, called 4-1BB, was originally believed to be a lymphokine based upon the experiments disclosed herein. New studies show the 4-1BB is an inducible receptor-like sequence found in both cytolytic and helper T-cells. Polyclonal antibodies against oligopeptides representing the hydrophilic region of 4-1BB were prepared and used to characterize the properties of the molecule. The 4-1BB mRNA was detected in PMA-treated spleen and heart with constitutive expression detected in the kidney. FACS analysis and production of truncated, thus secretory, 4-1BB protein indicated that it is a cell-surface protein. The molecular size of 4-1BB protein was 40 kD. The 4-1BB protein was expressed on mononuclear cells infiltrating islet cells in the pancreata of NOD mice. Expression was prominent in the early phase of insulitis and the level of expression diminished or disappeared in the later phase. These data indicate that the 4-1BB protein is associated with T-cell activation and may play a role in the early phase of inflammation or autoimmune diseases.

The potential 4-1BB protein (4-1BBP) contains features seen in known receptor proteins and a region of amino acids similar to those in the nerve growth factor receptor, Drosophila gene sina, and Dictyostelium gene DG17. Polyclonal antibodies against a hydrophilic region of 4-1BBP were obtained and their distribution in the brain was examined. The specific expression pattern of 4-1BBP in the brain was identified in the gray matter where neuronal cell bodies, dendrites, and fiber terminals reside but was almost entirely absent in the white matter where axonal fibers dwell. A peculiar rosette pattern was observed in a granular layer of cerebellum and scattered in the stria terminalis. The staining pattern strongly resembled the receptor/nerve terminals in the brain and the peripheral nervous system. This study shows that the 4-1BBP is a novel receptor which may be associated with brain functions and is another example of a cell surface molecule found in both the immune and nervous systems.

The primary object is to provide the teachings identifying the new lymphokine and new receptor, L2G25B (MIP-1α) and 4-1BB as identified herein by their gene sequence.

Another object of the present invention is to provide teachings of how the new lymphokine and new receptor may be used to isolate and identify corresponding molecules in related species.

Still another object of the teachings of the present invention is to teach the identification of the new lymphokine and new receptor as reported herein.

BRIEF DESCRIPTIONS OF THE FIGURES

FIG. 2a shows the nucleotide and deduced amino acid sequence of the longest reading frame of the new mouse lymphokine L2G25B thereby defining the same.

FIG. 2b shows the optimum alignment between the new lymphokine L2G25B and a known human protein PLD78 which, as a result of the teachings herein, can also now be identified as a human lymphokine corresponding to mouse lymphokine L2G25B.

FIGS. 3a and 3b show the nucleotide sequence and the deduced amino acid sequence of mouse receptor 4-1BB.

FIGS. 4a, 4b, and 4c show an RNA blot analysis of ConA-stimulated L3 RNA with the expression being for different sizes of receptor 4-1BB mRNA.

FIG. 5 shows a Southern Blot analysis of mouse genomic DNA for fragments of L2G25B and 4-1BB cDNA.

Figure 6A:
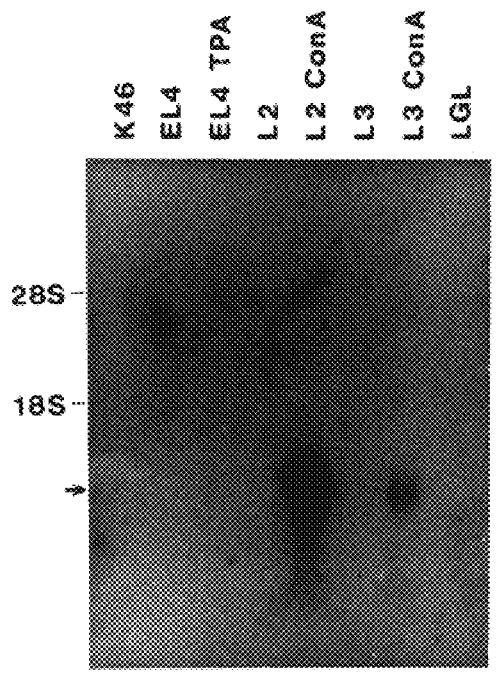
Figure 6B:
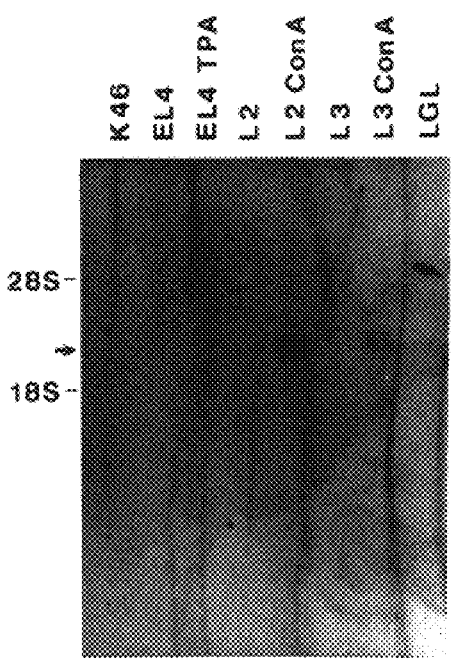

FIGS. 6a and 6b show L2G25B and 4-1BB expressed preferentially in L2 and L3 cells only after concanavalin A stimulation.

FIGS. 7a, 7b, 7c and 7d show RNA Blot patterns of lymphokine L2G25B and receptor 4-1BB in mRNA expression TCR stimulation or IL-2 treatment.

FIGS. 8a, 8b and 8c show expression of lymphokine L2G25B mRNA and receptor 4-1BB mRNA in a HTL L2 and a CTL dB45 cells.

FIGS. 9a and 9b show the expression of receptor 4-1BB mRNA in concanavalin A-stimulated hybridomas PN37 and Md90 and in an unstimulated CTL CTLLA11.

FIGS. 10a, 10b, 10c and 10d show the effect of cyclosporin A on L2G25B and 4-1BB mRNA expression.

Figure 11A:
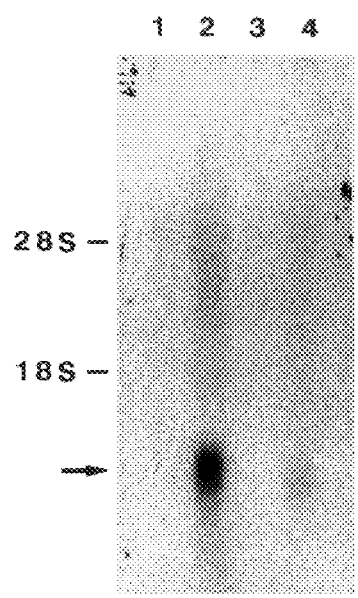
Figure 11B:
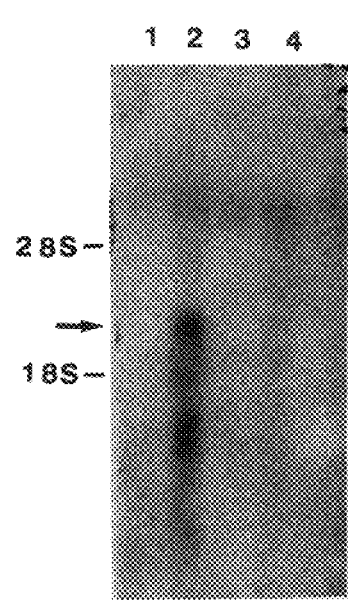
Figure 11C:
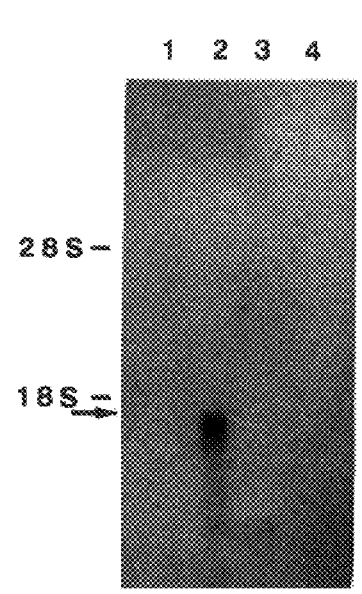

FIGS. 11a, 11b and 11c show the expression of lymphokine L2G25B and receptor 4-1BB mRNA in mouse splenocytes.

Figure 12:
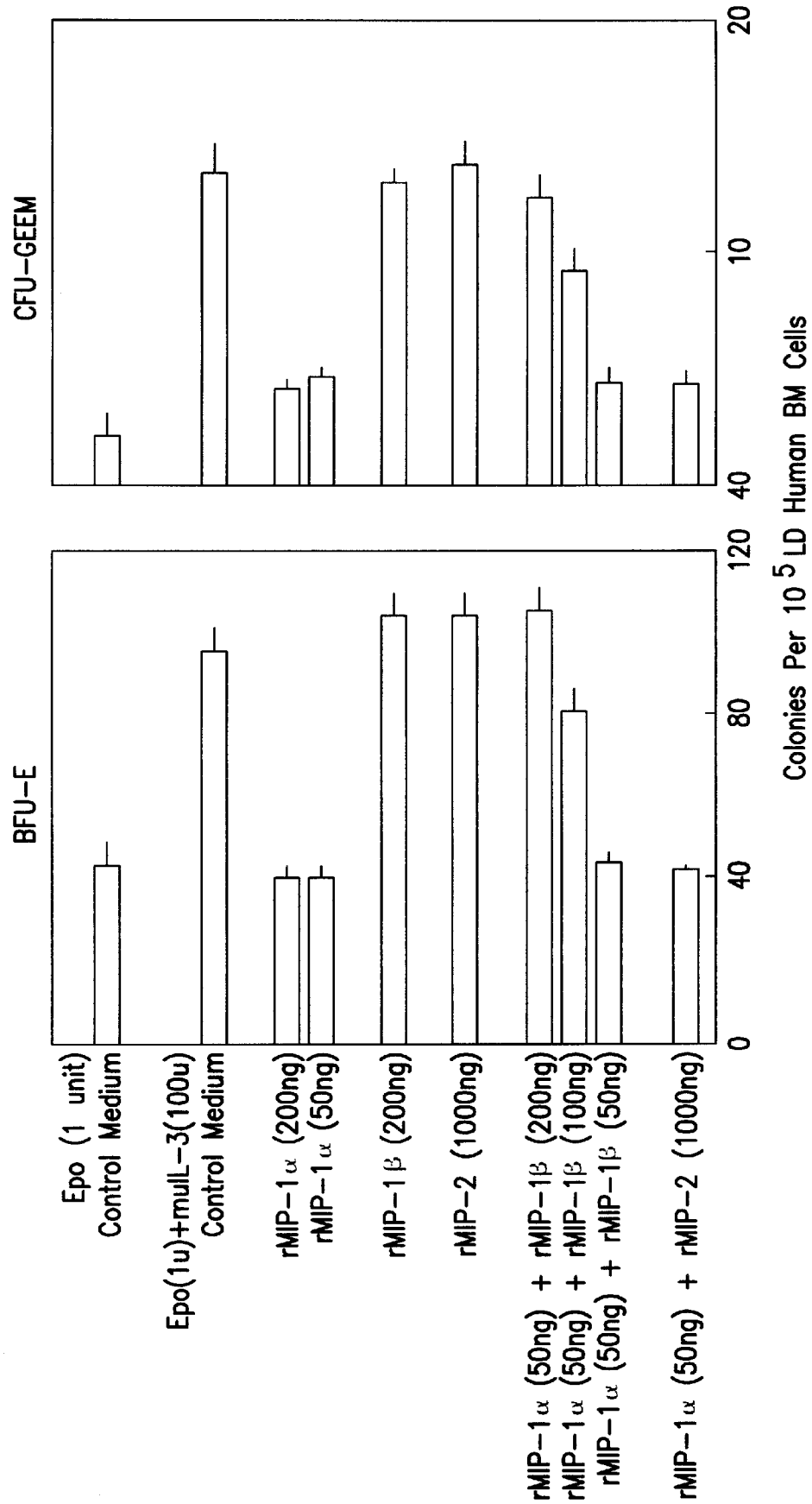

FIG. 12 shows the influence of MIP-1β and MIP-2 on the suppressive effects of MIP-1α on colony formation by low density (LD) human bone marrow (BM) erythroid (BFU-E) and multipotential (CFU-GEMM) progenitor cells stimulated by erythropoietin (Epo) plus interleukin (IL)-3.

Figure 13:
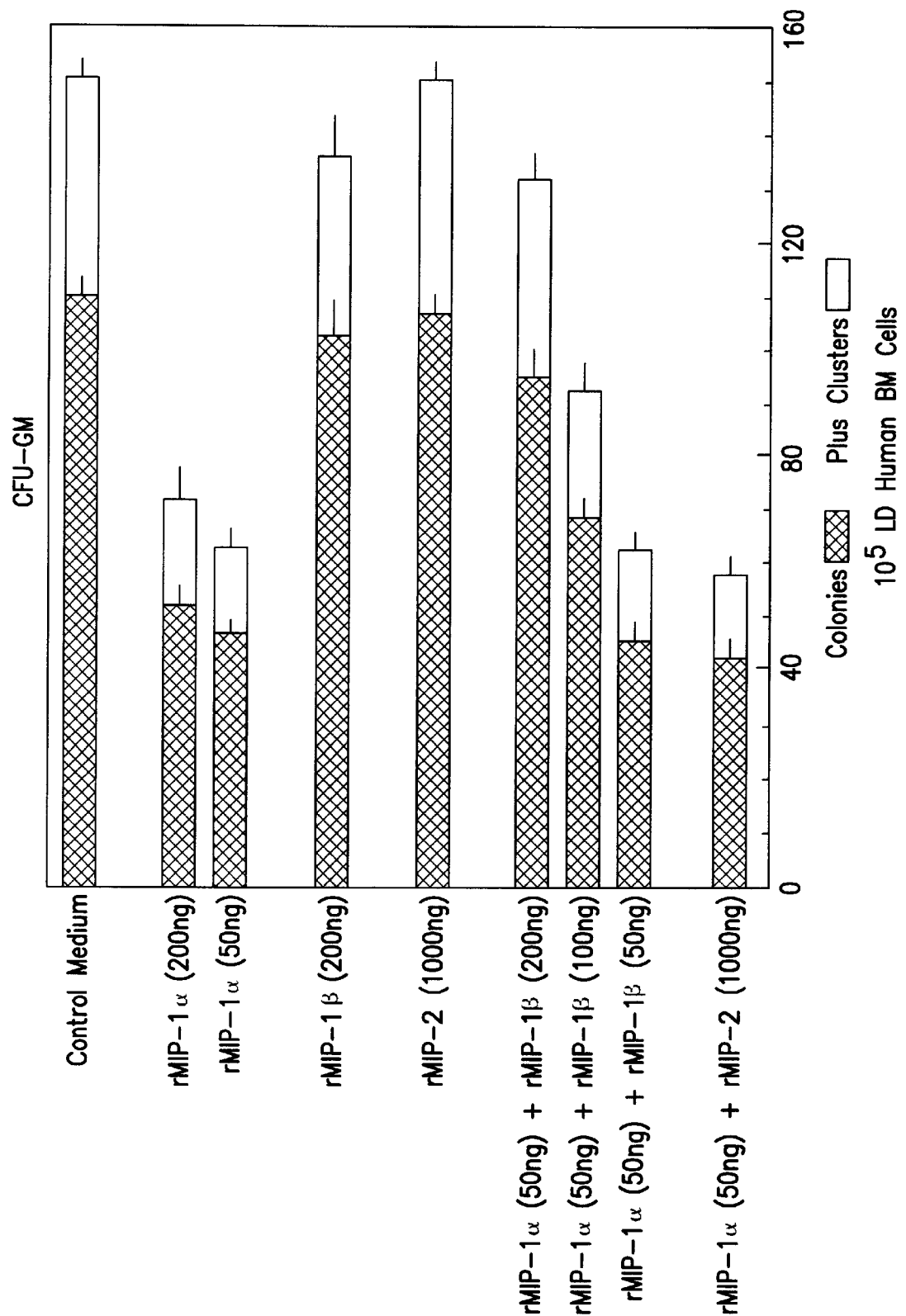

FIG. 13 shows the influence of MIP-1β and MIP-2 on the suppressive effects of MIP-1α on colony (>40 cells/aggregate) and cluster (3–40 cells/aggregate) formation by LD human BM CFU-GM stimulated by GM-CSF plus IL-3 in agarose culture medium.

Figure 14:
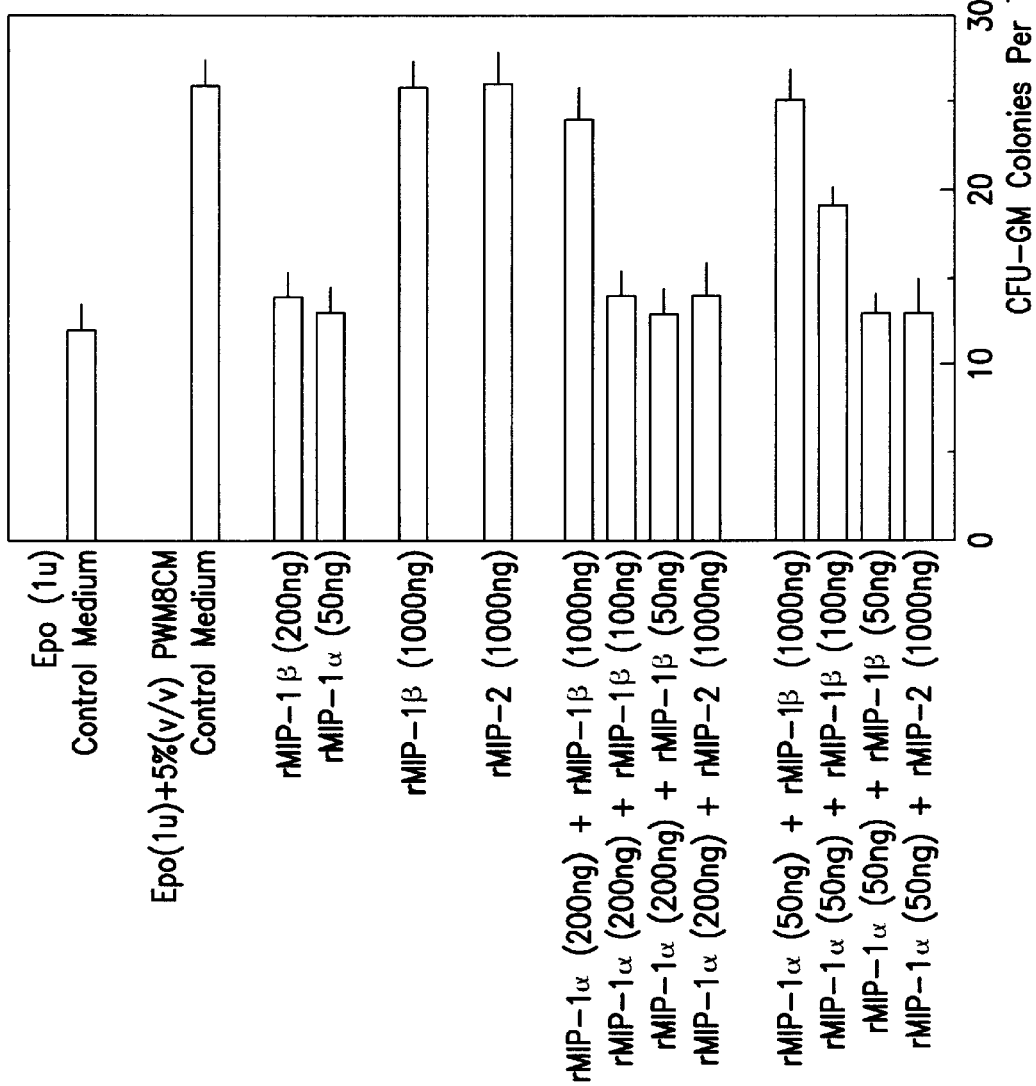

FIG. 14 shows the influence of MIP-1β and MIP-2 on the suppressive effects of MIP-1α on colony formation by mouse marrow BFU-E and CFU-GEMM stimulated by Epo and pokeweed mitogen mouse spleen cell conditioned medium (PWMSCM).

Figure 15:
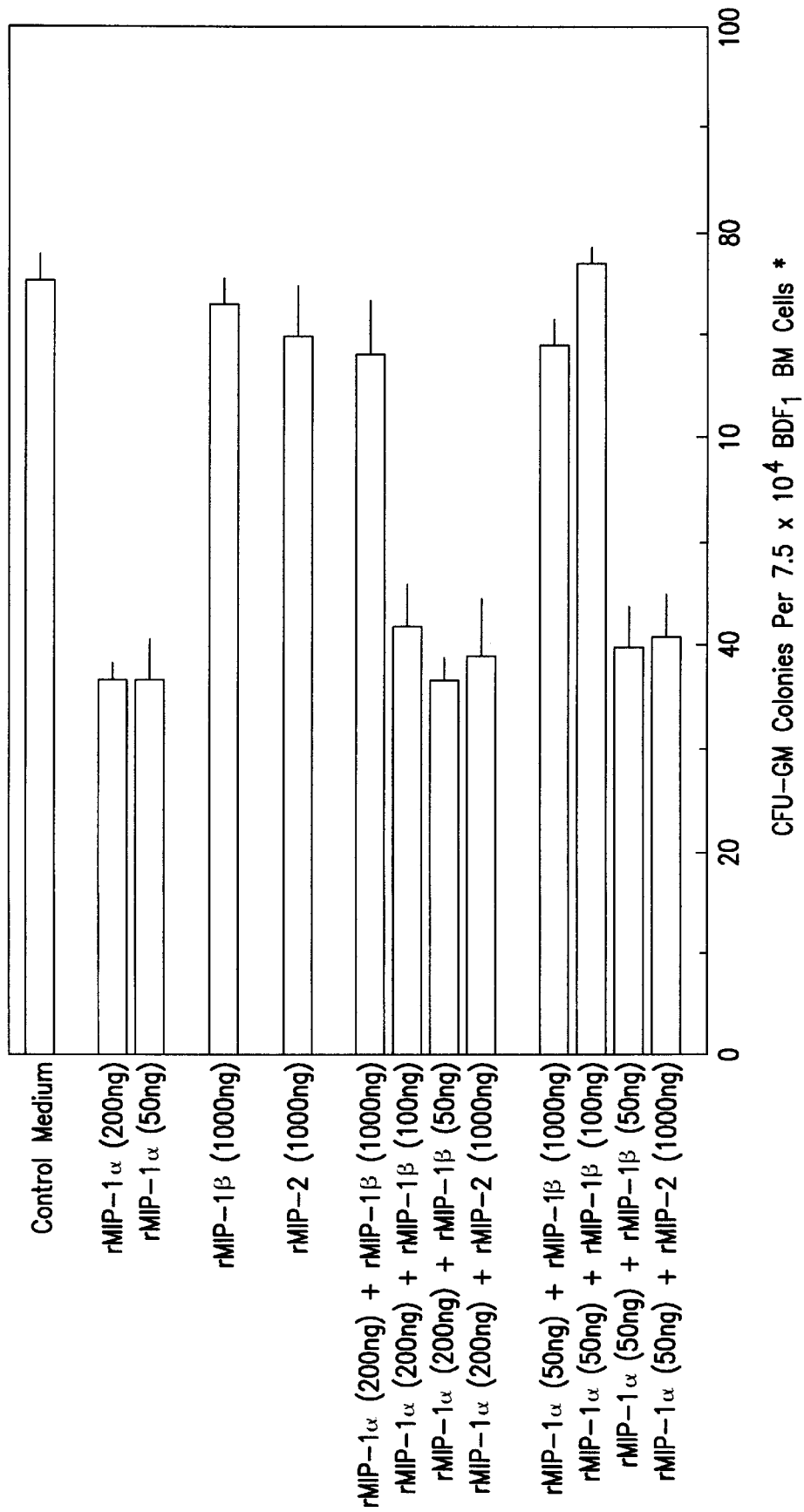

FIG. 15 shows the influence of MIP-1β and MIP-2 on the suppressive effects of MIP-1α on colony formation by mouse marrow CFU-GM stimulated by PWMSCM in agar culture medium.

Figure 16:
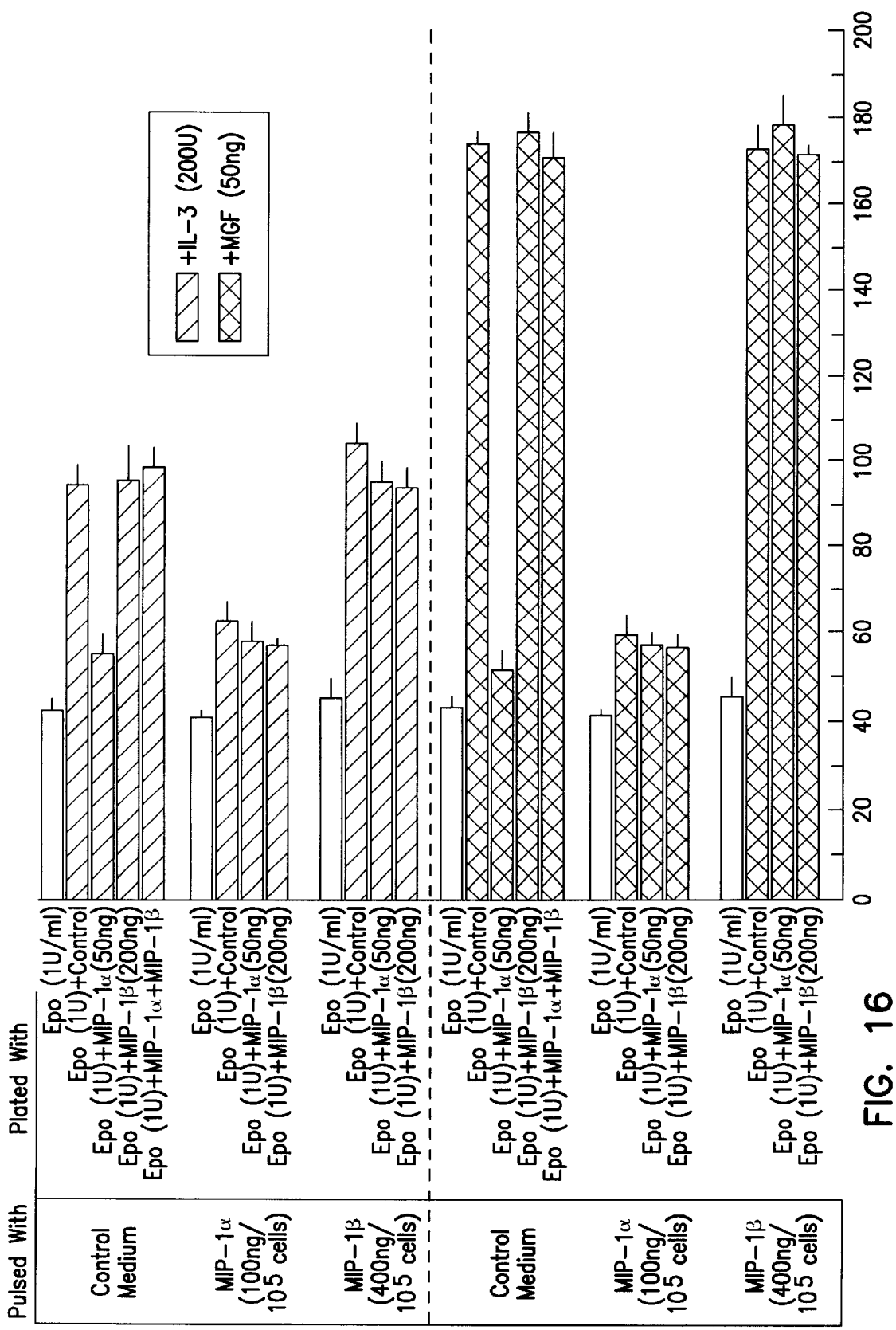

FIG. 16 shows the influence of pulse treatment of non-adherent low density T-lymphocyte depleted (NALDT) human bone marrow cells with MIP-1α or MIP-1β on colony formation by BFU-E stimulated with Epo plus IL-3 or mast cell growth factor (MGF).

Figure 17:
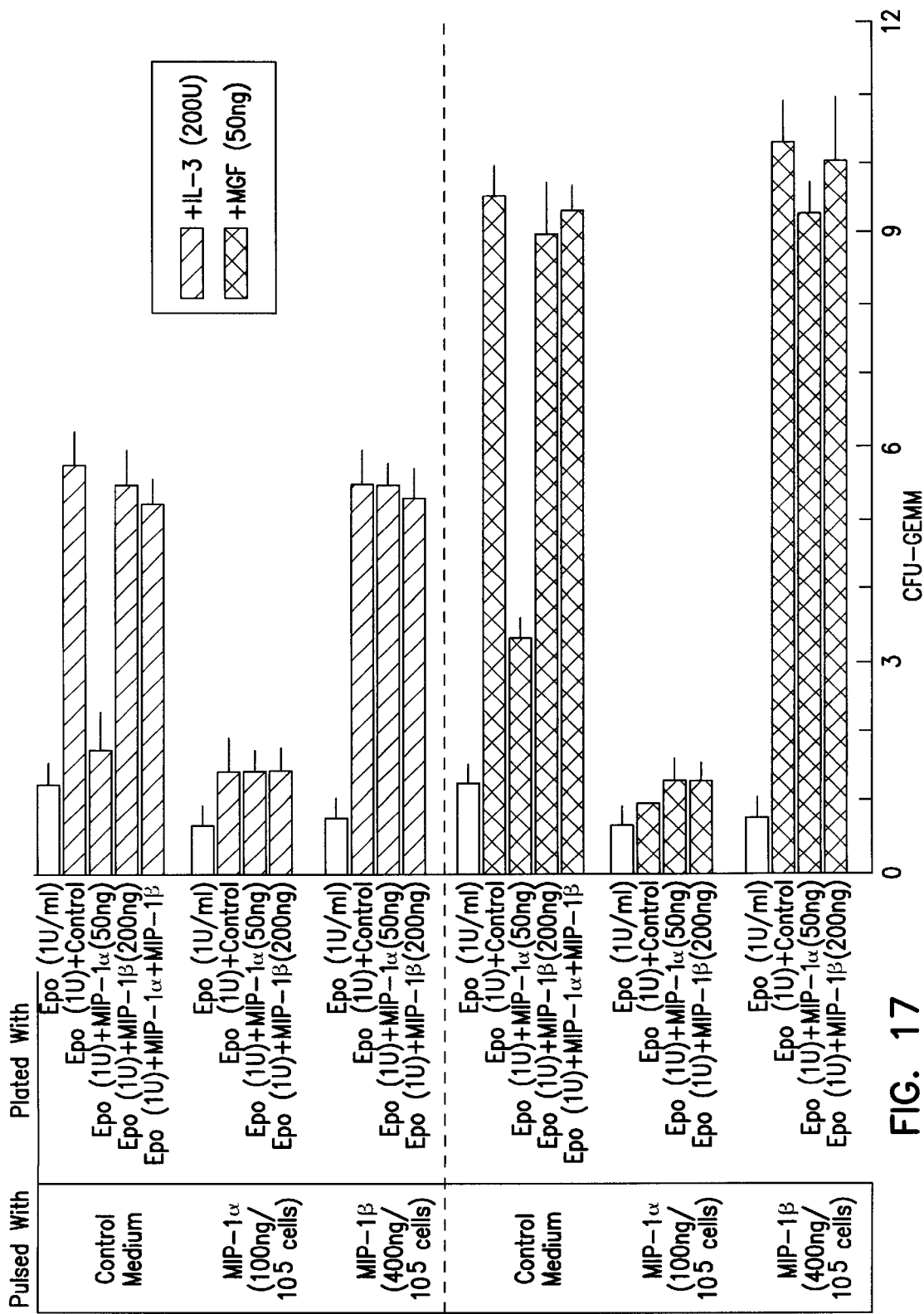

FIG. 17 shows the influence of pulse treatment of NALDT human marrow cells with MIP-1α or MIP-1β on colony formation by CFU-GEMM stimulated by Epo plus IL-3 or MGF.

Figure 18:
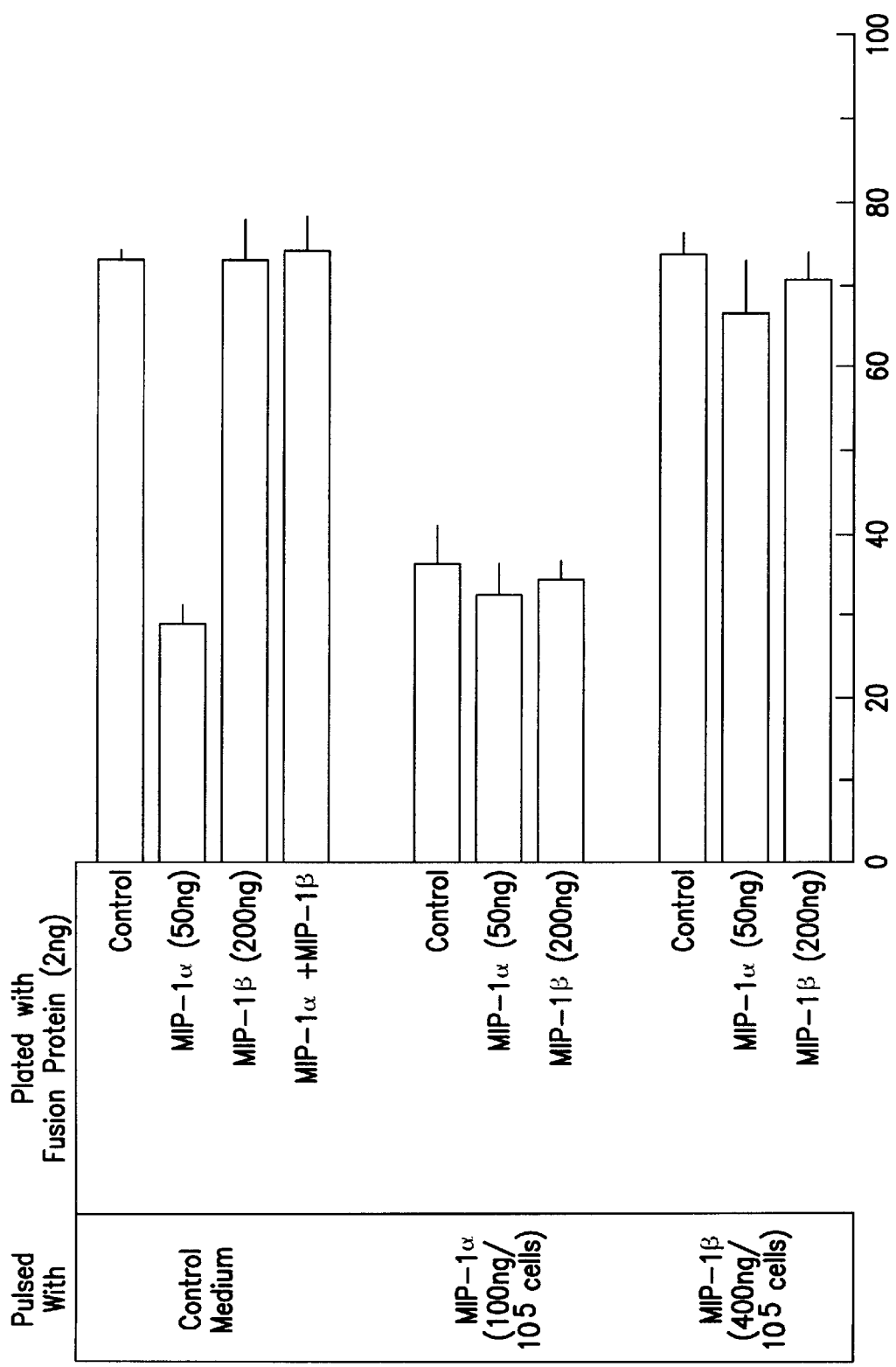

FIG. 18 shows the influence of pulse treatment of NALDT human marrow cells with MIP-1α or MIP-1β on colony formation by CFU-GM stimulated by a GM-CSF/IL-3 fusion protein in agarose culture medium.

Figure 19:
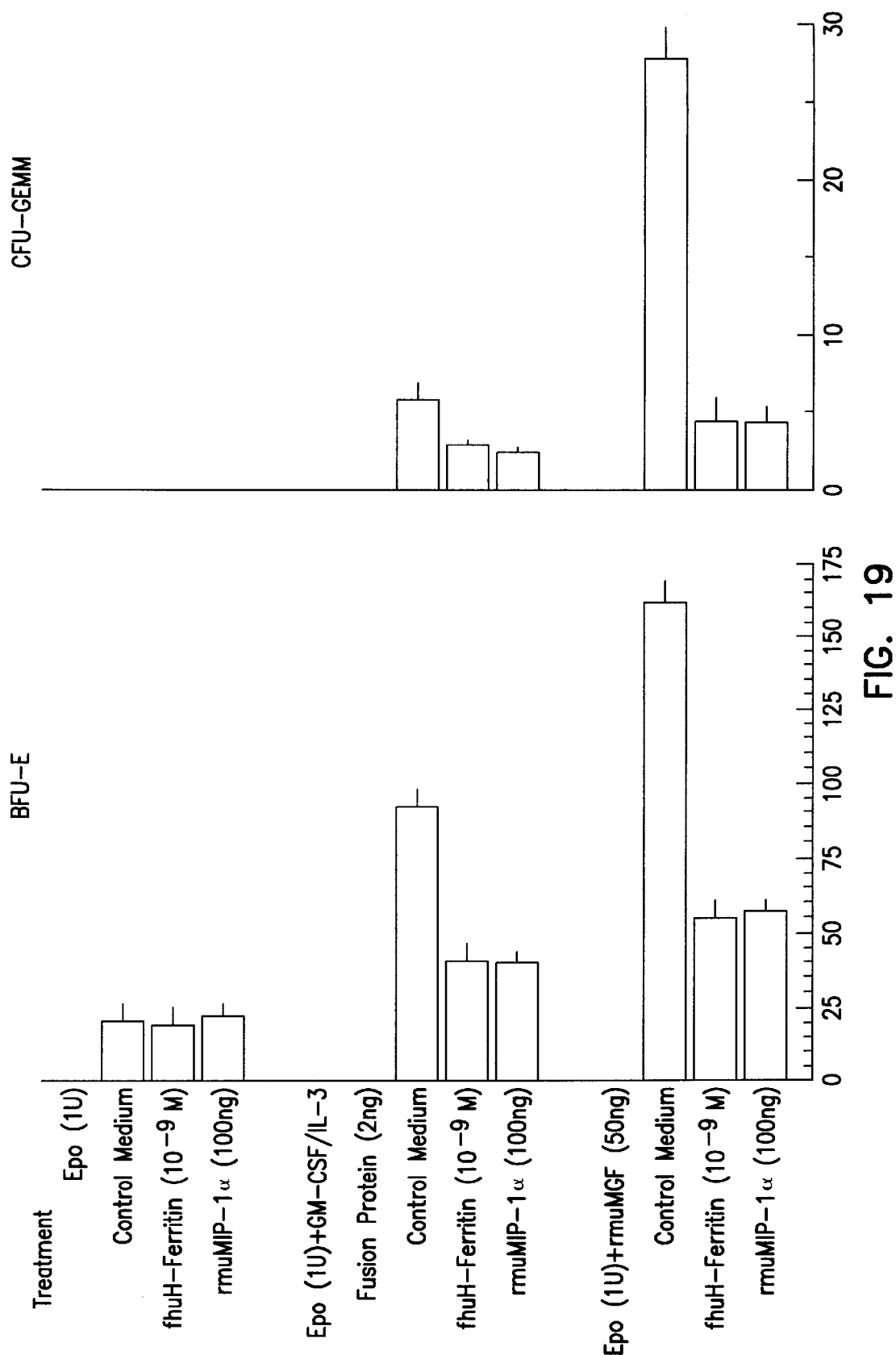

FIG. 19 shows the comparative effects of MIP-1α and H-subunit ferritin on colony formation by NALDT human bone marrow BFU-E and CFU-GEMM stimulated by Epo alone, or in combination with either the GM-CSF/IL-3 fusion protein or MGF.

FIG. 20 shows the influence of MIP-1β hemin, and inactive H-ferritin mutein on suppressive effects of MIP-1α and wildtype H-ferritin on myeloid colony formation.

FIG. 21 shows an RNA Blot Analysis. Five micrograms of poly(A)+ mRNA from L2G25B-transfected C127 clones (C127-L2G25B) were fractionated on a 1.4% formaldehyde-agarose gel, transferred to GeneScreen Plus, and hybridized to $^{32}$P-labeled L2G25B and pMel 14-2 cDNA sequentially. pMel 14-2 was used to compare the amount of mRNA which had been applied in each lane. Numbers on each lane are the C127-L2G25B clone numbers.

FIGS. 22A–C show the expression and purification of rMIPα. FIG. 22A shows an immunoblot analysis using anti-rMIP-1α antibody (1:100). FIG. 22B shows purified protein bands of rMIP-1α. FIG. 22c shows the amino acid sequence determined from purified rMIP-1α.

Figure 23:
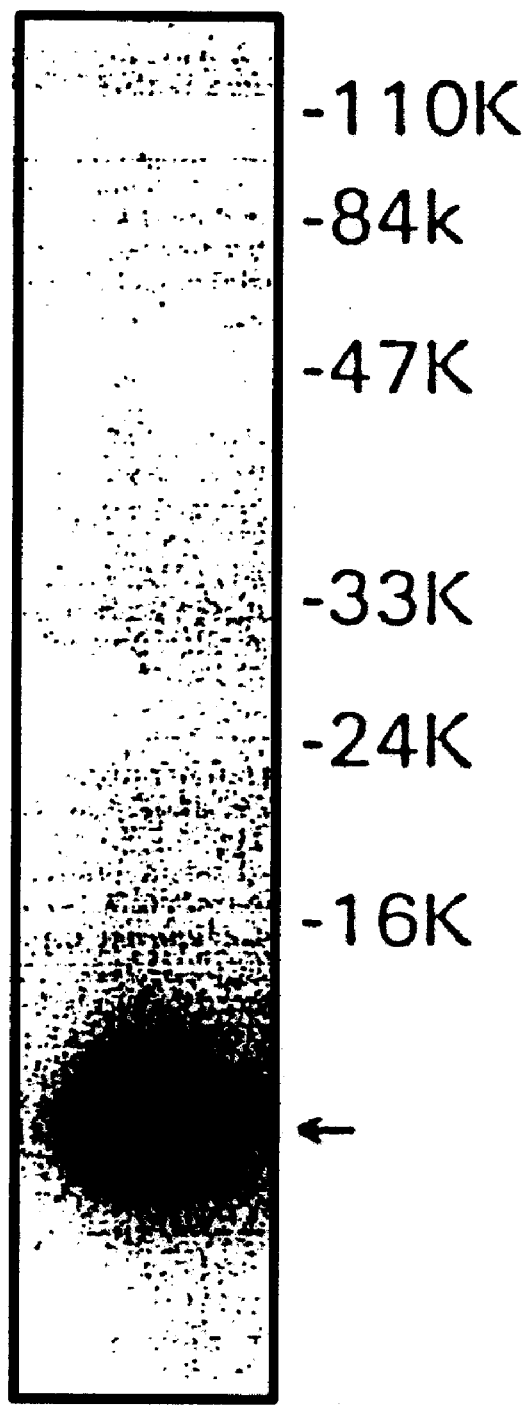

FIG. 23 shows an autoradiograph of pure $^{125}$I-rMIP-1α analyzed by SDS-PAGE.

Figure 24A:
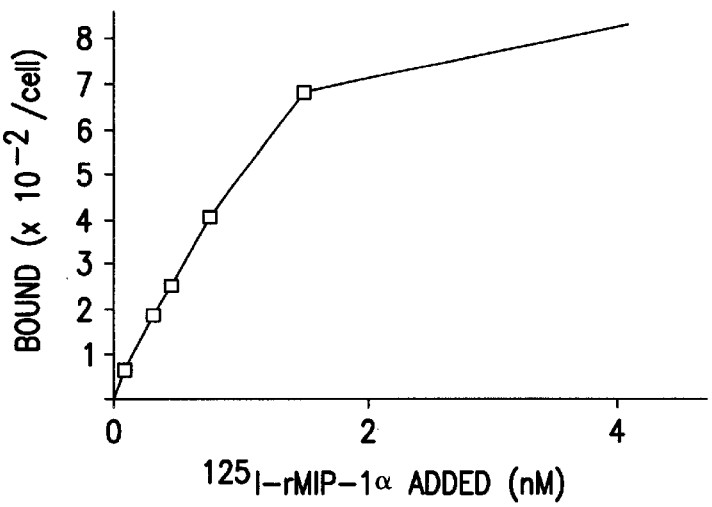
Figure 24B:
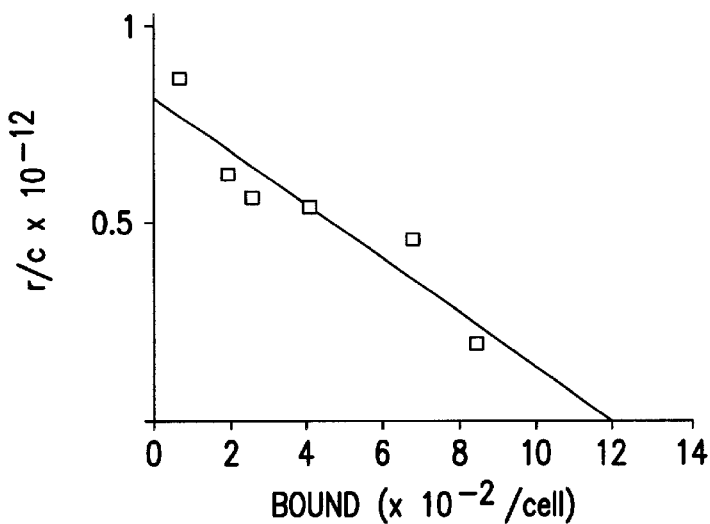
Figure 24C:
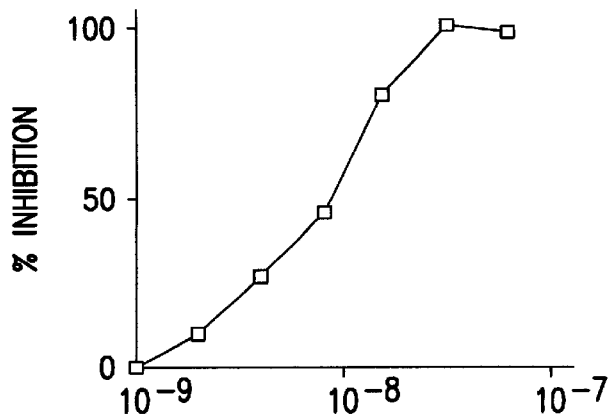

FIGS. 24A–C show a $^{125}$I-rMIP-1α binding curve and Scatchard plot analysis.

Figure 25A:
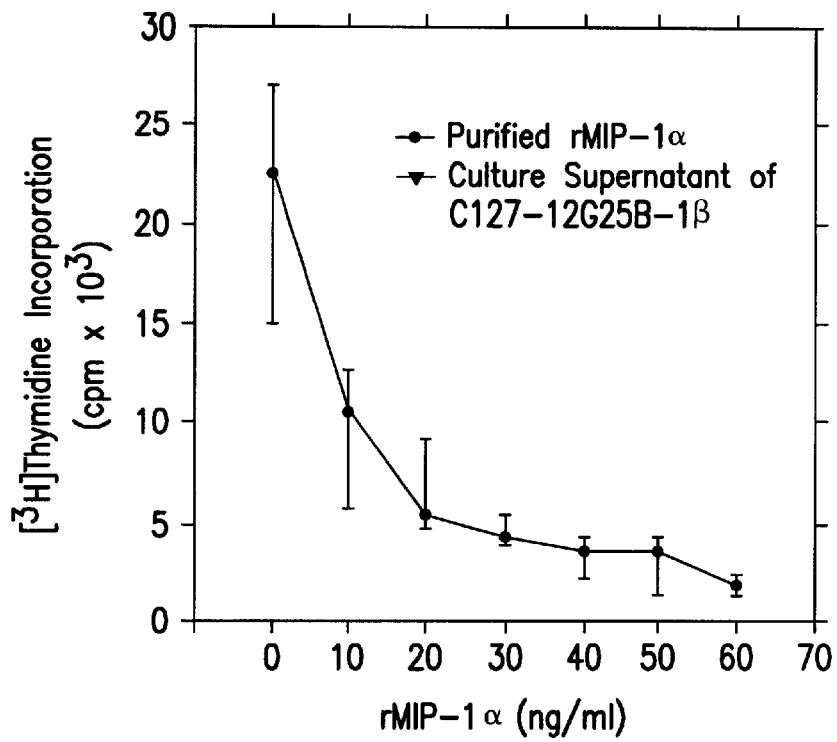
Figure 25B:
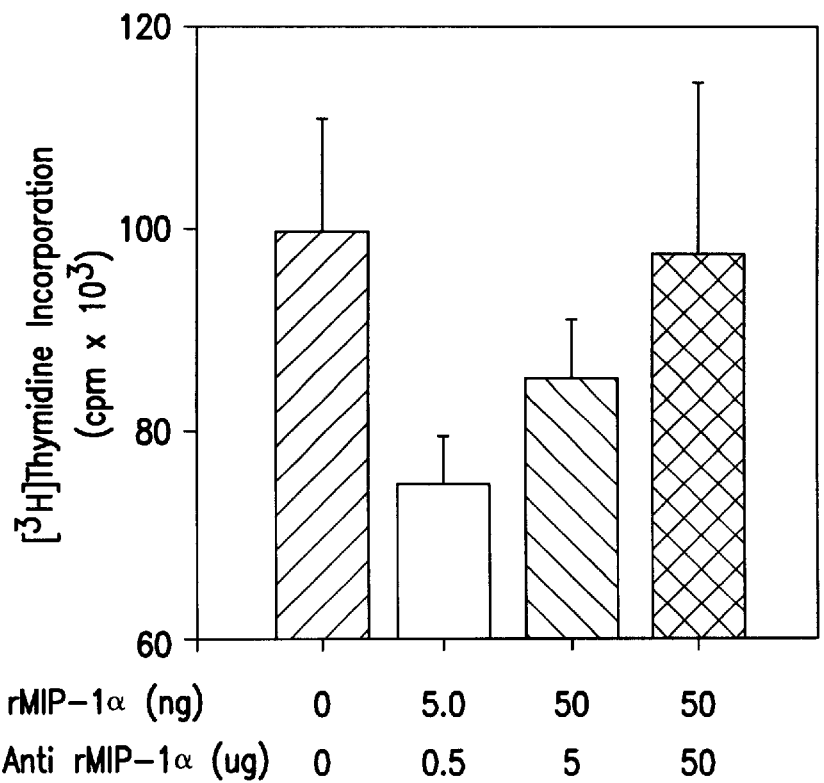

FIGS. 25A–B show an inhibition of CTLL-R8 cell proliferation by rMIP-1α and a blocking of rMIP-1α effect by anti-rMIP-1α IgG.

FIG. 26 shows the influence of varying the dosages of rmuMIP-1α on the cycling rates (percentage of cells in S-phase) of myeloid progenitor cells in the marrow (A) and spleen (B) of C3H/HeJ mice.

FIG. 27 shows the influence of varying dosages of rmuMIP-1α on the absolute numbers of myeloid progenitor cells in the marrow (A) and spleen (B) of C3H/HeJ mice.

FIG. 28 shows a time sequence study of the effects of nnuMIP-1α on the cycling rates (percentage of cells in S-phase) of myeloid progenitor cells in the marrow (A) and spleen (B) of C3H/HeJ mice.

FIG. 29 shows a time sequence study of the effects of rmuMIP-1α on the absolute numbers of myeloid progenitor cells in the marrow (A) and spleen (B) of C3H/HeJ mice.

Figure 30A:
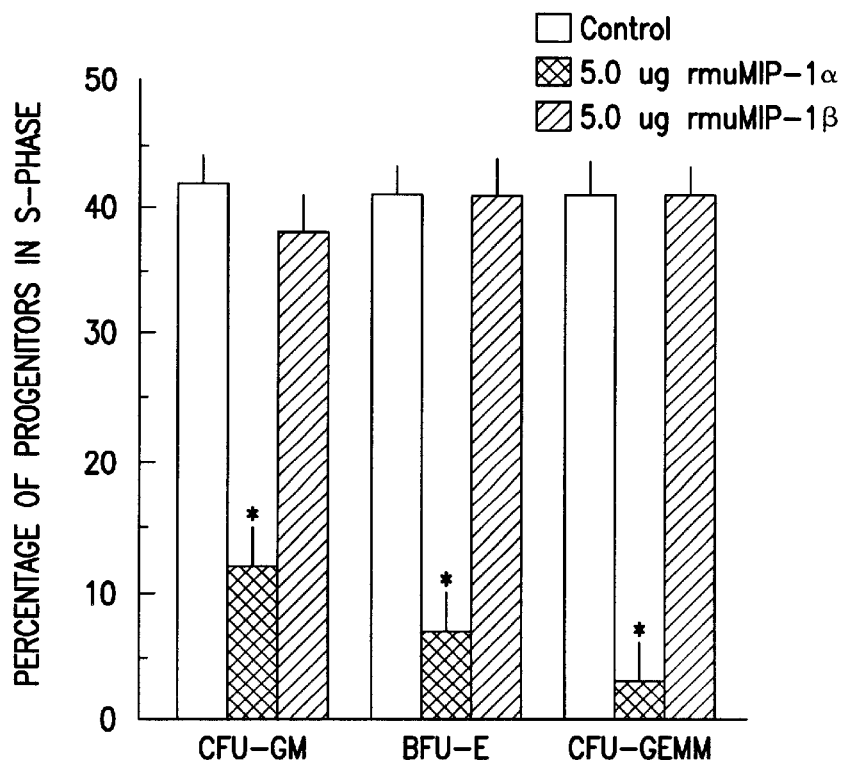
Figure 30B:
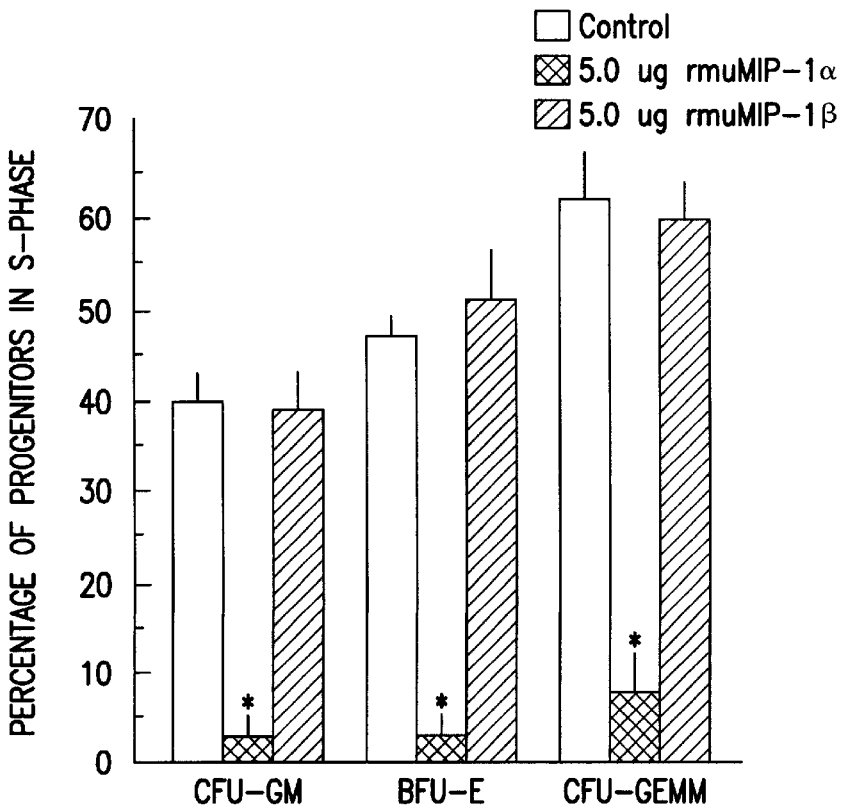

FIG. 30 shows the comparative influence of rmuMIP-1α and nnuMIP-1β on the cycling rates (percentage of cells in S-phase) of myeloid progenitor cells in the marrow (A) and spleen (B) of C3H/HeJ mice.

Figure 31A:
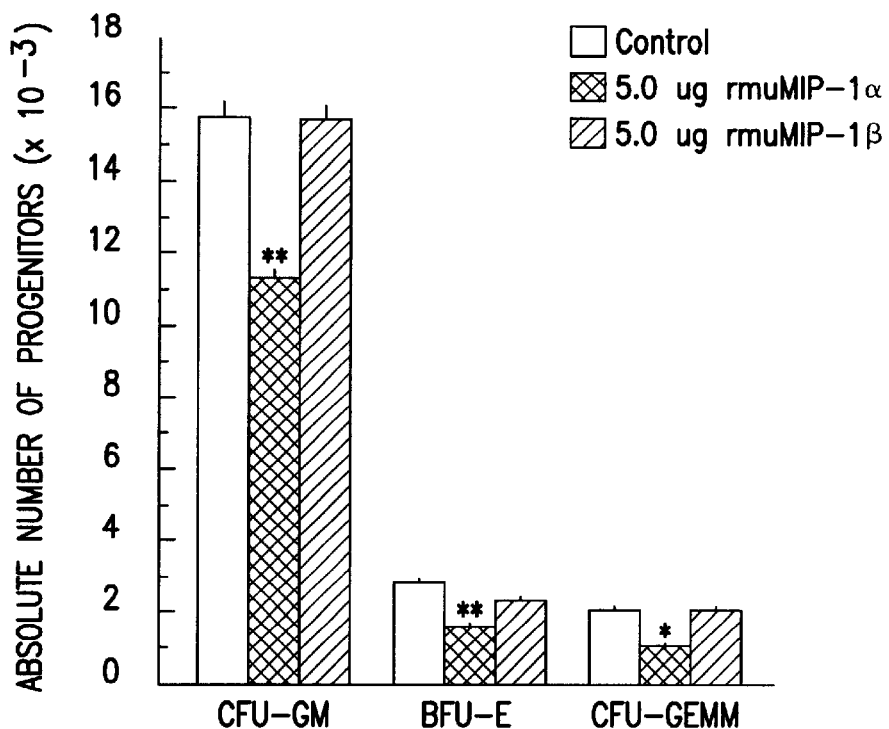
Figure 31B:
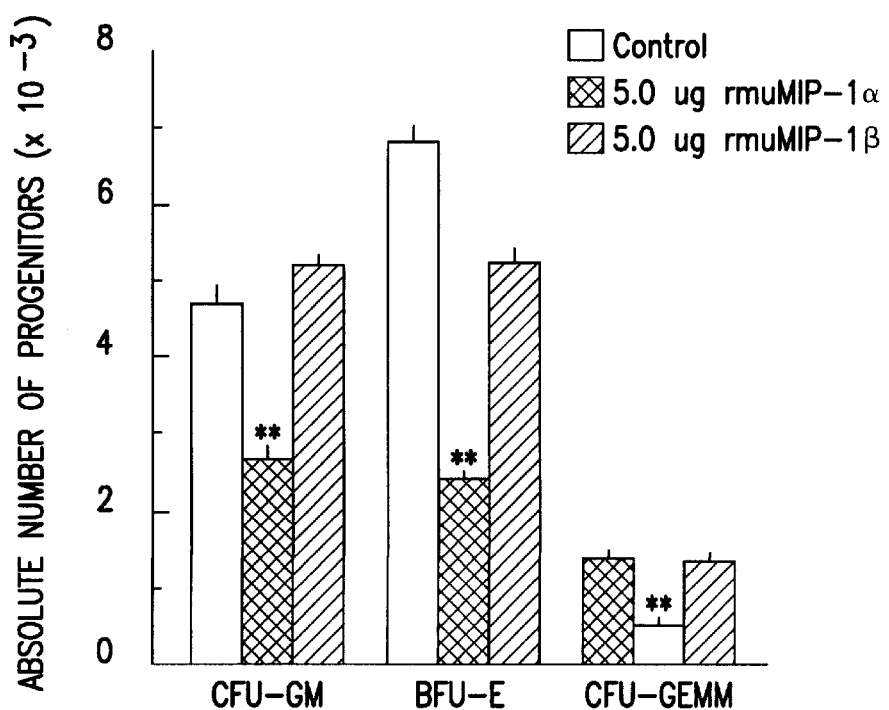

FIG. 31 shows the comparative influence in vivo of rmuMIP-1α and rmuMIP-1β on the absolute numbers of myeloid progenitor cells in the marrow (A) and spleen (B) of C3H/HeJ mice.

Figure 32:
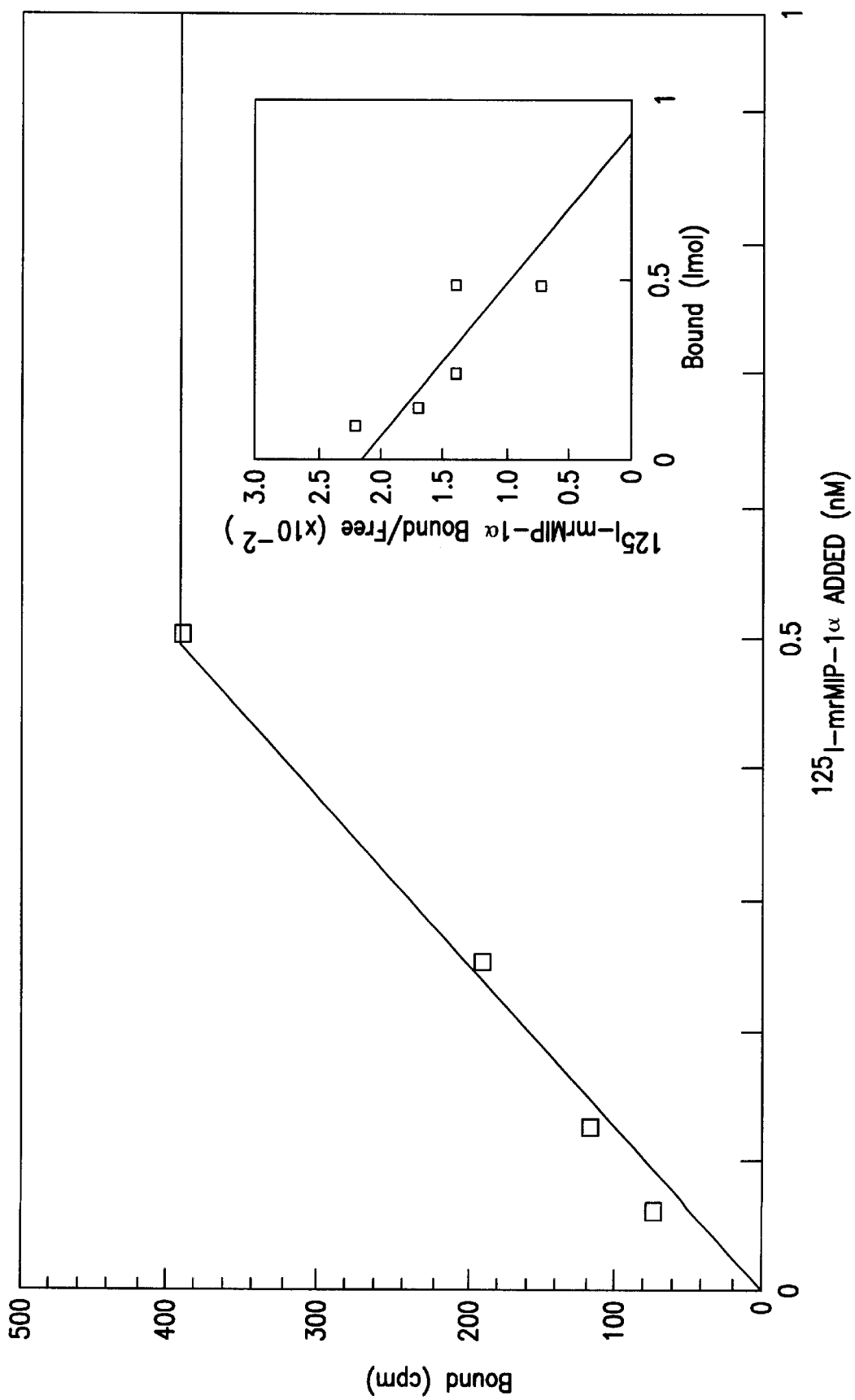

FIG. 32 shows the [$^{125}$I]mrMIP-1α binding curve and Scatchard plot analysis.

Figure 33:
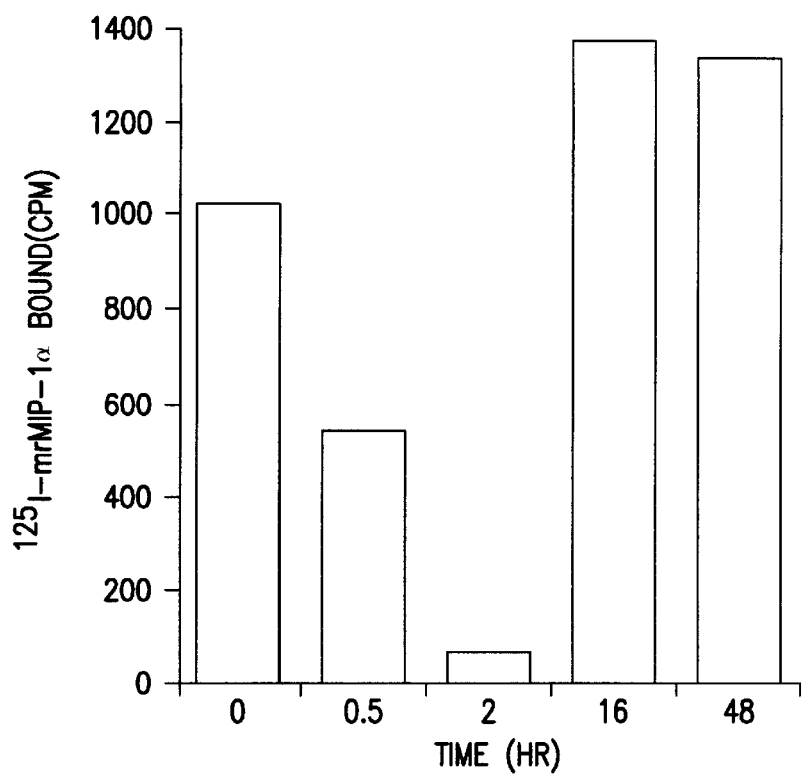

FIG. 33 shows the specific binding of [$^{125}$I]mrMIP-1α to antiCD3 mAb-stimulated splenic T cells.

Figure 34:
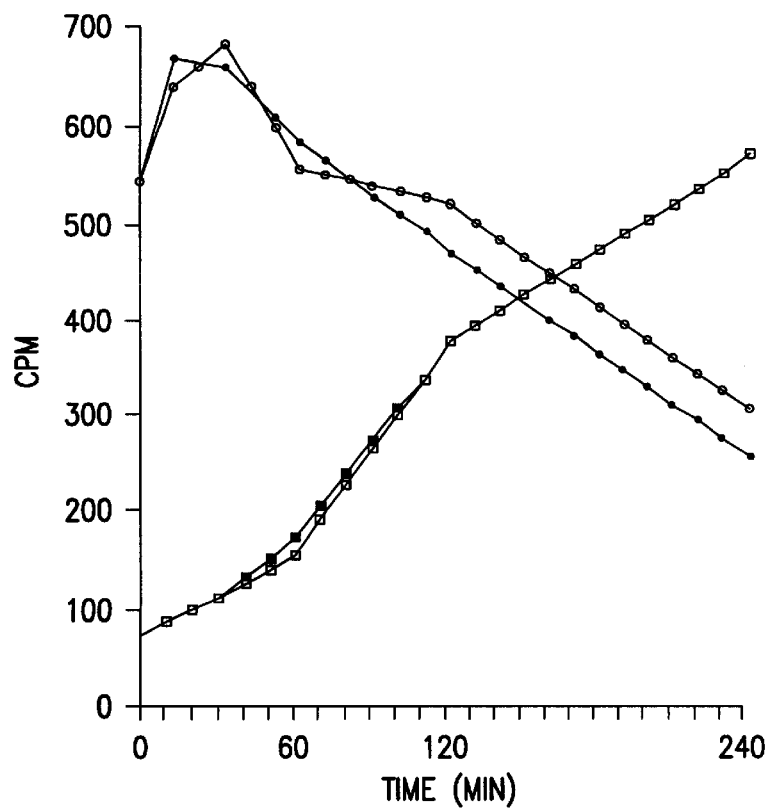

FIG. 34 shows the internalization of MIP-1α receptor in murine splenic T cells.

Figure 35:
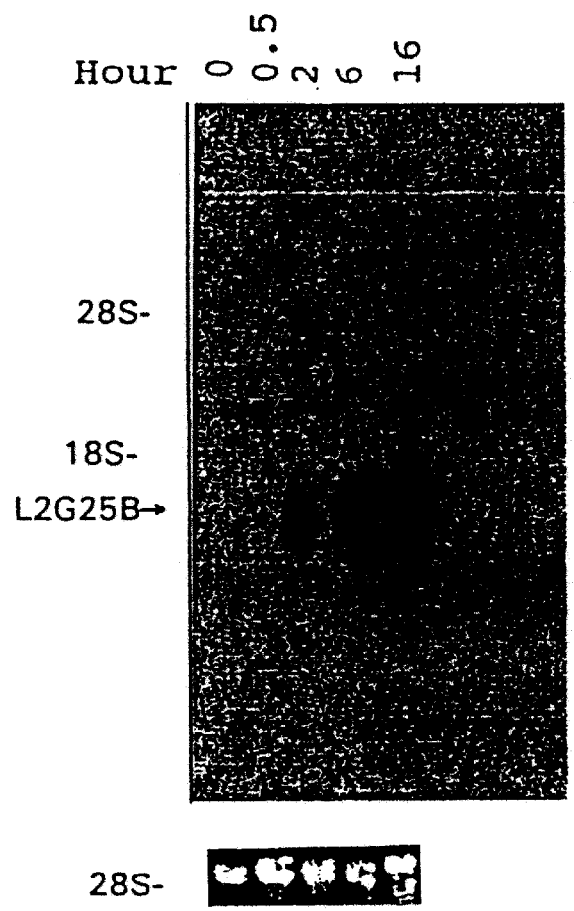

FIG. 35 shows a northern analysis of mrMIP-1α mRNA.

Figure 36:
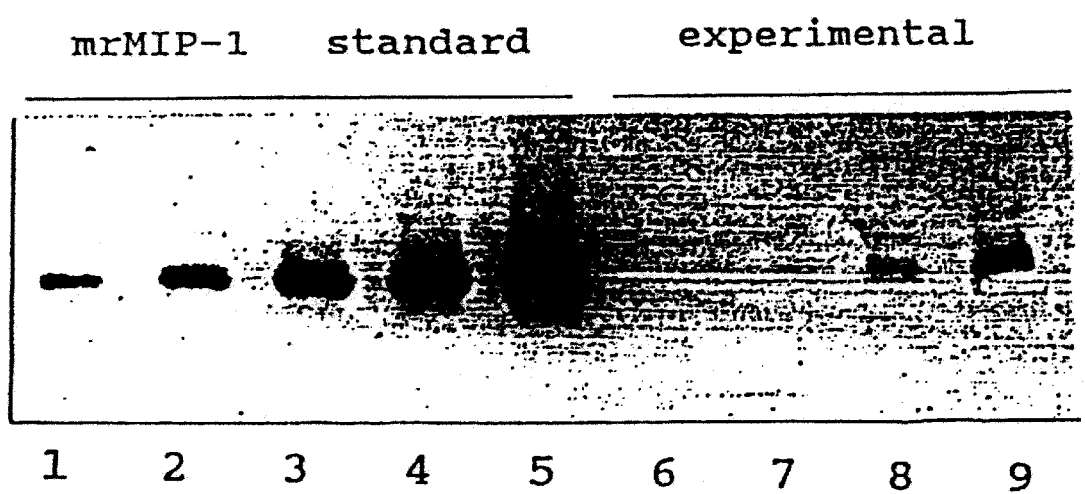

FIG. 36 shows a western blot analysis of mMIP-1α protein secreting in supernatant after antiCD3 mAb-stimulation.

Figure 37A:
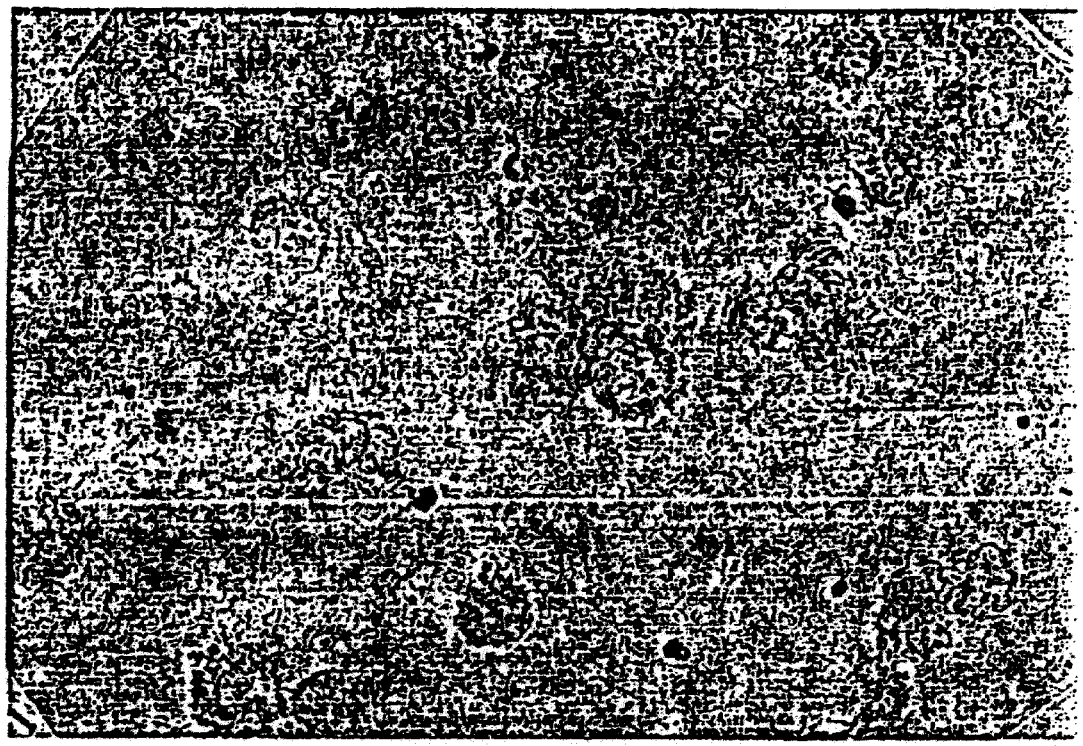
Figure 37B:
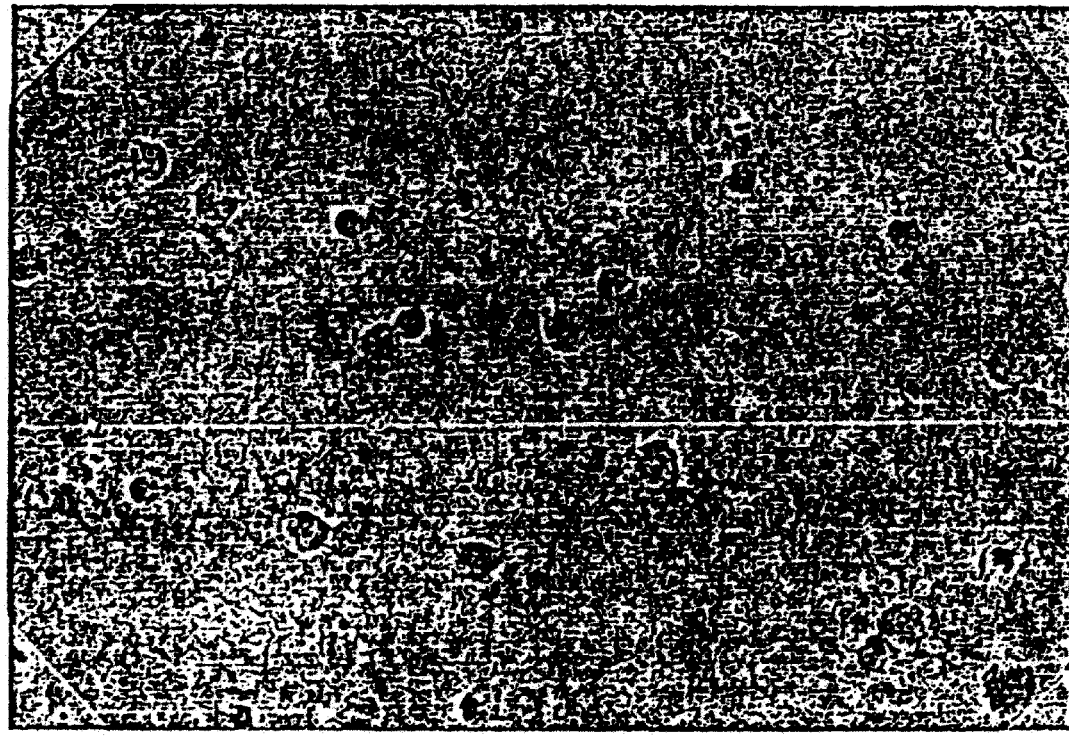

FIG. 37 shows the detection of mrMIP-1α receptor with biotinylated mrMIP-1α.

FIG. 38 shows the inhibition of murine splenic T cell proliferation by mrMIP-1α.

Figure 39:
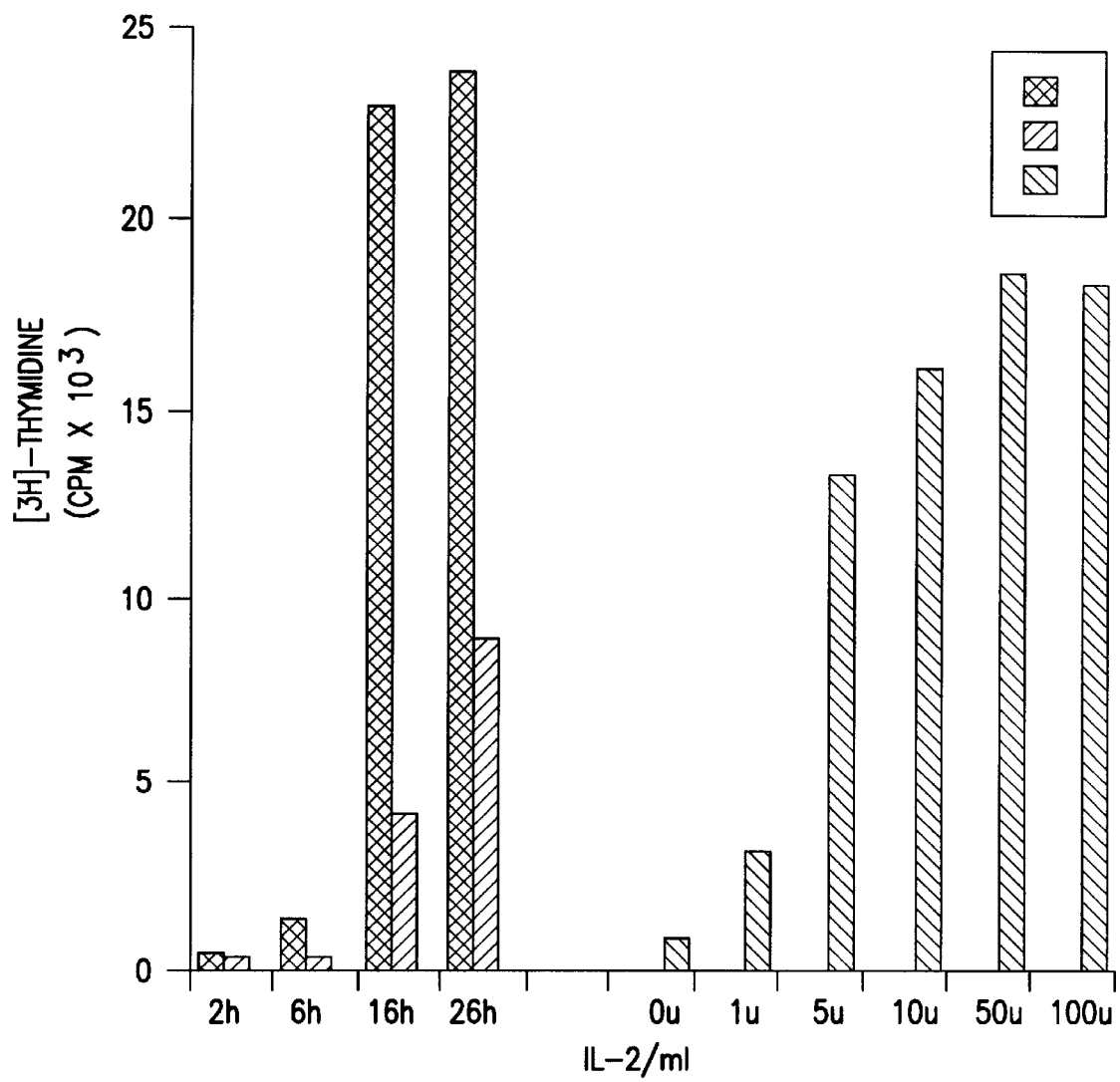

FIG. 39 shows the effect of mrMIP-1α on antiCD3 mAb-mediated IL-2 secretion for 30 min prior to stimulation.

Figure 40:
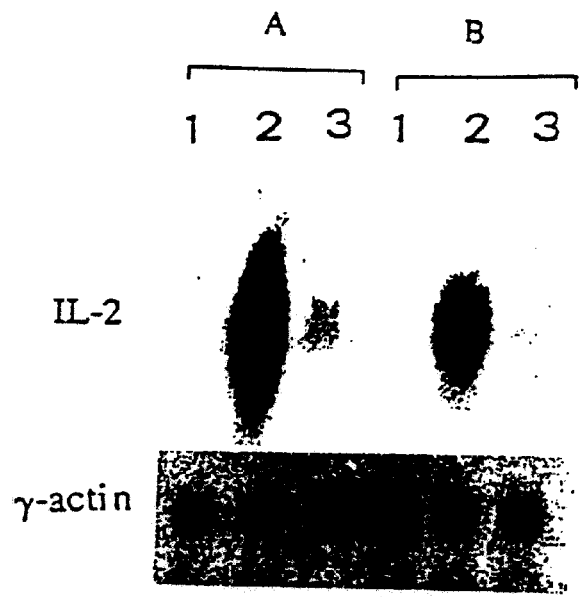

FIG. 40 shows the measured in the culture medium by testing the growth of IL-2 dependent CTLL-2 cell line.

Figure 41:
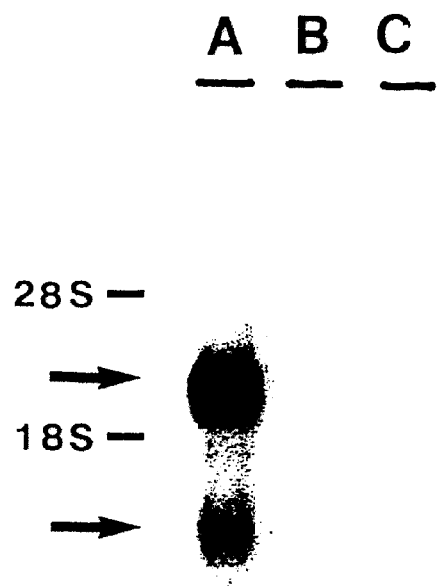

FIG. 41 shows the expression of 4-1BB on RNA in CTLL-R8.

Figure 42:
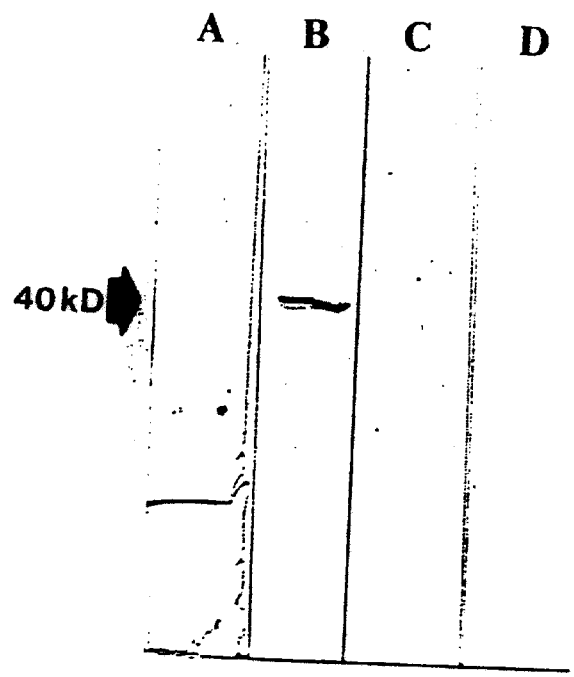

FIG. 42 shows an immunoblot analysis of CTLL-R8 cell lysates with anti-4-1BB-0 serum.

Figure 43:
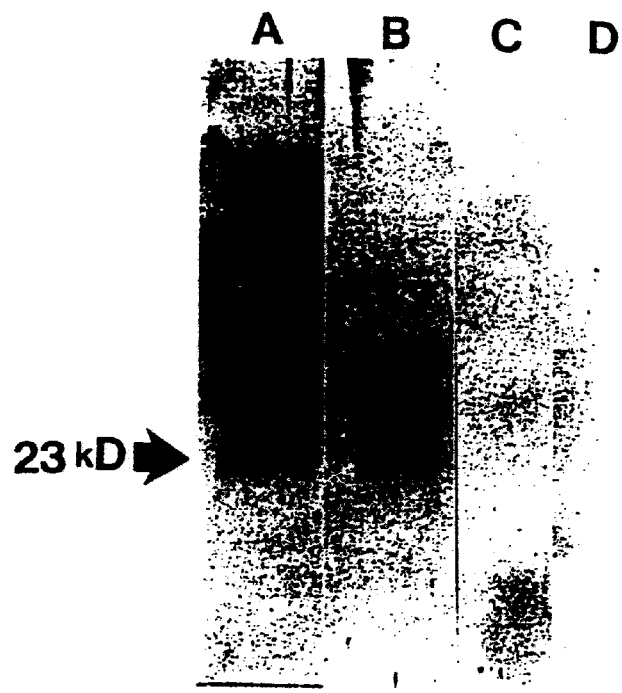

FIG. 43 shows an immunoblot analysis of the 4-1BBPs.

FIG. 44 shows representative histograms of IgG fraction of anti-4-1BB-O related fluorescence intensity of CTLL-R8 cells.

Figure 45:
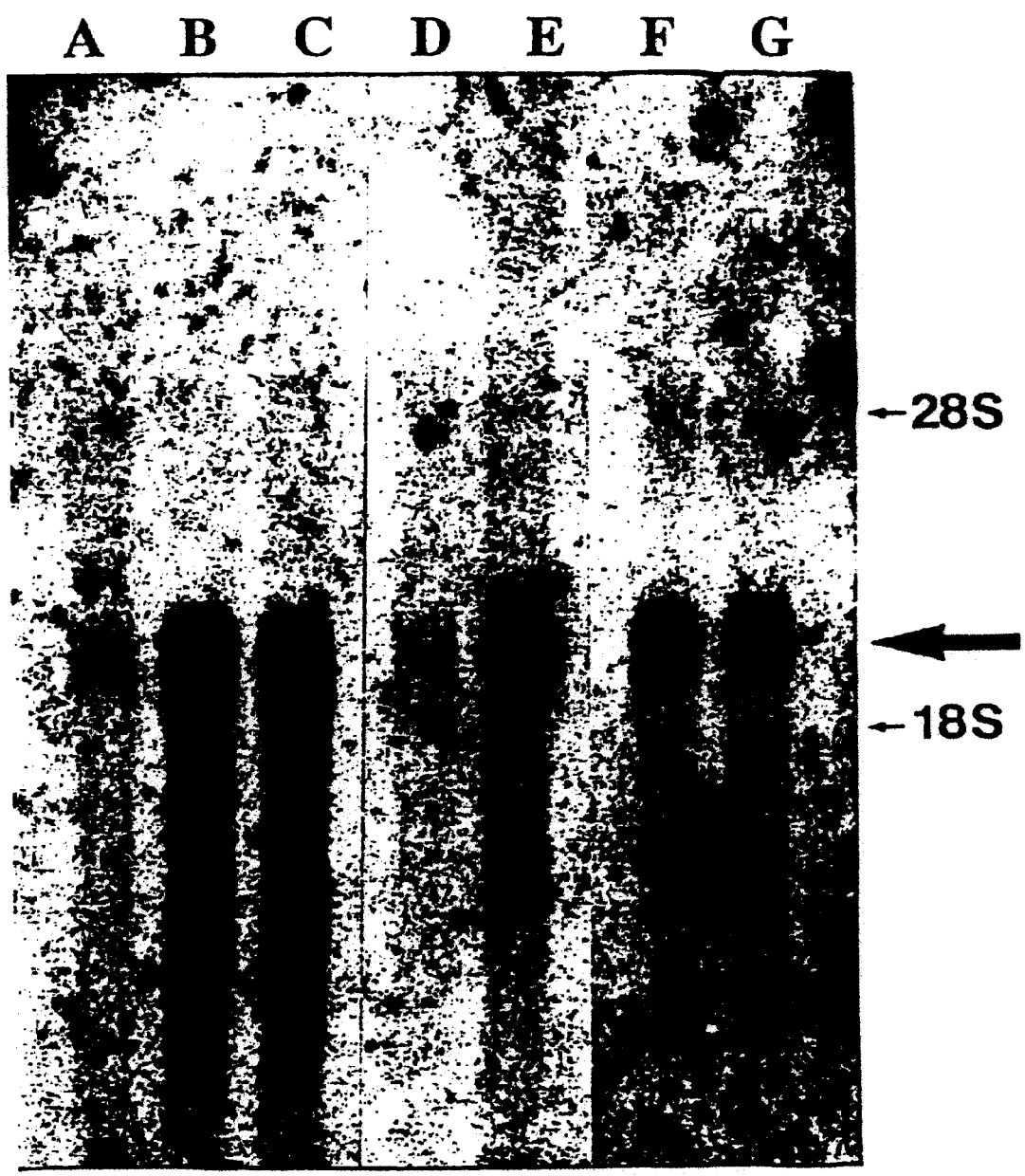

FIG. 45 shows the expression of 4-1BB RNA in mouse tissues.

Figure 46:
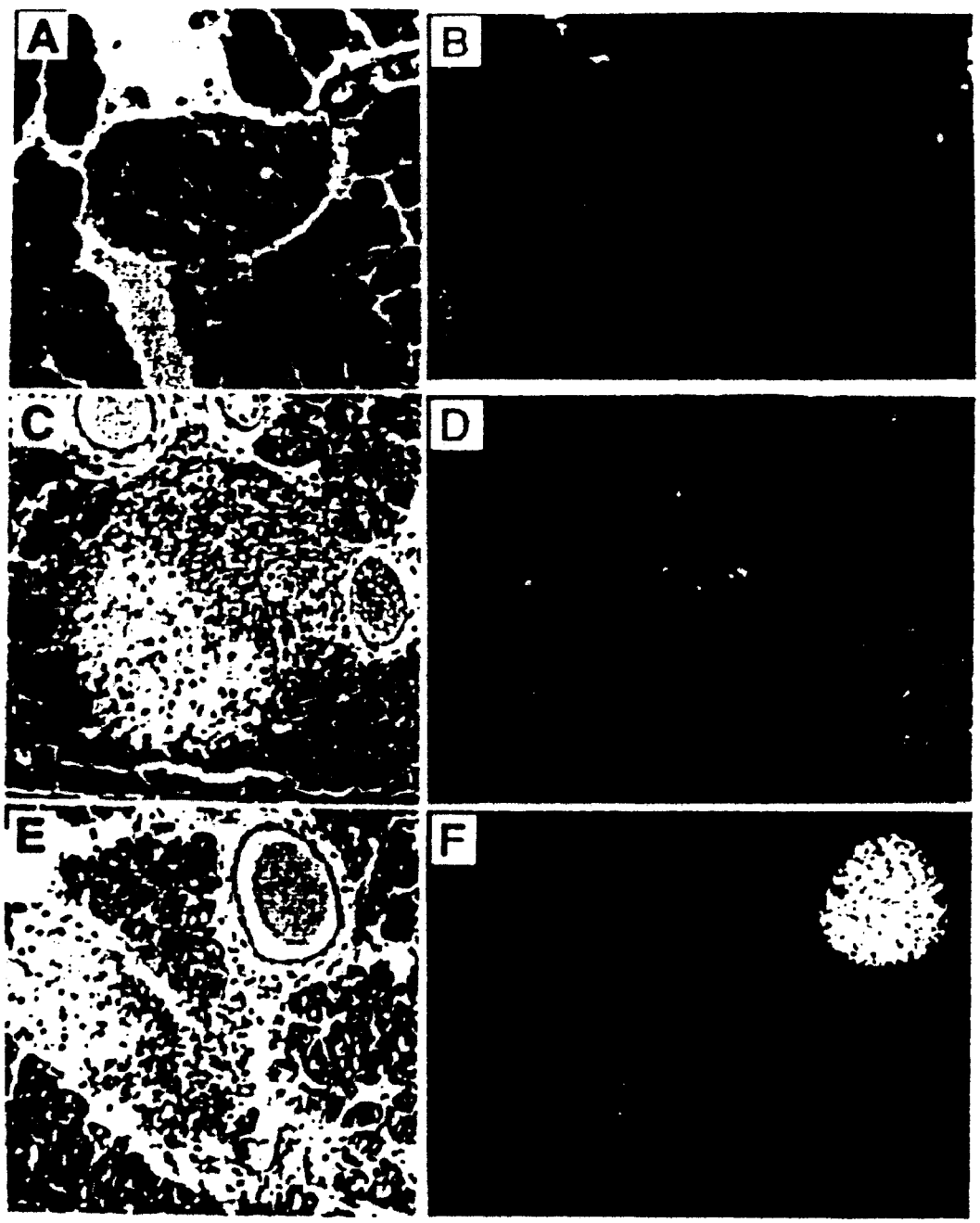

FIG. 46 shows the histology of NOD mouse pancreata and immunofluorescent staining of islets showing different stages of insulitis.

FIG. 47 shows a comparison of the 4-1BBP amino acid sequence with the amino acid sequence in sina of Drosophila and DG17 of Dictyostelium.

Figure 48:
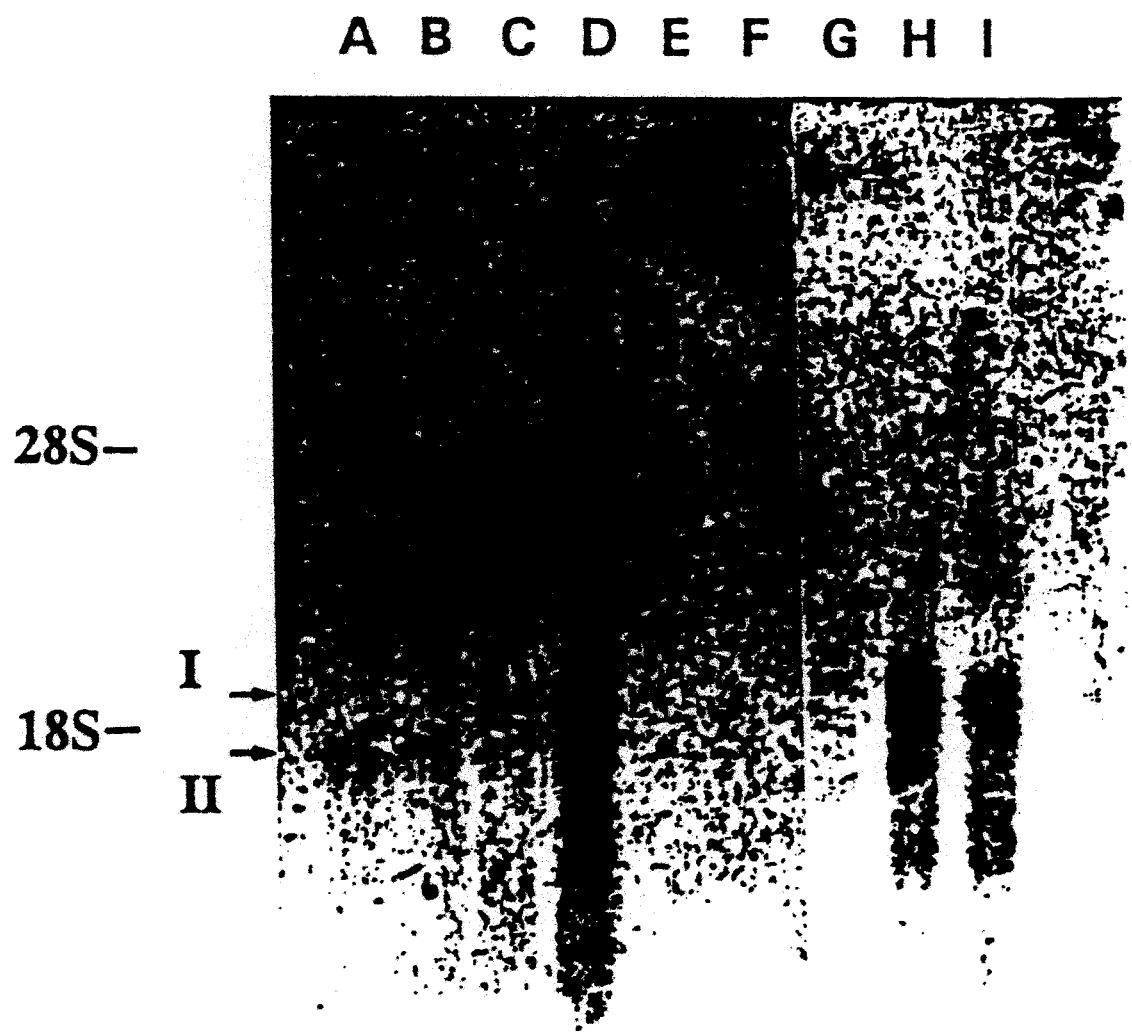

FIG. 48 shows a northern blot analysis of kidney and brain RNA.

Figure 49:
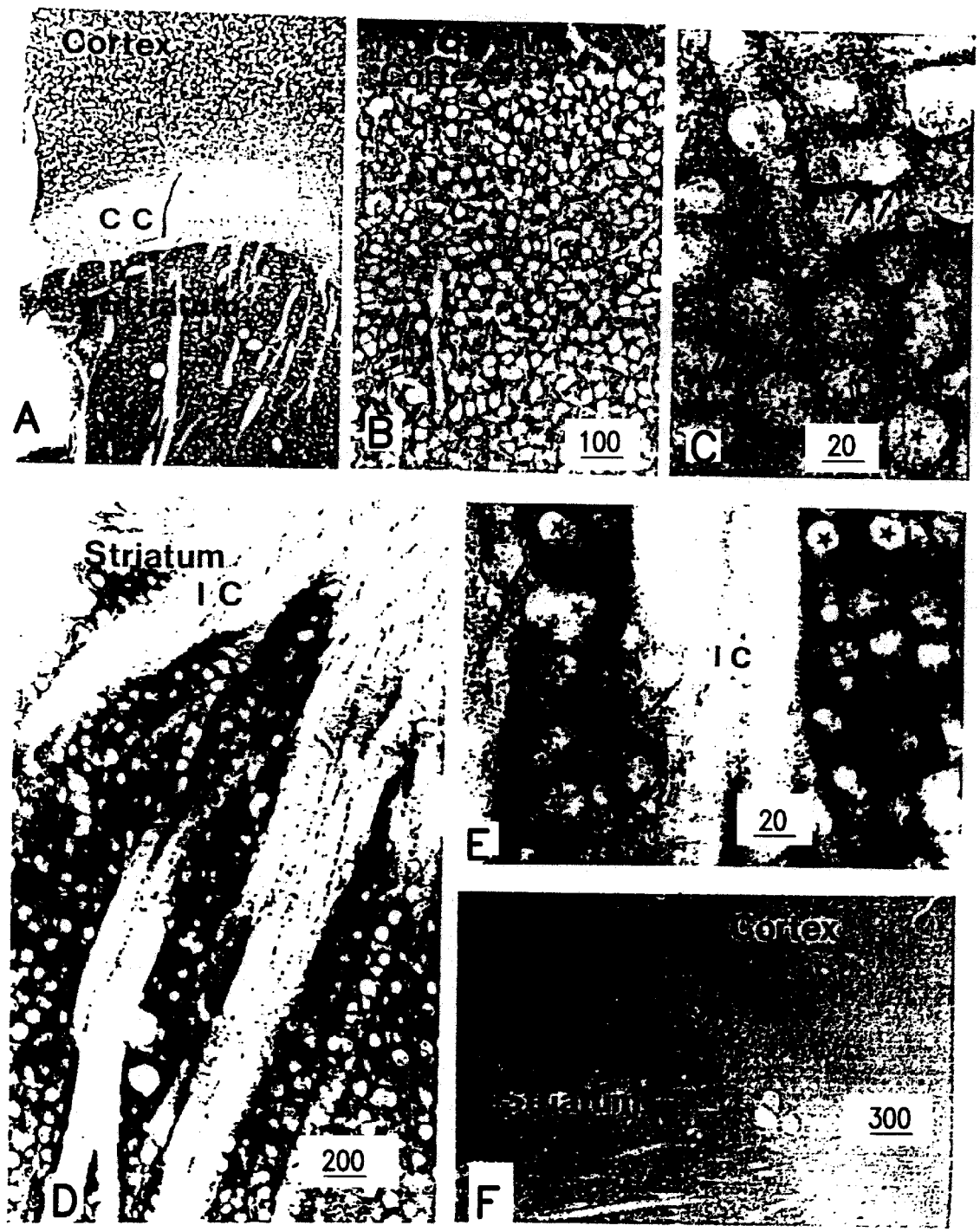

FIG. 49 shows 4-1BB immunostaining in the cortex (a, b, and d) striatum (a, d, and e) at progressively enlarged magnifications.

Figure 50:
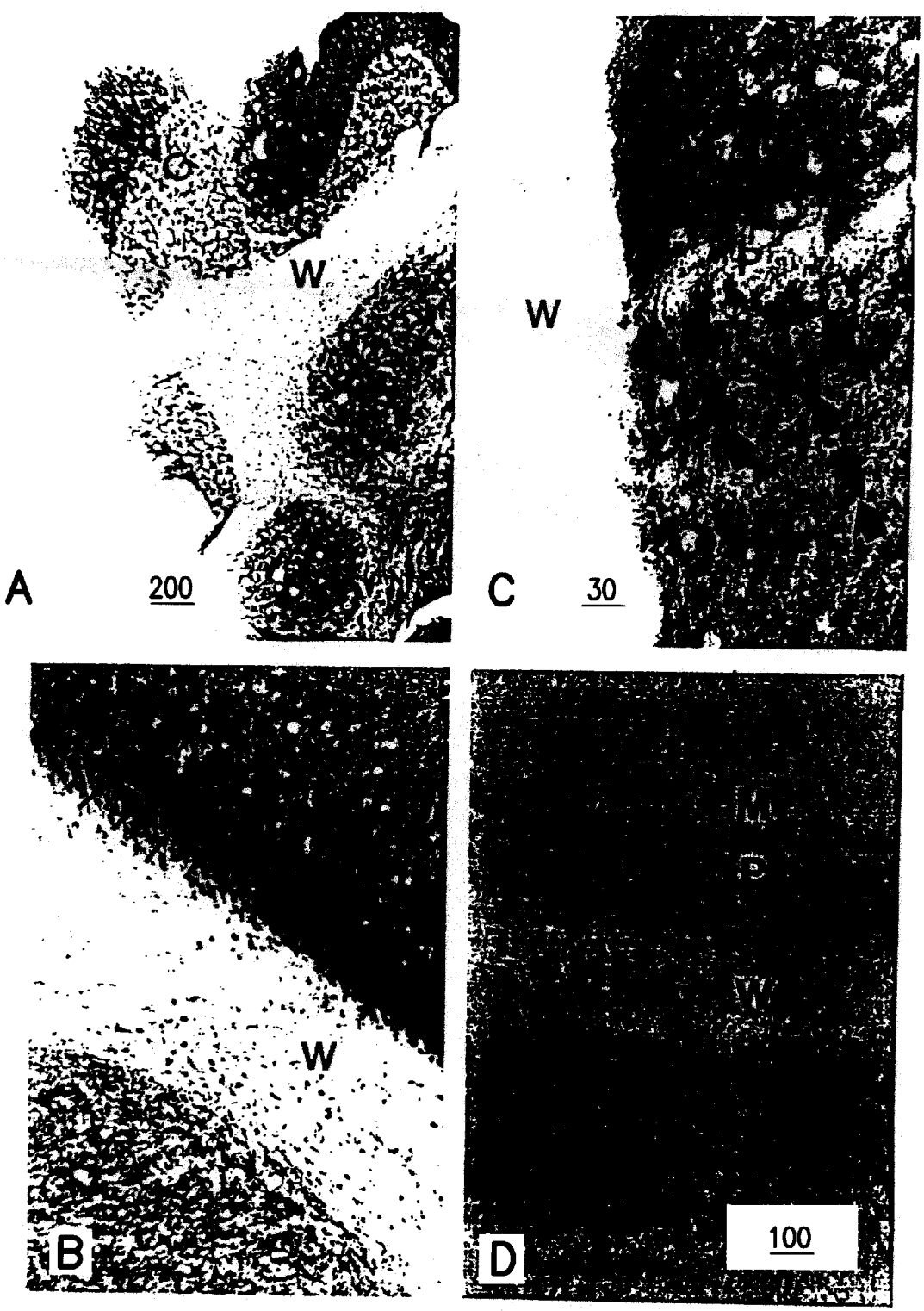

FIG. 50 shows distinct 4-1BB immunopositive reaction in the cerebellum at three progressively enlarged magnifications (a, b, and c).

DETAILED DESCRIPTION

In the following detailed description a successive series of studies are presented which characterize L2G25B (MIP-1α) and 4-1BB. References are made to known procedures and studies, as well as published work of the applicants. These publications are incorporated herein by reference for clarity and listed in an appendix included at the end of this detailed description.

The following abbreviations are used herein: CTL, cytolytic T lymphocyte; HTL, helper T lymphocyte; LGL, large granular lymphocytes; NK, natural killer cells; SDS, sodium dodecylsulfate; SSC, 150 mM sodium chloride/15 mM sodium citrate, pH 7.0; TPA, 12-0-tetradecanoylphorbol-13-acetate. Th, helper T lymphocytes; IL-2, interleukin 2; IL-3, interleukin 3; rIL-2, recombinant IL-2; CSF-GM, granulocyte/macrophage colony-stimulating factors; cRNA, complementary RNA; ss, single-stranded; ds, double-stranded; TCR, T-cell antigen receptor; PTA, phorbol 12-tetradecanoate 13-acetate; r, recombinant; mu, murine; hu, human; MIP, macrophage inflammatory protein; BFU-E, burst forming unit-erythroid, an erythroid progenitor cell; CFU-GEMM, colony forming unit-granulocyte erythroid macrophage, megakaryocyte, a multipotential progenitor cell; CFU-GM, colony forming unit-granulocyte macrophage, a granulocyte-macrophage progenitor cell; CFU-S, colony forming unit-Spleen, a multipotential stem cell; H-ferritin, the heavy chain subunit form of ferritin; MGF, mast cell growth factor, a c-kit ligand; CSF, colony stimulating factors; G, granulocyte; M, macrophage; Epo, erythropoietin; IL, interleukin; LD, low density; NALDT, non-adherent low density T-lymphocyte depleted; PMSF, phenylmethylsulfonyl fluoride; PBS, phosphate buffered saline; MIP-1α-R, MIP-1α receptor; rMIP-1α, recombinant MIP-1α protein; nMIP-1α, native macrophage inflammatory protein-i; AcNPV, *Autographa californica* nuclear polyhedrosis virus; SDS, sodium dodecyl sulfate; LPS, lipopolysaccharide; ConA, concanavalin A; DTT, dithiothreitol; mAb, monoclonal antibody.

Initial Isolation and Sequencing of L2G25B (MIP-1α) & 4-1BB

Materials and Methods

Cells cloned murine CTL L3 cells (1), are thy-1,2$^+$, Lyt-2$^+$, LFA-1$^+$, LeT4$^-$ and H-2L$^d$ reactive. Cloned murine HTL L2 cells (2) are Thy-1,2$^+$, LFA-1$^+$, Lyt-2$^-$, LeT4$^+$ and Mls$^{a/d}$ reactive.

Methods of isolating and maintaining the cloned helper T lymphocytes (Th), L2, and the cloned cytolytic T lymphocytes (CTL), L3, have been described in the above-identified publication. To stimulate the cloned T cells, we resuspended them at 10$^6$–10$^7$ cells per ml and cultured them with Con A (Pharmacia) at 10 ug/ml for L2 cells or 2 ug/ml for L3 cells or human recombinant IL-2 (rIL-2; Cetus) at 10$^2$14 10$^3$ units/ml. Immobilized clonotypic monoclonal antibody 384.5, which reacts with the TCR of L3 cells (2), was used to stimulate L3 cells.

Mouse thymoma cells, EL4, and mouse B-cell lines, A20.2j and K46, were maintained in RPMI 1640 medium containing 5% fetal calf serum. EL4 cells were stimulated with phorbol 12-tetradecanoate 13-acetate (PTA; 10 ng/ml) for up to 20 hr, monitoring the stimulation by IL-2 assay (3).

cDNA Libraries

RNAs of L2 and L3 cells that were stimulated by Con A for 14 hr, were extracted (4) and poly(A)$^+$ mRNA was purified on an oligo(dT)-cellulose column (5). Double-stranded (ds) cDNA was synthesized from the poly(A)$^+$ mRNA (6). The cDNA was methylated at EcoRI sties, EcoRI linkers were ligated to cDNA, and then the cDNA was enriched for molecules larger than 250,000 daltons by passage over Bio-Gel A-150m columns. The cDNAs were inserted into the EcoRI Site of gt10 bacteriophage cloning vector (7).

cDNA Probe

Six micrograms of poly(A)$^+$ mRNA was denatured with 10 mM methylmercuric hydroxide and incubated in a buffer containing 100 mM Tris HCl at pH 8.3, 50 mM KCl, actinomycin D at 50 mg/ml, 30 mM 2-mercaptoethanol, 10 mM MgCl$_2$, (dt$_{12-18}$ at 5 ug/ml, 0.5 mM each of dATP, dCTP, and dGTP, 0.01 mM dTTP, 0.001 mM [α-$^{32}$P]dTTP (3000 Ci mmol$^{-1}$; 1 Ci=37 GBq), and reverse transcriptase from avian myeloblastosis virus at 1000 units/ml at 46° C. for 30 min. Single-stranded (ss) cDNA was freed from its template RNA by incubation in 200 mM NaOH/10 mM EDTA at 60° C. for 30 min and passed over a 4-ml column of Sephadex G-100. The specific activity of the probe was usually ~1.6–2.0×10$^8$cpm/ug of cDNA.

Subtracted cDNA Probe

The ss cDNA prepared from L2 RNA was hybridized to a R$_o$t of 1200–1500 (mol of nucleotide per liter)×sec with poly(A)$^+$ RNA of A20.2j in 0.41 M sodium phosphate buffer, pH 6.8, containing 0.1% NaDod-SO$_4$ and 1 mM EDTA, in a volume of 25–50 ul. The ss cDNA fraction was collected by chromatography through a hydroxylapatite column as recommended by the vendor (Bio-Rad). Seven percent of input cDNA was recovered in the ss fraction and used for a second round of hybridization to A20.2j poly(A)$^+$ mRNA to an equivalent R$_o$t of 500 (mol/liter)×sec. Approximately 93% of initial input radioactivity was recovered. Starting with 6 ug of poly(A)$^+$ mRNA, approximately 5.5×10$^6$ cpm was obtained as a probe.

DNA and RNA Blot Hybridization

Recombinant phage DNA was prepared (8) and digested with EcoRI. DNA fragments were transferred to GeneScreen Plus membranes (New England Nuclear) and hybridized with ss cDNA probes (9). RNA was run on 1.2% formaldehyde denaturing agarose gel (10) and transferred to Gene-Screen Plus. Probes for RNA hybridization were prepared form gel-purified cDNA inserts by the random priming method (11). Total cytoplasmic RNA of poly(A)$^+$RNA were fractionated on 1.2% agarose-formaldehyde gels and transferred to GeneScreen Plus (NEN, Boston, MA). Gel-purified cDNA inserts were [$^{32}$-P]-labeled by nick translation and used as probes. When a Northern blot of GeneScreen Plus was used multiple times for hybridization, the previous probe was removed by treating the membrane in 10 mM Tris-HCl (pH 7.0) and 0.2% SDS at 85° C. for 1 hr.

High molecular weight DNA of mouse spleens was prepared as described previously (12). Endonuclease digests of DNA were electrophoresed in 0.8% agarose gel at 4° C. The DNA was denatured, and transferred to GeneScreen Plus as described by Southern (13). The blot was hybridized with [$^{32}$P]-labeled cDNA inserts.

L2 cells were stimulated with concanavalin A (10 ug/ml) for 14 hr, at a cell concentration of 10$^6$–10$^7$/ml. L3 cells were stimulated with concanavalin A (2 ug/ml) for 14 hr, at a cell concentration of 2.5×10$^6$/ml. Mouse thymoma EL-4 cells (14) were stimulated with 12–0-tetradecanoylphorbol-13-acetate (TPA, 10 ng/ml) at a cell concentration of 1.0× 10$^6$/ml for 20 hr; stimulation was monitored by IL-2 assay (3). B cell lymphoma K46 (15), and rat NK cell LGL (16) were not stimulated with any of above reagents.

Figure 1A:
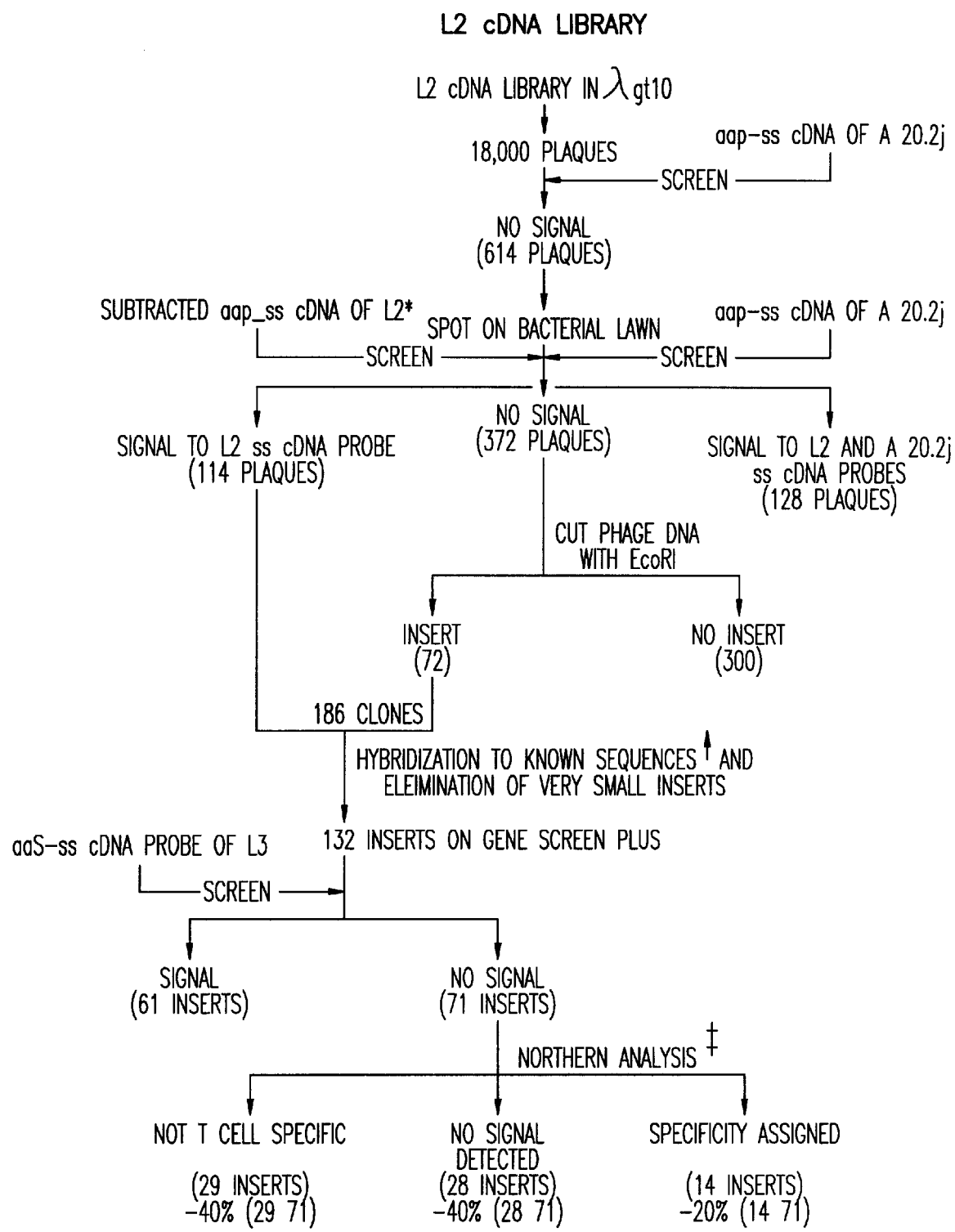
FIGS. 1a and 1b are flow sheets of the present inventor's approach to identifying L2 (helper T lymphocyte) specific and L3 (Cytolytic T lymphocyte) specific cDNA clones.
Figure 1B:
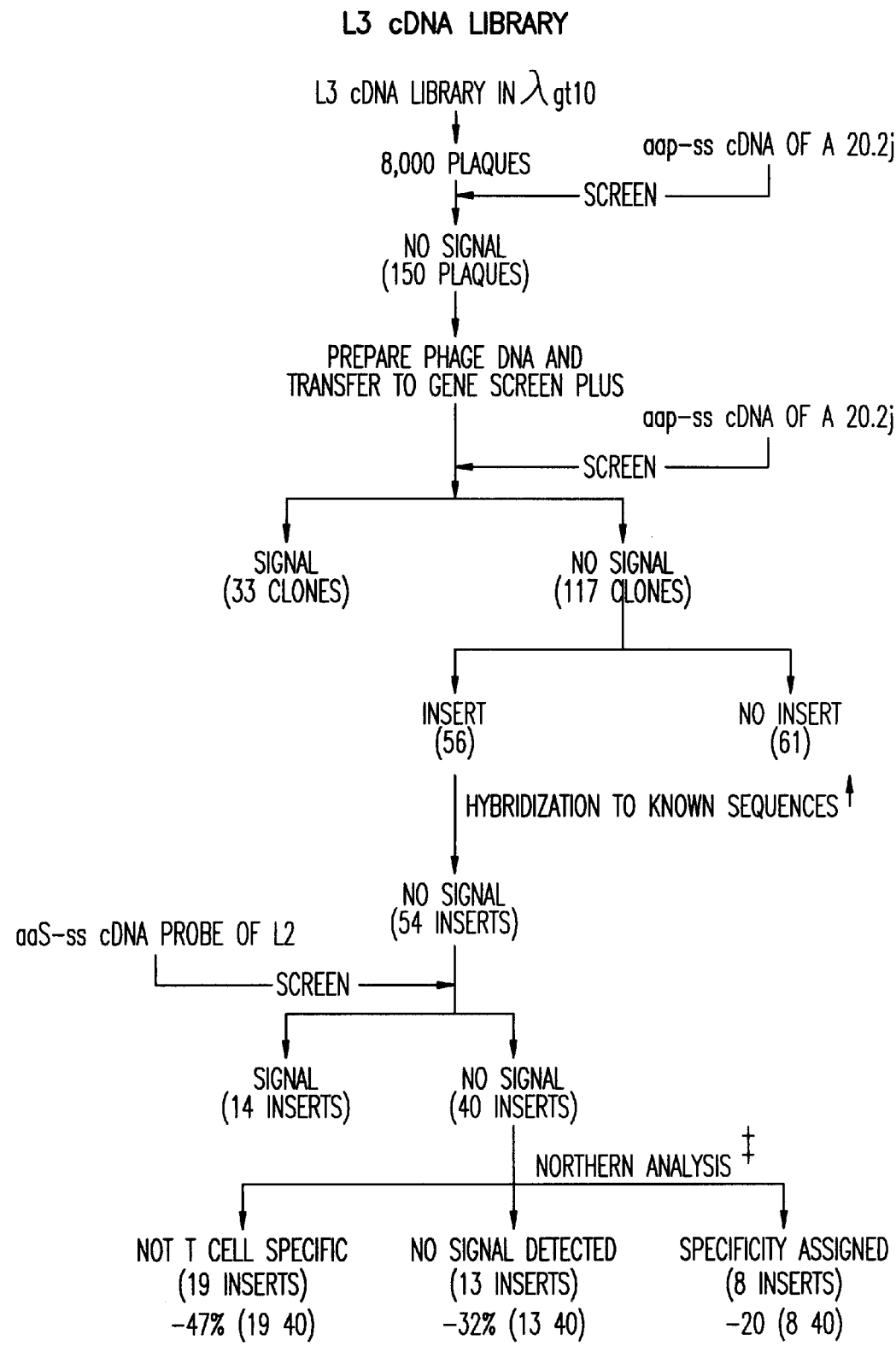

FIGS. 1a and 1b are flow sheets of the present inventor's approach to identify L2-specific and L3-specific cDNA clones. Therein: 1) the * means that preparation of subtracted L2 cDNA probe is described in Materials and Methods; 2) the + means the probes of known sequences were prepared for cDNAs of granulocyte/macrophage colony-stimulating factors (CSF-GM), interleukin 3 (IL-3), IL-2, TCR α-chain, TCR β-chain, c-myc, and c-fos; 3) ++ means the insert of each negative recombinant phage DNA was gel-purified and used as a probe for RNA blot hybridization ("Northern") analysis of K46, unstimulated or PTA-stimulated EL4, large granular lymphocytes (LGL), and unstimulated or Con A-stimulated L2 and L3. The [$^{32}$P]-labeled cDNA probe, prepared from poly(A)$^+$ mRNA of A20.2j, was used to screen the library. The total cDNA probe could detect a clone corresponding to 0.02–0.05% of the test mRNA (17). Of 18,000 plaques from the L2 cDNA library, 614 (3.4%) failed to hybridize to the B-cell cDNA probe. The subtracted L2 cDNA probe was hybridized to these 614 plaques and 114 (18%) gave a signal; 372 plaques gave no signal to the subtracted L2 cDNA probe or B-cell cDNA probe. Of those 372, 72 clones (19%) contained cDNA inserts. The 186 (114+72) clones from the L2 cDNA library were subjected to further analysis.

By similar analysis of approximately 8000 L3 cDNA clones, 150 plaques (2.0%) that failed to hybridize to P-labeled B-cell cDNA probe were selected. Instead of screening the 150 plaques with subtracted L2 cDNA probe, we digested recombinant phage DNA of each clone with EcoRi and immobilized the fragments on the filter. $^{35}$S-labeled B-cell cDNA probe was used to hybridize to the filters. The use of $^{35}$S for cDNA labeling and Southern analysis increased the sensitivity at least 5-fold. Fifty-six inserts (FIG. 1b) from L3 were identified, each of which failed to hybridize to the B-cell cDNA probe.

One hundred and eighty-six L2 cDNA inserts and 56 L3 cDNA inserts were hybridized to cDNAs of CSF-GM, IL-3, IL-2, TCR α-chain, TCR β-chain, c-myc, and c-fos. Twelve clones hybridized to cDNA, for IL-3, 6 to CSF-GM, 3 to IL-2, 2 to TCR β-chain, and 1 each to TCR α-chain and c-myc (Table 1). Twenty-nine clones whose cDNA inserts were less than 50 base pairs (bp) were eliminated from further study. The blots containing 132 L2 cDNA and 54 L3 cDNA inserts were hybridized to S-labeled ss cDNA probe prepared from poly(A)+ mRNA of unstimulated L3 or of unstimulated L2, respectively. Sixty-one inserts of L2 cDNA hybridized to the L3 cDNA probe and 14 inserts of L3 cDNA hybridized to the L2 cDNA probe.

TABLE 1

T-cell specific cDNA clones isolated from L2 and L3 cDNA library.

| Origin | Group | cDNA clone | Number of times isolated |
|---|---|---|---|
| L2 | 1 | CSF-GM | 6 |
|  | 2 | IL-3* | 12 |
|  | 3 | IL-2 | 3 |
|  | 4 | TCR α-chain | 1 |
|  | 5 | TCR β-chain | 2 |
|  | 6 | c-myc | 1 |
|  | 7 | pBK791 | 4 |
|  | 8 | pBK642 | 1 |
|  | 9 | pBK671 | 1 |
|  | 10 | pBK631 | 3 |
|  | 11 | L2G53#3 | 1 |
|  | 12 | L2G95#3 | 1 |
|  | 13 | L2G95#4 | 1 |
|  | 14 | L2G25#4 | 1 |
|  | 15 | L2S35#3 | 1 |
|  |  | Total | 39 |
| L3 | 1 | TCR β-chain | 2 |
|  | 2 | L3G29#4 | 1 |
|  | 3 | L3G25#4 | 1 |
|  | 4 | L3G14#2 | 1 |
|  | 5 | L3G10#6 | 1 |
|  | 6 | L3G7#1 | 1 |
|  | 7 | L3G18#3 | 1 |
|  | 8 | L3G26#1 | 1 |
|  |  | Total | 10 |

T-cell-specific cDNA clones were isolated from ~18,000 clones of L2 library and ~8000 clones of L3 library. After enrichment of T-cell-specific sequences, cDNA clones for CSF-GM, IL-3, IL-2, TCR α-chain, TCR β-chain, and c-myc were detected by hybridization with the corresponding full-length cDNA provided by other laboratories. By cross-hybridization, the other clones (14 from L2 and 8 from L3) turned out to represent 16 different genes (9 from L2 and 7 from L3). Those cDNA clones representing 16 different genes were subjected to further analysis.

A partial sequence analysis revealed that the IL-3-related clones contained two different species.

The 71 (132-61) inserts from L2 and 40 (54-14) inserts from L3 were used as probes with blots of 10 ug of poly(A)+ mRNA from K46, LGL (rat NK cells) (18), unstimulated or PTA-stimulated EL4, and 10 ug of total RNA from unstimulated or Con A-stimulated L2 or L3 cells.

Among these inserts, 29 (~40%, 29/71) from L2 and 19 (~47%, 19/40) from L3 hybridized to K46 or all lanes. Fourteen inserts (~20%, 14/71) from L2 hybridized only to Con A-stimulated L2, or both of L2 and L3 RNA. Those cDNA inserts represented nine different cDNAs. From L3, 8 (20%, 8/40) were T-cell specific, representing seven different genes; one gene was inducible by Con A in both L2 and L3, three genes were expressed constitutively and inducible by Con A only in L3 cells; and the rest were inducible by Con A in L3 cells but not found in unstimulated L3 cells. Twenty-eight inserts (40%, 28, 71) from the L2 cDNA library and 13 inserts (~32%, 13/40) from the L3 library did not hybridize to any of the RNAs. Because less L2 or L3 RNA was available for blot hybridization analysis, we have not been able to eliminate the possibility that those inserts not expressed in K46, EL4, or LGL could still be expressed in L2 or L3 at a low level.

Screening of cDNA Library and DNA Sequencing

L2 and L3 cDNA libraries which were previously prepared were rescreened with cDNA insert of each of 14 T-cell-specific genes. Typically 10 positive clones were chosen for each species and the sizes of cDNA inserts were determined. The longest cDNA inserts were employed for nucleotide sequence analysis. DNA restriction fragments, subdloned in M13 vectors (19), were sequenced by the dideoxy chain termination technique (20) employing Sequenase (U.S. Biochemical, Cleveland, Ohio), with modification made to accommodate 2'-deoxyadenosine 5'-[α-$^{35}$S] thiotriphosphate (21).

Nucleotide and Protein Sequence Comparison

Full length cDNA and predicted protein sequence were compared with the sequences in the GeneBank (NIH) DNA Sequence Library, European Molecular Biology Laboratories (EMBL) and National Biomedical Research Foundation (NBFR). Predicted protein were analyzed by PEPPLOT program.

Table 2 summarizes T-cell cDNAs identified from 14 hr ConA-stimulated L2 and L3 cDNA libraries. Besides the cDNAs listed in the table, CSF-GM, IL-2, IL-3, α-, β-T-cell receptor and c-myc cDNAs were identified by cross-hybridization of T-cell enriched cDNAs with the corresponding full-length cDNA provided by other laboratories.

TABLE 2

Summary of cDNA clones identified

| Full Length cDNA | cDNA Clone* Isolated Previously | Specificity of Expression | Identification |
|---|---|---|---|
| 4-1BB | L3G29#3, L3G25#4, L3G14#2 | L2 and L3 | unknown |
| L2G25B | L2G25#4, L2G95#4, L2G53#3, L2G95#3 | L2 and L3 | unknown (related to PLD78) |
| L2S35 | L2S35#3, L2PBK671 | L2 only | proenkephalin |
| 8-1R | L2PBK791, L2PBK642, L2PBK631 | L2 and EL-4 | T cell replacing factor |
| L3G10 | L3G10#6, L3G18#3 | L3 only | HF gene (serine esterase) |
| N.D.** | L3G7#1 | L3 and EL-4 | unknown |
| N.D.** | L3G26#1 | L3 and EL-4 | unknown |

*The cDNA clones were isolated independently and described as separate clones in the above-identified publication May 1987 Proc. Natl. Acad. Sci. USA., 84, 2896-2900.
**The full length version of the two clones was not isolated.

Among the 16 unidentified T-cell genes two represented proenkephalin which was identical to the sequence reported by Zurawski et al. (22), three were T-cell replacing factor (23), and two represented T-cell serine esterase gene (24).

Four species were from different regions of cDNA represented as L2G25B (800 base pairs). L2G25B was homologous to a human cDNA PLD 78 of unknown function. Three Species (L3G29#4, L3G25#4 and L3G14#2) were from different regions of 4-1BB (2,400 base pairs). There were no reports of sequences homologous to 4-1BB. L3G7#1 and L3G26#1 were not characterized vigorously since we could not isolate longer inserts and their expression was very low in L3.

In the previous studies, we also isolated 13 L3 cDNAs and whose specificity was not assigned by RNA blot analysis. One of them (13-1) was 64% homologous to reported T cell serine esterase (25). The sequence was reported as a new member of T cell serine esterase (26).

FIG. 2a shows the nucleotide and deduced amino acid sequence of the longest open reading frame of L2G25B. The open reading frame codes for 92 amino acids including a putative signal sequence. The deduced sequence of the first 23 amino acid residues has characteristics of the signal peptide of secretory proteins in that it mainly contains hydrophobic amino acids and terminates with a serine residue having a small side chain (27). Therefore the mature protein is composed of 69 amino acids with molecular weight of ~7880. There is no potential N-glycosylation site, or transmembrane-like domain. The 3' untranslated region has characteristics of other known lymphokines (AT rich) (28).

An optimum alignment between L2G25B and PLD78 is shown in FIG. 2b. The identity of amino acids between the two proteins was approximately 80%. The evolutionary conservation of these molecules from mouse to human may indicate that they play an important role in T-cell function.

FIG. 2a shows the nucleotide sequence of L2G25B and the deduced amino acid sequence. The nucleotide sequence of the message strand is numbered in the 5' to 3' direction. The 5' noncoding sequence is indicated by negative numbers. Nucleotide residue 1 is the first nucleotide of the ATG initiation codon. The predicted amino acid sequence is shown below. Potential signal peptide is underlined. Consensus polyadenylation signal is underlined. Stop codon is indicated by ( - - - ).

FIG. 2b shows the optimum alignment between L2G25B and PLD78-deduced amino acids. Homology search revealed that the amino acid sequence of L2G25B showed an extensive homology with a reported human sequence, PLD78 (29) of unknown function, whose expression is inducible by TPA in human tonsillar lymphocytes. The identity of amino acids between the two proteins was approximately 80%. *: Identical amino acids in these proteins. +: Chemically similar amino acids found in both sequences.

The nucleotide sequence of three overlapping cDNA clones represented by 4-1BB was determined according to the strategy shown in FIG. 3a. The nucleotide sequence of 4-1BB revealed a single long open reading frame, beginning with the ATG codon at nucleotide residues 1–3 (FIG. 3b.) This reading frame codes for a polypeptide of 256 amino acids with a molecular weight of 27,587. The assigned ATG is preceded by an in-frame termination codon TGA (nucleotide residues -12 to 9). The sequence flanking the assigned ATG (nucleotide residues -5 to 4) is a favored sequence for eukaryotic initiation sites (consensus; CCG/ACCATGG) described by Kozak (30). In fact, 8 out of 9 consensus sequences were identical to the sequences flanking to the assigned initiation codon. The codon specifying carboxy-terminal leucine is followed by the translational termination codon TGA (nucleotide residues 659–771). 4-1BB contains 1434 nucleotides of 3'-untranslated region which did not extend as far as polyadenylation signal nor the poly (A)$^+$ tail.

FIG. 3 shows the nucleotide sequence and the deduced amino acid sequence of 4-1BB. The nucleotides of the message strand are numbered in the 5' to 3' direction and numbers are shown on both sides of the sequence. Nucleotide residue 1 is the A of the initiation codon ATG, and the nucleotides on the 5' side of residue 1 are indicated by negative numbers. The predicted amino acid sequence is shown below the nucleotide sequence. Putative signal peptide is underlined. The potential asparagine-linked glycosylation sites are underlined. Potential polyadenylation signal is boxed. Stop codon is indicated by ( - - - ). Cysteine residues are highlighted by ( ). An unusual feature of 4-1BB sequence is that there is a potential polyadenylation signal of AATAAA at nucleotides 1158–1163 (FIG. 3b boxed). We believe that this signal is functional because this gene produces at least two different sizes of mRNA. We believe that this signal of AATAAA is at nucleotides 1158–1163 (FIG. 3b boxed). We believe that this signal is functional because this gene produces at least two different sizes of mRNA. FIGS. 4a and b show RNS blot analysis of ConA-stimulated L3 RNA. The blot was hybridized to the L3G25#4 probe which contained sequences of 3' side to the polyadenylation signal (nucleotides 1284–1557). The probe detected one RNA species of approximately 2.4 kb. When the same blot was hybridized to L3G14#2 probe which contained sequences of 5' side to the first polyadenylation signal (nucleotides 661–855), the probe detected two mRNA species of approximately 1.5 kb and 2.4 kb.

FIG. 4 shows the expression of two different sizes of 4-1BB mRNA. Ten micrograms of poly(A)$^+$ mRNA from mouse B cell line (K46), TPA-stimulated EL-4 (EL-4 TPA) and rat NK cell line (LGL), and ten micrograms of total RNA from unstimulated L3 (L3) and concanavalin A-stimulated L3 (L3 ConA) were fractionated on a 1.4% formaldehyde agarose gel, transferred to GeneScreen Plus and hybridized to [$^{32}$P]-labeled L3G25#4 (a), L3G14#2 (b) and L3G20#3 (c) sequentially. L3G25#4 and L3G14#2 represent cDNA fragments of the 3' side and 5' side to boxed AATAAA sequence, respectively.

L3G20#3 is an anonymous cDNA from L3 cDNA library and is used to show that each lane of the blot contains a similar amount of RNA. Positions of 28S and 18S rRNA markers are each indicated. Arrows indicate the specific hybridization signal.

The deduced sequence of the first 22 amino acids of 4-1BB has characteristics of the signal peptide of secretory and membrane-associated protein (27), which mainly contains hydrophobic amino acids. We putatively assigned the first 22 amino acids as a signal peptide. A possible cleavage site of the signal peptide is after glycine residue at alanine (FIG. 3b). Gly-Ala at amino acid positions 22 and 23 is one of the favorable signal peptidase cleavage sites(*). Thus the protein backbone of processed 4-1BB protein is composed of 234 amino acids with a molecular weight of 25,000. We found two potential asparagine-linked glycosylation signals (22,23) at amino acid positions 129 and 138 as underlined in FIG. 3b. The predicted 4-1BB protein contains unusually large numbers of cysteines. There are 23 cysteine residues in the putative mature protein as dotted in FIG. 3a.

There is a stretch of 26 amino acids that constitutes hydrophobic domain toward the carboxy terminus of the protein (amino acids at positions 182–211). Whether this region serves as a membrane-spanning domain is not known. This region is followed by the 45 amino acids which constitute a hydrophilic region.

Southern Blot Analysis

As shown in FIG. 5, fragments of L2G25B and 4-1BB cDNA each detect a single restriction fragment of approximately 15 kb and 18 kb in both C57BL/6 and BALB/c, DNA, respectively. The data indicate that the genes encoding the two molecules exist as a single copy in C57BL/6 and BALB/c mice. FIG. 5 shows a Southern Blot analysis of mouse genomic DNA. Genomic DNA from C57BL/6 (lanes 1,3) and BALB/c (lanes 2,4) was digested with EcoRI restriction enzyme, fractionated on a 0.8% agarose gel, transferred to GeneScreen Plus and hybridized to [$^{32}$P] labeled L2G25B (lanes 1,2) and 4-1BB (lanes 3,4).

The protocol developed by the present inventor and reported and published as identified hereinabove for a modified differential screening of a cDNA library by which one can detect a broad representation of the mRNA expressed differentially in two different cell types, was applied to the systematic analysis of HTL and CTL gene expression and allowed us to isolate T-cell subset specific genes. This approach offers an alternative to the classical protein purification for identifying molecules and genes. Advantages of this method are: 1) The approach identifies the existence of molecules which otherwise may be difficult or impossible to recognize or isolate; 2) Even molecules which exist at a low level in the natural source can be produced in quantity by recombinant DNA technologies and in turn provide enough protein to permit study of function and possibly clinical applications; and 3) It is a straightforward method for identifying mutations of the gene using the nucleic acid probe. As an illustration of the usefulness of this approach, the genes for T-cell antigen receptors and X-linked immunodeficiency (xid) genes were cloned and characterized in this fashion (31). This approach in our hands has already proven to be useful in isolating known as well as previously unrecognized T-cell mediators.

Using the same concanavalin A-stimulated L2 cells, Prystowsky et al. (32) identified 10 different lymphokine activities from culture supernatants; they include IL-2, IL-3, BCSF, CSF, IFN- and five unidentified factors which affect macrophage activities. In the course of the studies we isolated and identified cDNAs for IL-2, IL-3, CSF, T cell replacing factor and proenkephalins from our concanavalin A-stimulated L2 and cDNA library (2 and unpublished observations). Therefore, L2G25B 4-1BB might represent the novel soluble mediators of Prystowsky et al. which affect macrophage activities.

By applying a modified differential screening of L2 and L3 cDNA library, two novel T cell genes were isolated. Correlation of these T cell molecules with functional activities was shown by the following evidence. L2G25B is shown to code for a lymphokine and 4-1BB is shown to have a similar activity, however, 4-1BB is later shown to be a receptor protein.

T-cell-Specific Expression of L2G25B and 4-1BB

L2G25B was isolated from an L2 cDNA library, and 4-1BB was isolated from an L3 cDNA library by the aforesaid modified differential screening (5). As shown in FIGS. 6a and 6b, L2G25B and 4-1 BB were expressed preferentially in L2 and L3 cells only after concanavalin A stimulation. The sizes of transcripts were approximately 800 bases for L2G25B and 2400 bases for 4-1BB. The abundance of the two transcripts was 5~10 fold higher in L2 cells than in L3 cells. The two transcripts were not detectable in K46 B cells, EL-4 thymoma cells or rat large granular lymphocytes. L2G25B mRNA was consistently more abundant than 4-1BB mRNA. FIGS. 6a and 6b show T-cell specific expression of L2G25B and 4-1BB mRNA. Poly (A)$^+$ mRNA was prepared from mouse B cell line (K46), unstimulated EL-4 (EL-4), TPA-stimulated EL-4 (EL-4 TPA) and rat NK cell line (LGL), and total RNA was prepared from unstimulated L2 (L2), concanavalin A-stimulated L2 (L2 ConA), unstimulated L3 (L3) and concanavalin A-stimulated L3 (L3 ConA). Ten micrograms of total RNA or ten micrograms of poly(A)$^+$ RNA was fractionated on a formaldehyde/agarose gel, transferred to GeneScreen Plus and hybridized to [$^{32}$P]-labeled L2G25B (a) and 4-1BB(b) sequentially. Positions of 28S and 18S rRNA markers are each indicated. An arrow indicates the specific hybridization signal.

Figure 7A:
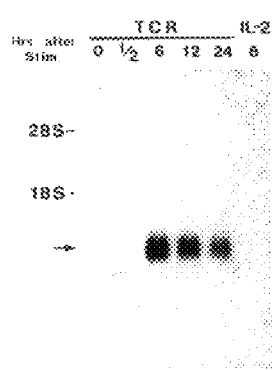
Figure 7B:
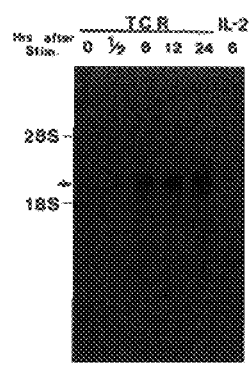

L2G25B and 4-1BB mRNA Were Inducible by TCR Stimulation, But Not by IL-2 Stimulation The inducibility of the two cDNA clones was tested after L3 TCR stimulation by clonotypic antiTCR mAb, 384.5, or IL-2. As shown in FIGS. 7a and 7b, the expression of the two cDNA was inducible by TCR stimulation but not by IL-2 stimulation in L3 Cells. L2G25B mRNA was detectable at 0.5 hr after TCR stimulation, peaked at 6 hr, and decreased thereafter until at least 24 hr. 4-1BB mRNA was detectable at a very low level in unstimulated L3 cells in this experiment. The induction of 4-1BB mRNA occurred approximately 6 hr after TCR stimulation and remained level until 24 hr.

Figure 7C:
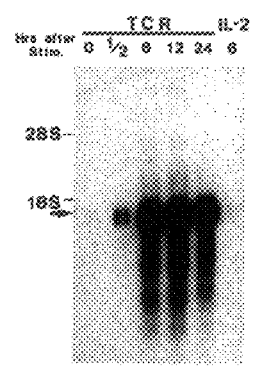
Figure 7D:
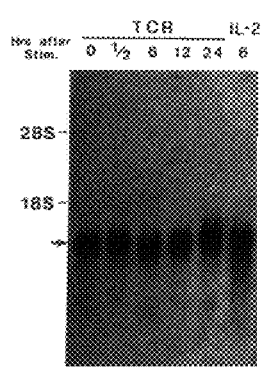

FIG. 7c shows the kinetics of IFN-δ mRNA expression in the same RNA blot as used in FIGS. 7a and 7b. IFN-δ mRNA was detectable at 0.5 hr after TCR stimulation, peaked at 12 hr and declined slightly until 24 hr. There was a low level of IFN-δ mRNA in unstimulated L3 cells. When we compared the peak level of L2G25B and 4-1BB mRNA with that of IFN-δ mRNA, IFN-δ mRNA was at least 20 fold higher than that of L2G25B mRNA and a least 50 fold higher than that of 4-1BB mRNA. FIG. 7d demonstrates that all six lanes contained almost identical amounts of RNA. The probe was a serine protease cDNA (L3G10#6) isolated from L3 cells. In summary, the pattern of the two cDNA expression was similar to that of IFN-δ expression. FIG. 7 shows patterns of L2G25B and 4-1BB mRNA expression after TCR stimulation or IL-2 treatment. L3 cells were stimulated with clonotypic antiTCR mAb 384.5 for 0, ½, 6, 12 or 24 hr or with rIL-2 for 6 hr. Ten ug of total RNA was fractionated on a formaldehyde/agarose gel, transferred to GeneScreen Plus and hybridized to [$^{32}$P]-labeled L2G25B (a) 4-1BB(b), IFN-δ (c) and L3G10#6 (d) cDNA. L3G10#6 is a serine protease cDNA isolated from L3 cell cDNA library, which is identical to HF gene (24). L3G10#6 is used to show that each lane contains almost equal amounts of RNA. Positions of 28S and 18S rRNA markers are each indicated. An arrow indicates the specific hybridization signal.

L2G25B and 4-11BB mRNA are Inducible by TCR Stimulation in Other Cloned HTL, CTL and Hybridomas As shown in FIGS. 8a and 8b, L2G25B and 4-1BB mRNA are also inducible in HTL L2 and CTL dB45 after TCR stimulation with antiTCR mAb F23.1. The mRNA level for the two cDNA was also much lower than that of IFN-δ in L2 and dB45 cells (FIG. 8c). L2 cells show the highest level of expression of the three cell clones. FIG. 8 shows expression of L2G25B and 4-1BB mRNA in HTL L2 and a CTL dB45 cells. HTL L2 and CTL dB45 cells were stimulated with antiTCR mAb F23.1 for 6 hr. L3 cells were stimulated with antiTCR mAb 384.5 for 6 hr. Ten ug of total RNA from unstimulated L3 (lane a) and stimulated L3 (lane 2), unstimulated dB45 (lane 3), stimulated dB45 (lane 4), unstimulated L2 (lane 5) and stimulated L2 (lane 6) was fractionated on formaldehyde/agarose denaturing gel, transferred to GeneScreen Plus and hybridized to [$^{32}$P] labeled L2G25B(a), 4-1BB(b), and IFN-δ (c) cDNA. A fraction of RNA in each lane was degraded and detected as RNAs in lower molecular sizes. We also found that 4-1BB mRNA was inducible by concanavalin A in two cytotoxic hybridomas, PN37 and Md90 (FIG. 9a) and detectable in unstimulated CTLLA11 CTL (FIG. 9b) clones.

FIG. 9 shows expression of 4-1BB mRNA in concanavalin A-stimulated hybridomas PN37 and Md90, and in an unstimulated CTL CTLLA11 . FIG. 9a shows BW5147, PN34 and Md90 cells were stimulated with concanavalin A for 4 hr. Ten ug of poly(A)$^+$ mRNA from unstimulated and stimulated each of these cells was fractionated, transferred to nitrocellulose filter and probed with [32p]-labeled 4-1BB cDNA. FIG. 9b shows ten ug of poly(A)+ mRNA from mouse melanoma cells (melanocyte) and ten ug of total RNA from unstimulated L2 (L2), CTLLA11 (A11) and L3 (L3) cells was fractionated, transferred to GeneScreen Plus and hybridized to [$^{32}$P] 4-1BB cDNA.

Effects of Cyclosporin A on L2G25B and 4-1BB Transcription

Figure 10A:
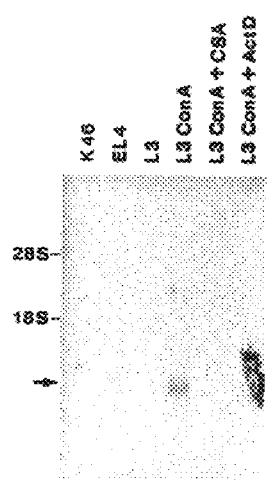
Figure 10B:
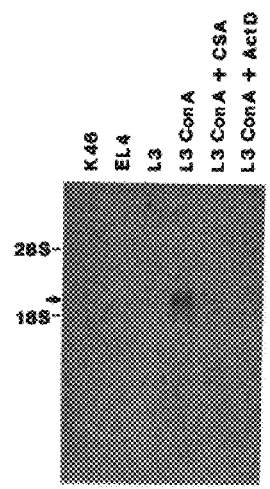
Figure 10C:
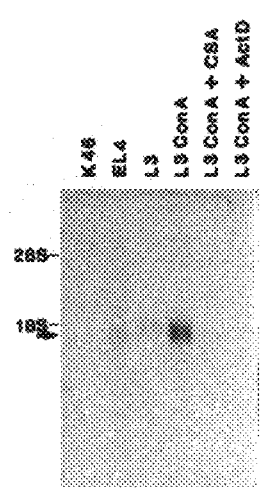
Figure 10D:
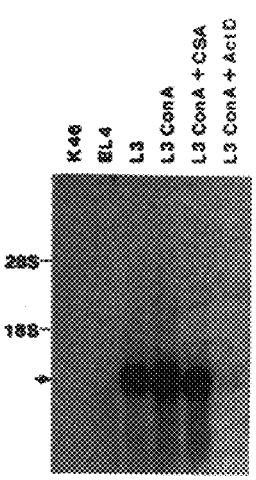

To test the possibility that the two cDNAs represent two different soluble extracellular mediators, we next examined the effect of cyclosporin A on RNA expression. Cyclosporin A inhibits mitogen or antigen-induced T-cell proliferation (33). It has also been shown to block the induction of expression of several lymphokine genes including IL-2 and IFN-δ (34). The inhibition of lymphokine production occurs at a pretranslational level (35). In contrast cyclosporin A appears to have no effect on the inducible expression of c-fos and IL-2 receptor genes in T cells. As shown in FIGS. 10a and 10b, cyclosporin A inhibited the induced accumulation of L2G25B and 4-1BB mRNA. The same findings were seen with IFN-δ (FIG. 10c). A low level of expression of L2G25B mRNA was seen in TPA-stimulated EL-4 cells in this experiment. FIG. 9d shows that cyclosporin A had minimal or no effect on the level of serine protease (probe, L3G10#6) mRNA and shows that the three lanes contained almost equal amounts of RNA (EL-4 or K46 cells did not express L3G10#6 mRNA). This data strongly suggests that L2G25B and 4-1BB expression may show some of the same activation requirements as other known lymphokines.

FIG. 10 shows the effect of cyclosporin A on L2G25B and 4-1BB mRNA expression. L3 cells were stimulated with concanavalin A, concanavalin plus cyclosporin A or concanavalin 1A plus actinomycin D. Ten ug of total RNA from unstimulated L3(L3), concanavalin A-stimulated L3 (L3 ConA), concanavalin A plus cyclosporin A-treated L3 (L3 ConA+CsA) and concanavalin A plus actinomycin D-treated L3 (L3 ConA+ActD) cells and ten ug of poly(A) mRNA from K46 (K46) and TPA-stimulated EL-4 cells (EL-4) were fractionated, transferred to GeneScreen Plus membrane and hybridized to [$^{32}$P] labeled L2G25B(a), 4-1BB(b), IFN-δ (c) and L3G10#6(d) cDNA. Cyclosporin A treatment did not alter the level of L3G10#6 mRNA but almost completely abrogated the induced expression of other 4 mRNA species. An arrow indicates a specific hybridization signal.

L2G25B and 4-1BB mRNA Were Inducible in Normal Mouse Spleen Cells

To find out if the expression of these genes were not unique to certain cloned T cells or hybridoma cells, splenocytes from C57BL/6 and BALB/c mice were stimulated with concanavalin A and tested for mRNA expression. As shown in FIGS. 11a and 11b the two mRNA were detectable after concanavalin A stimulation in C57BL/6 and BALB/c mouse splenocytes. They were also inducible in Swiss Webster mouse splenocytes (data not shown). As shown in FIG. 10c IFN-δ mRNA was detectable in concanavalin A-stimulated BALB/c splenocytes (for unknown reasons IFN-δ mRNA was not detectable in concanavalin A-stimulated C57BL/6 splenocytes in this experiment). RNA preparations for Figure c were different from those for FIGS. a and b. These data suggest that these molecules may be induced in normal mouse spleen cells by appropriate stimuli as in the cloned T cells.

FIG. 11 shows the expression of L2G25B and 4-1BB mRNA in mouse splenocytes. Splenocytes were obtained from C57BL/6 and BALB/c mice and stimulated with concanavalin A for 14 hr. Ten ug of total RNA from unstimulated BALB/c (lane 1) and stimulated BALB/c (lane 2), unstimulated C57BL/6 (lane 3) and stimulated C57BL/6 (lane 4) splenocytes was fractionated, transferred to Gene-Screen Plus and hybridized to [$^{32}$P]-labeled L2G25B(a), 4-1BB(b) and IFN-δ (c) cDNA. A portion of L3G29 cDNA (approximately 200 pairs in the middle of the molecule) consistently detects an additional RNA species of approximately 1500 bases. The additional hybridization signal is seen in FIG. 11b.

L2G25B and 4-1BB share properties which suggest that they encode soluble T-cell mediators. The properties are; 1) the mRNA of the two is preferentially expressed in T cells; 2) The mRNAs of the two genes are present in undetectable amount in T cells until induced by concanavalin A, or by TCR stimulation; 3) The small size of the mRNA of L2G25 is consistent with features of several analyzed lymphokine cDNAs such as interleukins 2,3 and 5; 4) The patterns of expression are very similar to that of the lymphokine IFN-δ; 5) Both have a potential signal sequence and an AT rich 3' untranslated region consistent with a lymphokine gene (28); and 6) Cyclosporin A inhibits the induced mRNA expression corresponding to the two cDNAs. Using the same concanavalin A stimulated L2 cells, Prystowsky et al. (32) identified 10 different lymphokine activities from culture supernatants; they include IL-2, IL-3, BCSF, CSF, T-cell replacing factor and proenkephalins from our concanavalin A-stimulated L2 cDNA library (5 and unpublished observation). Therefore, L2G25B and 4-1BB might represent the novel soluble mediators of Prystowsky et al. which affect macrophage activities.

Isolation of Human Lymphokines and Receptors Homologous to L2G25B and 4-1BB

L2G25B and 4-1BB cDNA may be used as probes to isolate human lymphokines homologous to these type clones. Each cDNA will be radio-labeled and hybridized to human genomic DNA blot under various stringency and washing conditions using standard laboratory techniques known to those skilled in the art.

The species difference in nucleotide sequences between human and mouse will determine the degree of homology by clone hybridization experiments. On the determination of the optimal hybridization and washing conditions under which the probes detect a signal in the human genomic DNA blot, then a human genomic library in lambda vector may be screened with radio labeled L2G25B and 4-1BB. The hybridizing human clones may then be isolated and the nucleotide sequences determined.

The genomic human clone corresponding to mouse clone L2G25 and 4-1BB may then be used as a probe to survey human T cells which express mRNA by RNA blot analysis. When we identify the human T cells which express the RNA homologous to L2G25B and 4-1BB, the RNA may then be used to construct a cDNA library. Then the cDNA library may be screened with the human genomic clone corresponding to L2G25B and 4-1BB and isolate the human cDNA clones corresponding to L2G25B and 4-1BB.

Plasmid p4-1BB may be used to grow the receptor 4-1BB. Plasmid L2G25B may be used to grow the lymphokine L2G25B. To do so: one must insert the cDNA of L2G25B (for example) into an appropriate prokaryotic or a eukaryotic expression vector such as a Bovine Papilloma virus expression vector; and transfecting that expression vector into mouse fibroblasts or other appropriate transfection hosts; and grow the then transfected mouse fibroblasts in an appropriate culture media; and then purifing the lymphokine protein from the culture media. The same approach can be used to grow the receptor 4-1BB.

cDNA in the form of plasmid p4-1BB in *E. coli* NM 522 has been deposited at the American Type Culture Collection under ATTC No: 67825 and will be available after this Patent Application issues.

cDNA in the form of plasmid pL2G25B in *E. coli* NM 522 was deposited on Oct. 19, 1988 at the American Type Culture Collection, 10801 University Boulevard, Manassas, Va., 20110-2209 under ATCC No.: 67826 and will be available after this Patent Application issues.

Macrophage Inflammatory Protein (MIP)-1β Abrogates the Capacity of MIP-1α to Suppress Myeloid Progenitor Cell Growth Myeloid blood cell production is modulated by an interacting network of cytokines, many of which have pleiotropic effects (36). Some of the cytokines have been implicated in the enhancement or suppression of myelopoiesis stimulated by the hematopoietic CSFs. Within this group of enhancing/suppressing cytokines are the macrophage inflammatory proteins (MIP)-1 and -2 (37). These are heparin-binding proteins originally identified by their capacity to cause a localized inflammatory reaction after injection into the footpads of C3H/HeJ mice (38). MIP-1 and -2 represent two families of molecules that are structurally related and that may have evolved from a common ancestral gene that duplicated and then diverged (39). They are part of what has been termed a proinflammatory supergene "intercrine" cytokine family (40). Mu MIP-1α, MIP-1β and MIP-2 have molecular weights of approximately 8 KD.

MuMIP-1α, muMIP-1β and muMIP-2 have enhancing activity for the more mature mu bone marrow CFU-GM stimulated by muGM-CSF or muM-CSF and human marrow CFU-GM stimulated by huGM-CSF. This enhancing activity was detected with the mu forms of natural MIP-1 (composed of MIP-1α and MIP-1β) and MIP-2 and rMIP-1α, rMIP-1β and rMIP-2, and was most apparent when suboptimal amounts of CSF were used to stimulate CFU-GM. Natural and r preparations of MIP had no effect on colony formation by BFU-E growing in the presence of Epo. In contrast, rmuMIP-1α and natural MIP-1, but not rmuMIP-1β or natural rmuMIP-2, had suppressive effects on hu and mu CFU-GEMM, muCFU-A (an apparently early progenitor cell) day 12 CFU-S, and on subpopulations of more immature/earlier forms of hu and mu BFU-E and CFU-GM. Suppression by MIP-1α was manifest on progenitors stimulated to proliferate by combinations of CSF (e.g., Epo and IL-3 or GM-CSF for CFU-GEMM and BFU-E, or IL-3 and GM-CSF for CFU-GM). The enhancing and suppressing effects of the MIP preparations were mediated by direct actions on the hematopoietic progenitors.

The current study was undertaken to assess the influence of rmuMIP-1β or rmuMIP-2 on the suppressive effects of rmuMIP-1α on growth of colonies in vitro from hu and mu CFU-GEMM, BFU-E and CFU-GM. Effects were evaluated by adding MIP preparations together with cells, or after pulse-exposure of cells to one MIP, followed by addition of the other MIP to the cells. Cells were stimulated by combinations of CSF, including for hu cells a newly engineered rhuGM-CSF/IL-3 fusion protein (41) and mast cell growth factor (MGF, a ligand for the c-kit proto-oncogene product (42), also termed by others stem cell factor (43) or KL (44). The GM-CSF/IL-3 fusion protein is a more potent stimulator than the combination of GM-CSF plus IL-3 and MGF is a potent co-stimulating factor. These molecules act on early progenitor cells and allow detection of progenitors not apparent in the absence of these cytokines. This allowed a determination of the effectiveness of MIP-1α for suppression of the potent stimulating activity of these newly described cytokines. As a control for specificity, H-ferritin, another suppressor molecule (45), with direct acting effects on myeloid progenitors (46), was chosen. H-ferritin's action is mediated by its capacity to manifest ferroxidase activity (47). H-ferritin was chosen to assess specificity because, of the many other suppressor molecules, the possibility existed that MIP-1α and H-ferritin might share an action on common target progenitor cells. (48). The results presented here demonstrate that MIP-1β, but not MIP-2, counteracts the myelosuppressive effects of MIP-1α, but not H-ferritin, on cells stimulated by all combinations of CSFs tested, including the potent GM-CSF/IL-3 fusion protein and MGF. Furthermore, the data suggest that MIP-1β and MIP-1α act on myeloid progenitor cells through a rapid action, that at least in vitro and under the conditions assessed appears to be non-reversible.

Materials and Methods

Cells

Human bone marrow cells were obtained by aspiration from the posterior iliac crest of healthy volunteers who had given informed consent. LD cells ($<1.077$ g/cm$^3$) were retrieved after density cut separation on Ficoll-Hypaque (Pharmacia Fine Chemicals, Piscataway, N.J.) and used as such or after additional depletion also of monocytes (by adherence to plastic) and T-lymphocytes (by removal of E-rosette positive cells). The NALDT-fraction of cells contained less than 3% monocytes (non-specific esterase positive) and T-lymphocytes (CD3 positive) cells. Femoral bone marrow cells were obtained from 4- to 6-week-old (C57B1/6×DBA/2)F$_1$ (BDF$_1$) female mice purchased from Jackson Laboratories, Bar Harbor, Me. Cells were used as isolated.

Biomolecules

RmuMIP-1α, rmuMIP-1β and rmuMIP-2 were expressed in *Saccharomyces cerevisiae* and purified to homogeneity according to methods established for the natural proteins. The purified recombinant T-cell-derived MIP-1α was produced using a bovine papilloma virus expression system (49). Both forms of MIP-1α were equally active. Recombinant wildtype H-subunit ferritin and an inactive mutein, 222 (lacking ferroxidase activity) were produced in *E. coli* and purified as described elsewhere. The iron uptake, incorporation and ferroxidase activities of these H-ferritin molecules have been reported elsewhere. RhuIL-3 and rhuGM-CSF (each $10^8$ units/mg), purified yeast expressed rmuMGF and purified rhuGM-CSF/IL-3 fusion protein (PIXY321) were from Immunex Corp., Seattle, Wash. The design of the fusion protein incorporated a flexible linker sequence to maximize the opportunity for GM-CSF and IL-3 to fold into their native 3-dimensional structures. The fusion protein was constructed using GM-CSF and IL-3 molecules from which asparagine linked glycosylation sites had been removed in a yeast expression vector. Recombinant Epo was purchased from Amgen, Thousand Oaks, Calif., and pokeweed mitogen mouse spleen cell conditioned medium (PWMSCM), which contains GM-CSF, IL-3 and other cytokines, was used as a source of mouse active CSF.

Colony Assays

Unseparated mouse, LD hu, and NALDT hu bone marrow cells were respectively plated at $7.5 \times 10^4$, $1.0 \times 10^5$ and $2.5 \times 10^4$ cells/ml for CFU-GEMM and BFU-E assays in 1.3% methylcellulose with 1 unit/ml rEpo with or without other growth factors, and for CFU-GM assay in 0.3% agar or 0.4% agarose (50) with growth factors. Mu and hu cells were respectively incubated for 7 and 14 days at 5% $CO_2$ in lowered (5%) $O_2$ tension in an ESPEC $N_2$—$O_2$—$CO_2$ incubator NP-210 (Tabai ESPEC Corp., South Plainfield, N.J.) before scoring colonies.

Statistics

Results are expressed as mean +/−1 SEM of three plates per point for CFU-GM and four plates per point for BFU-E. Levels of significance were determined using student's t distribution.

Results

Abrogation by MIP-1β of the Suppressive Effects of MIP-1α

MIP-1α, MIP-1β, and MIP-2 were assessed alone and in combination (added simultaneously to culture dishes) for effects on colony formation by BFU-E, CFU-GEMM (FIG. 12) and CFU-GM (FIG. 13) in $10^5$ LD normal human bone marrow cells.

FIG. 12 shows the influence of MIP-1P β and MIP-2 on the suppressive effects of MIP-1α on colony formation by low density (LD) human bone marrow (BM) erythroid (BFU-E) and multipotential (CFU-GEMM) progenitor cells stimulated by erythropoietin (Epo) plus interleukin (IL)-3. The inhibition by MIP-1α ($p<0.001$) was completely counterbalanced by a 4 fold excess, and partially counterbalanced by a 2 fold excess, of MIP-1β. MIP-2 did not counterbalance the suppressive effects of MIP-1α.

FIG. 13 shows the influence of MIP-1β and MIP-2 on the suppressive effects of MIP-1α on colony (>40 cells/aggregate) and cluster (3–40 cells/aggregate) formation by LD human BM CFU-GM stimulated by GM-CSF plus IL-3 in agarose culture medium. Results were similar to that noted in the legend to FIG. 12.

As previously reported MIP-1α (using plateau concentrations of 50 to 200 ng/ml), but not MIP-1β (200 ng/ml as shown here, but up to 1000 ng/ml, not shown) or MIP-2 (1000 ng/ml) suppressed completely the IL-3 enhanced Epo-dependent growth of BFU-E and CFU-GEMM colonies (FIG. 12) and suppressed partially growth of CFU-GM colonies and clusters stimulated by GM-CSF plus IL-3 (FIG. 13). A 4:1 ratio of MIP-1β (200 ng/ml) to MIP-1α (50 ng/ml) completely blocked the myelosuppressive effects of MIPla. A 2:1 ratio of MIP-1β to MIP-1α partially blocked myelosuppression by MIP-1α, while a 1:1 ratio of MIP-1β to MIP-1α had no effect on MIP-1α suppressive activity. MIP-2, even at concentrations 20 times that of MIP-1α, did not block myelosuppression by MIP-1α. Similar effects were noted when those mu derived r proteins, MIP-1α, MIP-1β and MIP-2, were assessed alone and in combination for effects on mouse bone marrow colony formation of BFU-E and CFU-GEMM stimulated by Epo plus PWM-SCM (FIG. 14) and of CFU-GM stimulated by PWMSCM (FIG. 15).

FIG. 14 shows the influence of MIP-1β and MIP-2 on the suppressive effects of MIP-1α on colony formation by mouse marrow BFU-E and CFU-GEMM stimulated by Epo and pokeweed mitogen mouse spleen cell conditioned medium (PWMSCM). The inhibitory activity by MIP-1α ($p<0.001$) was completely counterbalanced by a 5 fold excess of MIP-1β. MIP-2 did not counterbalance the suppressive effects of MIP-1α. FIG. 15 shows the influence of MIP-1β and MIP-2 on the suppressive effects of MIP-1α on colony formation by mouse marrow CFU-GM stimulated by PWMSCM in agar culture medium. Results were similar to that noted in the legend to FIG. 14.

Again, an excess of MIP-1β, but not of MIP-2 blocked the suppressive effects of MIP-1α. In at least 7 experiments each studying effects of human and mouse BFU-E, CFU-GEMM and CFU-GM, a 4:1 ratio of MIP-1β to MIP-1α was required for complete blocking of MIP-1α myelosuppressive effects. MIP-2 had no blocking effects.

Effect of Preincubation on the Actions of MIP-1α and MIP-1β

In order to define the mode of action of MIP-1β to counterbalance the suppressive effects of MIP-1α, NALDT human bone marrow cells were preincubated at 4° C. for 1 hr. with control (McCoy's) medium, MIP-1α (100 ng/$10^5$ cells) or MIP-1β (400 ng/$10^5$ cells) prior to washing the cells 2× and plating in semi-solid medium with control medium, MIP-1α (50 ng/ml), MIP-1β (200 ng/ml) or the combination of MIP-1α (50 ng/ml) plus MIP-1β (200 ng/ml). NALDT cells were then plated at $2.5\times10^4$/ml and assessed for BFU-E (FIG. 16) and CFU-GEMM (FIG. 17) colony formation stimulated by Epo (1 U/ml) with IL-3 (200 U/ml; upper portion of each figure) or Epo with MGF (50 ng/ml; lower portion of each figure). Results were compared to growth in Epo alone cultures (darkened bars).

FIG. 16 shows the influence of pulse treatment of non-adherent low density T-lymphocyte depleted (NALDT) human bone marrow cells with MIP-1α or MIP-1β on colony formation by BFU-E stimulated with Epo plus IL-3 or mast cell growth factor (MGF). Pulse treatment of cells with MIP-1α at 4° C. for 1 hr was as effective in inhibiting colony formation ($p<0.001$) as continuous exposure of cells to MIP-1α, and the pulsing effect could not be overcome by subsequent exposure of cells to MIP-1β. Pulse exposure of cells to MIP-1β blocked the suppressive activity of subsequently added MIP-1α. FIG. 17 shows the influence of pulse treatment of NALDT human marrow cells with MIP-1α or MIP-1β on colony formation by CFU-GEMM stimulated by Epo plus IL-3 or MGF. Results were similar to that noted in the legend to FIG. 16.

The effects of cells pulsed with MIP-1αMIP-1β were similar to results seen in FIGS. 12 and 13 in that MIP-1α suppressed, MIP-1β did not suppress and MIP-1β blocked the suppressive effects of MIP-1α on the IL-3 enhancement of Epo-dependent BFU-E (FIG. 16) and CFU-GEMM (FIG. 17) colony formation. MGF was a more potent stimulator of Epo-dependent BFU-E and CFU-GEMM colony formation than IL-3. MIP-1α/MIP-1β effects were qualitatively similar with IL-3 or MGF but quantitatively different in that MIP-1α suppressive effects were greater on MGF, than on IL-3, stimulated colonies. Colony formation by cells pulsed with MIP-1α for 1 hr. were as suppressed as cells plated for 14 days in the presence of MIP-1α, and addition of MIP-1α for 14 days to cultures of cells pulsed with MIP-1α did not result in any further inhibition of colony formation. Addition of MIP-1β to cultures of cells pulsed with MIP-1α did not counterbalance the myelosuppressive effects of MIP-1α. In contrast, MIP-1α had no suppressive effects on colony formation by cells first pulsed with MIP-1β.

A newly engineered human GM-CSF/IL-3 fusion protein which is a more potent stimulator than the combination of IL-3 plus GM-CSF on CFU-GM and on Epo-dependent BFU-E and CFU-GEMM was also tested. Fusion protein stimulated CFU-GM were suppressed by pulse exposure of cells to MIP-1α, an effect not overcome by subsequent addition of MIP-1β to cultures, and pulse exposure of these cells to MIP-1β blocked the suppressive effects of subsequent addition of MIP-1α to the cultures (FIG. 18). FIG. 18 shows the influence of pulse treatment of NALDT-human marrow cells with MIP-1α or MIP-1β on colony formation by CFU-GM stimulated by a GM-CSF/IL-3 fusion protein in agarose culture medium. Results were similar to that noted in the legend to FIG. 16n. These results are similar to those noted in FIGS. 16 and 17 for IL-3 and MGF enhanced Epo-dependent BFU-E and CFU-GEMM and are consistent with receptor-mediated effects of MIP-1α/MIP-1 β, and suggest that the effects on BFU-E and CFU-GEMM are independent of the early-acting cytokines used.

Effect of MIP-1β on the Non-Related Inhibitor H-Ferritin. MIP-1α (100 ng/ml) and recombinant wild-type H-ferritin ($10^{-9}$ M) were compared for activity on colony formation by CFU-GM, and Epo-dependent BFU-E and CFU-GEMM in $10^5$ LD human bone marrow cells stimulated by the GM-CSF/IL-3 fusion protein (2.5 ng/ml). Both MIP-1α and H-ferritin had similar ranges of significant suppressive activity ($p<0.01$), which were respectively 63±2 vs. 57±2% inhibition of CFU-GM, 69±3 vs. 66±3% inhibition of BFU-E, and 76±4 vs. 84±3% inhibition of CFU-GEMM (N=3 to 4 experiments each with control colonies ranging from 59–169 for CFU-GM, 77–170 for BFU-E and 8.5 to 15.3 for CFU-GEMM). A recombinant H-ferritin mutein (#222), which lacks ferroxidase activity and has previously been shown to be inactive on CSF-stimulated colony formation and MIP-1β and MIP-2 had no significant effects ($p>0.05$) on colony formation. MIP-1α and H-ferritin also had equal suppressive activities when BFU-E and CFU-GEMM in $2.5\times10^4$ NALDT normal human bone marrow cells were stimulated with Epo (1 U/ml) plus MGF (50 ng/ml) (FIG. 19). FIG. 19 shows the comparative effects of MIP-1α and H-subunit ferritin on colony formation by NALDT-human bone marrow BFU-E and CFU-GEMM stimulated by Epo alone, or in combination with either the GM-CSF/IL-3 fusion protein or MGF. The suppressive activities of MIP-1α and H-ferritin were similar but greater against cells stimulated by MGF than by the fusion protein. MGF was a more potent enhancing molecule for Epo-dependent BFU-E and CFU-GEMM than the GM-CSF/IL-3 fusion protein (when both MGF and the fusion protein were each used at maximal concentrations for activity) and the inhibitory activities of both MIP-1α and H-ferritin were greater for MGF-, than for the fusion protein-responsive BFU-E and CFU-GEMM (FIG. 19).

In order to further determine the specificity of MIP-1β on the modes of actions of MIP-1α, MIP-1α and H-ferritin were compared for activity on CFU-GM, BFU-E and CFU-GEMM in $2.5\times10^4$ NALDT⁻ human marrow cells, alone and in combination, with each other and with MIP-1β (FIG. 20). FIG. 20 shows the influence of MIP-1β, hemin, and inactive H-ferritin mutein on suppressive effects of MIP-1α and wildtype H-ferritin on myeloid colony formation. Hemin, and the inactive H-ferritin mutein 222, were used as abrogators of H-ferritin activity. It was anticipated that these results could be used to detect differences in modes of action of the MIP-1α and H-ferritin molecules and at the same time act as specificity controls for each other. Evaluating effects on CFU-GM colonies stimulated with GM-CSF plus MGF, on BFU-E colonies stimulated with Epo plus fusion protein, and on CFU-GEMM colonies stimulated with Epo plus MGF, the following new results were found. Firstly, the combination of H-ferritin and MIP-1α did not result in any further inhibition than that detected with either molecule alone. Secondly, excess H-ferritin mutein 222 and hemin blocked the inhibitory activity of the wildtype H-ferritin, but not of MIP-1α, while MIP-1β did not block the suppressive activity of the wildtype H-ferritin. These individual effects were apparent even when 3 or more of these molecules were placed in combination. For example, inhibitory activity was noted with the combination of MIP-1α a plus MIP-1β plus H-ferritin, but the addition of hemin to this mixture resulted in loss of inhibition. Also, inhibitory activity was noted with the combination of H-ferritin wildtype plus H-ferritin mutein 222 plus MIP-1α, but the addition of MIP-1β to this mixture resulted in loss of inhibition. Thus, even though MIP-1β with a 1 hr pulse exposure can prevent the inhibitor action of MIP-1α (see FIGS. 16–18), it did not prevent the cells from responding to the inhibitory activity of another molecule. These results thus document the specificities and differing modes of activity of MIP-1α and H-ferritin with regards to inhibition of early myeloid progenitor cell proliferation.

Discussion

The current understanding of myeloid blood cell regulation highlights an nitricate and specific, but sometimes redundant, interaction of accessory cell roduced cytokines and the actions of these cytokines on target cells including the eterogenous populations of hematopoietic stem and progenitor cells. This is exemplified by three different but not necessarily all-inclusive situations that can modulate the growth of the same target cells. In the first, similar and perhaps related molecules can have the same action on apparently the same cells. In a second case, the same, or similar, molecules can have different actions on the same target cells. In a third situation, very different molecules can have the same or similar, effects on the same target cells. Such interactive systems most likely protect against minor regulatory defects with counterbalancing checks that maintain control elements.

The mu macrophage inflammatory proteins can be used as a model for the three situations of cytokine-cell interactions mentioned above. For the first situation, MIP-1α, MIP-1β and MIP-2 all have the capacity to enhance the proliferative effects of single, and usually suboptimal concentrations of CSF molecules (e.g., GM-CSF or M-CSF) on later more mature CFU-GM. These effects were verified using a highly purified preparation of mouse marrow CFU-GM. It is not yet clear how these enhancing effects are mediated.

In the second situation there is a dichotomy of actions of the three MIP molecules. MIP-1α, but not MIP-1β nor MIP-2, suppress proliferation of stem cells and early more immature myeloid progenitors (CFU-GEMM, and subsets of BFU-E and CFU-GM) that require more than one stimulating cytokine for a proliferative signal (e.g., Epo+IL-3, or GM-CSF+IL-3). This action was verified as a direct acting one by using highly purified populations of human myeloid progenitors (BFU-E and CFU-GM). The present studies have extended the suppressive effects of MIP-1α on myeloid progenitors to those that respond to a newly engineered rhuGM-CSF/IL-3 fusion protein which is more potent than the combined effects of rhuGM-CSF and rhuIL-3 and to MGF, the potent co-stimulating ligand for the cell surface protein produced by the c-kit proto-oncogene. In this context it is of potential importance that the more potent the proliferative signals (e.g., MGF>GM-CSF/IL-3 fusion protein>GM-CSF+IL-3>GM-CSF or IL-3), the greater the inhibitory activity detected with MIP-1α. This may simply reflect enhanced suppressive activity on more immature populations of progenitor cells.

In the present study, another characteristic of regulation by the MIP molecules is identified. MIP-1β, which has no suppressive or enhancing activity on stem or early myeloid progenitor cells, has the capacity to block the suppressive actions of MIP-1α. This adds another regulatory check to control of blood cell production made especially interesting due to the close biochemical compositions of MIP-1α and MIP-1α. In this context it is of interest that a 1:1 ratio of MIP-1β to MIP-1α did not block the inhibitory of MIP-1α, which probably explains how the natural MIP-1 (composed of MIP-1α a and MIP-1β at a 1:1 ratio) was able to manifest suppressive activity.

To define the mode of action of MIP-1α and MIP-1β on hematopoietic cells, pulsing studies for one hour were done.

These studies demonstrated that pulse exposure to MIP-1α was as effective in suppressing colony formation as continuous exposure. MIP-1β given after exposure to MIP-1α could no longer block the effects of MIP-1α. In similar studies, pulse exposure to MIP-1β prevented subsequent addition of MIP-1α from inhibiting colony formation. These results suggest that the determining effects of these molecules occur rapidly during cellular interactions, are non-reversible at least within the context of the in vitro experiments and are not due to aggregation of MIP-1α and MIP-1β. These MIP-1α/MIP-1β effects may be mediated through receptors common to both MIP molecules; this remains to be determined. While this would be extremely difficult to prove with the early progenitor cells studied here due to their low frequency in bone marrow and the very low yield of progenitors one gets after purification procedures are used, this possibility will most likely be more easily assessed using cell lines such as TLL-R8, a T-cell line, and RAW 264.7, a macrophage cell line which demonstrate receptors for rmuMIP-1α. It has been noted, that rmuMIP-1α and rmuMIP-1β each aggregate progressively when the proteins are stored at 4° C. or higher temperatures, and at high concentrations, over a period of time. The aggregation problem was minimized by using freshly purified material, stored at relatively low concentrations, but even this may still have contained aggregated forms of the MIP-1 proteins. There was no evidence that either form of rmuMIP-1 aggregates more rapidly or to a greater extent than the other form, so it is not believed that this is responsible for the MIP-1β blocking of the MIP-1α suppression. However, because of the aggregation of rmuMIP-1α, it is possible that MIP-1α may have more potent biological activity than can now be detected, especially if the aggregates of MIP-1α are inactive and/or in some way compete with monomeric forms of MIP-1α for receptor binding.

In the third situation, it was shown that MIP-1α and H-ferritin have overlapping activities as suppressor molecules on common sets of early progenitor cells. It was previously known that both molecules had suppressive effects using the same assays, with the exception that H-ferritin suppressed CFU-GM colony formation stimulated by single CSFs, cells not responsive to the suppressive effects of MIP-1α. In the present study, it is shown that the combination of MIP-1α plus H-ferritin had no further inhibition on the early multiple cytokine-stimulated progenitors than that detected with either MIP-1α or H-ferritin alone. The ability of H-ferritin to act as a suppressor molecule was linked with its capacity to manifest ferroxidase activity (conversion of iron (Fe) from a ferrous ($Fe^{+++}$) to a ferric ($Fe^{++}$) form). It was suggested that H-ferritin in this capacity might interfere with the donation of iron from transferrin to the cells, a possibility supported by the capacity of hemin, which can deliver Fe to cells in a non-transferrin form, to overcome the myelosuppressive effects of H-ferritin in vitro. The mutated form of rhuH-ferritin which lacked the ability to manifest ferroxidase activity and did not suppress colony formation, and hemin blocked the suppressive activity of the wildtype rhuH-ferritin, but did not counteract the myelosuppressive effects of MIP-1α.

The action of MIP-1β on the suppressive capabilities of ferritin and MIP-1α was compared to determine the specificity of its effects. MIP-1β blocked the effects of MIP-1α but not the effects of H-ferritin. When all three molecules are added together, suppression of colony formation is still observed, further supporting the concept that the modes of action of these inhibitors are different and that MIP-1β acts specifically to block the actions of MIP-1α.

Identification of Cell Surface Receptors for Murine Macrophage Inflammatory Protein-1α

T-lymphocytes play a central role in the immune network both as effectors and regulators. They are comprised of subsets endowed with distinct helper, suppressor, and cytolytic capabilities. These functions may be mediated by surface receptors and subset-specific immune effectors which are elaborated and secreted after stimulation with lectin or specific antigens (51). The genes for a number of the subset-specific T-cell effector molecules have been cloned, but not all activities have been correlated with the cloned genes. Identification and demonstration of such unrecognized molecules may uncover hitherto unknown functions of T-cells.

A series of T-cell subset-specific cDNAs were cloned from cloned helper T (HTL) cell L2 and cloned cytolytic T (CTL) cell L3, by employing a modified differential screening procedure (52). The deduced amino acid sequence and the characteristics of mRNA expression of cDNA clone L2G25B is disclosed herein (53). L2G25C was another cDNA clone whose amino acid sequence was 67% homologous to the L2G25B protein. These two sequences were found to be identical to the macrophage inflammatory protein-1α (MIP-1α) and -1β (MIP-1β) cDNA sequences, respectively (54). Other groups have also found cDNAs corresponding to human counterparts of MIP-1α and -1β, (55) and other mouse and human forms of 8–10 kDa cytokines, which exhibit 20 to 45% homology in amino acid sequence (56).

MIP-1α has been shown to display inflammation induction and chemokinetic activities (38) (57), as well as suppression of proliferation of immature human and mouse bone marrow myeloid progenitor cells responsive to stimulation by combinations of growth factors and enhancement of proliferation of more mature progenitors responsive to stimulation by single growth factors (37). Although the previous studies suggest a broad biological function of MIP-1α, the studies did not provide target cells to study the nature of receptor-ligand binding. Therefore, recombinant MIP-1α was purified to examine receptor-bearing cells. The nature of rMIP-1α receptor binding and some biological effects on the receptor-bearing cells have been determined.

Materials and Methods

Cells The murine cytolytic T-cell line CTLL-R8 was grown in αMEM (Gibco Laboratories, Grand Islands, N.Y.) as described (58). The murine macrophage cell line RAW 264.7 (TBI 71; American Type Culture Collection, Rockville, Md.) was grown in DMEM containing 10% fetal bovine serum (FBS), 25 mM HEPES buffer, 1 mM sodium pyruvate, 100 units/ml penicillin and 100 μg/ml streptomycin. C127 cells (CRL1616; American Type Culture Collection) were grown in DMEM containing 10% FBS and antibiotics as above. Five μg/ml Con A (Sigma, St. Louis, Mo.) for 16 hrs. RAW 264.7 cells were stimulated with 1 μg/ml of lipopolysaccharide (LPS) from *E. coli* 0127:B8 (Sigma) for 18 hrs.

Antibody Preparation

A rabbit was immunized with 50 gg of rMIP-α, emulsified in Freund's complete adjuvant. The rabbit received one intracutaneous injection in 4 foot pads and two intramuscular injections one month apart. The serum was obtained 10 days after the final injection. The antibodies recognize specifically 8 kDa band at 1:100 to 1:500 dilution in Western staining. The band was later confirmed to be MIP-1α by amino acid sequencing. The IgG fraction from rMIP-1α anti-serum was isolated by a protein A Sepharose column (Pharmacia). Polyclonal rabbit antibodies to natural (n)

MIP-1 (mixture of nMIP-1α and nMIP-1β) which recognize both rMIP-1α and rMIP-1β were kindly provided by Dr. B. Sherry (Rockefeller University, New York, N.Y.) in the beginning of these studies. The antibodies were employed to examine whether rMIP-1α is immunologically related to the NMIP-1α.

Construction and Transfection of Expression Plasmids for rMIP-1α (Recombinant L2G25B Proteins)

L2G25B cDNA, used for the construction of a rMIP-1α expression plasmid, was composed of a 5' untranslated region (45 base pairs), a complete coding region, and a 200 base pair 3' untranslated region. The L2G25B cDNA was inserted into a bovine papilloma viral vector (pBMT3X) at the Xho I insertion site, behind the metallothionein promotor, to generate pBGL2B. This construct was then used to transform C127 cells by calcium phosphate co-precipitation with dimethylsulfoxide (DMSO, Sigma) shock as described (59). The transformants were selected under the pressure of 10 $\mu$M cadmium chloride. The transformed cell colonies were recognized 7–10 days after transfection, and the cell colonies were of sufficient size to be isolated by days 14–21. Individual colonies were removed by overlaying a filter disk soaked with 0.25% trypsin/11 mM EDTA onto the transformed cells. These colonies were then transferred to 96 well tissue culture plates. About 500 clones were selected from which cell-culture supernatants were screened by an immunoblot assay. The high producer was subjected to single-cell cloning and a stable transformant C127-L2G25B48 was established.

RNA Blot Hybridization

Poly (A)$^+$ RNA from several L2G25B-transfected C127 clones was fractionated on 1.4% formaldehyde-agarose gels and transferred to Gene Screen Plus (New England Nuclear, Boston, Mass.). Gel-purified cDNA inserts were $^{32}$P-labeled by nick translation and used as probes. Filters were prehybridized and hybridized at 42° C. in 50% formamide, 5×SSC (1×SSC—150 mM NaCl, 15 mM sodium citrate, pH 7.0), 0.1% SDS, 150 $\mu$g/ml salmon sperm DNA, and 10% dextran sulfate. Filters were washed at room temperature for 30 min in 2×SSC, twice at 60° C. for 30 min in 2×SSC and 1% SDS, and again at room temperature for 5 min in 0.1×SSC. A probe pMel 14-2 was used to show that each lane contained a similar amount of RNA and that the RNA was not degraded. pMel 14-2 is a cDNA clone isolated from a human melanocyte cDNA library that has been used as a control probe because the corresponding RNA was detectable in almost equal amounts in all human and mouse cells tested.

Purification and Sequence Analysis of rMIP-1α

The serum-free culture supernatants of C127-L2G25B48 cells were concentrated 10–30 fold by the Minitan concentration system (Millipore Corp., Bedford, Mass.) and dialyzed against 20 mM Tris-Cl, pH 8.0. The proteins were partially purified through a Q-Sepharose column (Pharmacia Fine Chemicals, Rahway, N.J.) with a linear gradient of NaCl from 0.0 to 1.0 M in the same buffer. The rMIP-1α containing fractions were pooled and reconcentrated with Centricon 3 (Amicon Corp., Lexington, Mass.) and subjected to 12–20% gradient sodium dodecyl sulfate polyacrylamide gel electrophoresis (SDS-PAGE). The protein bands were visualized by staining with 0.25 M KCl and 1.0 mM DTT, and a corresponding gel piece was removed by cutting. The proteins were eluted from the gel piece and processed as described by Hager et al (60). Following SDS-PAGE, protein purities were confirmed by immunoblot analysis and Coomassie brilliant blue, silver, or amido black staining. The N-terminal sequence of pure rMIP-1α was determined by an automatic peptide sequencer.

Preparation of $^{125}$I-Labeled rMIP-1α

Purified rMIP-1α was labeled with Na $^{125}$I by utilizing the Enzymobead iodination reagent according to directions given by the manufacturer (Bio-Rad, Richmond, Calif.). Purified rMIP-1α (5 $\mu$g) and 2.5 mCi of Na $^{125}$I (ICN Radiochemicals, Irvine, Calif.) were mixed with 50 $\mu$l of Enzymobead suspension in a 1.5 ml polypropylene tube; the iodination reaction was initiated by the addition of 9 $\mu$l of 6% D-glucose solution. The iodination reaction was performed at room temperature for 30 min and was terminated by adding 25 $\mu$l of 10% sodium azide in 0.1 M sodium phosphate buffer, pH 7.0. The $^{125}$I-rMIP-1α was separated from unreacted $^{125}$I with a Sephadex G-25 column (Pharmacia Fine Chemicals, Rahway, N.J.) that was pre-equilibrated with 0.1% BSA in 0.1 M sodium phosphate buffer, pH 7.0. The 0.1 ml fractions were collected and radioactivity was measured with a gamma counter (Gamma 4000, Beckman). To test the purity of labeled rMIP-1α, 10,000 cpm of $^{125}$I-rMIP-1α was analyzed by a 12–20% SDS-PAGE, dried, and exposed to X-Omat AR film (Eastman Kodak, Rochester, N.Y.) overnight at −80° C.

Receptor Binding Assay

All binding assays were carried out with CTLL-R8 or RAW-264.7 cells that had been grown in 24-well plates as a monolayer (61). Prior to the binding experiments, the medium was removed and the cells were incubated in 10.0 mM sodium citrate, pH 4.0/0.14 M NaCl/0.1% BSA for 20 sec at 0° C. to remove endogenous ligands which had bound to the receptors (62). All assays were done in duplicate or triplicate.

For direct binding experiments on culture plates, cultures were incubated with varying concentrations of $^{125}$I-rMIP-1α in binding buffer (α-MEM or DMEM/25 mM HEPES, pH 7.3/2% BSA) in the presence or absence of a 100-fold molar excess of unlabeled rMIP-1α at 0° C. for 1 hr with gentle continuous mixing. The cell layers were then washed 3 times with ice-cold PBS, and the cells were solubilized with the addition of 0.8 ml of 1 M NaOH per well and counted. Specific bindings were calculated by subtracting counts bound in the presence of an excessive amount of unlabeled ligand from the total counts bound in the absence of unlabeled ligand.

For competitive binding experiments, Con A-stimulated CTLL-R8 cultures were incubated with 4×10$^4$ cpm radioligand and increasing concentrations of unlabeled rMIP-1α for 1 hr at 0° C., then washed, solubilized, and counted. In addition, experiments were conducted in which the incubations with radioligand were carried out in the presence of excess unlabeled human recombinant (r) IL-1α (Biogem, Cambridge, Mass.) and human rIL-2 (Sigma).

[$^3$H]thyrnidine Incorporation of CTLL-R8 Cells

CTLL-R8 cells (1×10$^5$) were plated in each well of a 96-well plate in 0.1 ml of c&MEM containing 5% FBS and culture for 8 hrs. Then purified rMIP-1α was added at various concentrations to each well. To control wells were added the buffer of rMIP-1α. When the culture supernatant of C127-L2G25B48 was added to the wells as rMIP-1α source, the control wells received culture medium of untransfected C127 cell. The cells were cultured for another 16 hours with or without the rMIP-1α; they were labeled for the last 8 hours with 1 $\mu$Ci/well [$^3$H]thymidine. The cells were harvested using a MB48R cell harvester (Biomedical Research and Development Lab, Gathesburg, Md.). The level of [$^3$H] thymidine incorporation was determined in a scintillation counter. In order to measure the blocking activity of anti rMIP-1α IgG, the rMIP-1α was reacted with the antibodies for 30 min at room temperature before addition to the CTLL-R8 cells.

Results

Production of Recombinant L2G25B Protein (rMIP-1α)

To produce rMIP-1α, C127, a mouse fibroblast cell line with a bovine papilloma viral expression vector carrying L2G25B, was transfected. The promoter of the mouse metallothionein gene directed the expression of the inserted cDNA. After selecting of cell clones resistant to cadmium chloride pressure, single cell subcloning was carried out by limiting dilution. RNA blot analysis and immunoblot assay were employed to select clones which potentially produce a high level of rMIP-1α. FIG. 21 shows an RNA blot analysis of mRNA from three such clones. Five micrograms of poly(A)$^+$ mRNA from L2G25B-transfected C127 clones (C127-L2G25B) were fractionated on a 1.4% formaldehyde-agarose gel, transferred to GeneScreen Plus, and hybridized to $^{32}$P-labeled L2G25B and pMel 14-2 cDNA sequentially. pMel 14-2 was used to compare the amount of mRNA which had been applied in each lane. Numbers on each lane are the C127-L2G25B clone numbers. Clone 48 was one of the high producers (FIG. 21). The C127-L2G25B48 clone was chosen as a stable transformant for the expression of rMIP-1α, after determining the growth rate and stability of transfected DNA under the cadmium pressure for 3 months.

FIGS. 22A–C show the expression and purification of rMIPα. FIG. 22A shows an immunoblot analysis using anti-rMIP-1α antibody (1:100). Twenty µl of each culture supernatant was applied to 12–20% linear gradient SDS-PAGE. a, C127-L2G25B48; b, RAW 264.7 which had been stimulated with 1 µg/ml of LPS for 18 hrs.; c, unstimulated RAW 264.7. FIG. 22B shows purified protein bands of rMIP-1α. Ten µl of each sample was applied to 12–20% linear gradient SDS-PAGE, transferred to Immobilon P and stained with Coomassie brilliant blue or antibodies. a, Coomassie brilliant blue staining of purified rMIP-1α; b, left half of the lane, immunostaining of rMIP-1α; right half of the lane, Coomassie brilliant blue staining of the same band. FIG. 22c shows the amino acid sequence determined from purified rMIP-1α.

The culture supernatants of C129-L2G25B48, unstimulated and LPS-stimulated RAW 264.7 were examined by immunoblot. As shown in FIG. 22A, immunoblot analysis demonstrated that rMIP-1α (FIG. 22A, lane a) migrated to the position of 8 kDa as did that of native MIP-1 from RAW 264.7 (FIG. 22A, lanes b and c). Next, the recombinant proteins were purified from the crude culture supernatants as described in Materials and Methods. Purified rMIP-1α was identified as a single species of protein with an apparent molecular weight of 8 kDa (FIG. 22B, lane a), and the identification was confirmed by immunostaining (FIG. 22B, lane b). The N-terminal sequence of purified rMIP-1α was identical to the mature protein predicted from the cDNA sequence (FIG. 22C). The level of expression was approximately 1 µg/ml of culture medium for rMIP-1α.

rMIP-1α had been assessed for effects on colony formation of immature myeloid progenitor cells in human and murine bone marrow, to examine its specific biological activity. The rMIP-1α showed a myelopoietic suppressive effect on these cells.

Radioiodination of rMIP-1α

To identify the receptor site for MIP-1α, pure rMIP-1α was labeled with $^{125}$I, as described in Materials and Methods. SDS-PAGE and autoradiography of the purified radioligand (FIG. 23) showed that all the counts were associated with a single 8 kDa band having the same mobility of rMIP-1α. $10^4$ cpm of iodinated material was applied to the 12–20% gradient gel. The molecular weight markers are indicated on the right side. Labeled protein appeared as a single band with 8 kDa molecular weight. The total radioactivity of iodinated material eluted from the Sephadex G-25 column was 5×10$^8$ cpm and ≧99% was TCA-precipitable. Assuming 100% recovery from Sephadex G-25 separation, the specific radioactivity was 10$^8$ cpin/µg of rMIP-1α. This value was used for estimating the $^{125}$I-rMIP-1α concentration in all of the binding experiments.

Receptor Binding Assay

All binding experiments were typically carried out at 0° C. to prevent possible physiological modifications that might occur during and/or after receptor-ligand binding. Since the results of preliminary experiments showed that the specific binding process reached a steady state within 1 hr (data not shown), all binding reactions were continued for one hour.

FIGS. 24A–C show a $^{125}$I-rMIP-1α binding curve and Scatchard plot analysis. Con A-stimulated CTLL-R8 cells were incubated with various concentrations of $^{125}$I-rMIP-1α in the presence or absence of 100-fold molar excess unlabeled ligand. FIG. 24A shows a binding curve. Only specific binding is shown. FIG. 24B shows a Scatchard plot analysis. The Kd obtained in this experiment shown was 1.5×10$^{-9}$M. FIG. 24C shows an inhibition of $^{125}$I-rMIP-1α binding. Con A-stimulated CTLL-R8 cells were incubated with 4'10$^4$ cpm of $^{125}$I-rMIP-1α in the presence or absence of unlabeled rMIP-1α (□) at the indicated concentrations. Data represent binding inhibition as percentages of maximum inhibition.

The results of a representative binding experiment are illustrated in FIG. 24 in which increasing concentrations of $^{125}$I-rMIP-1α were incubated with replicate cultures of Con A-stimulated CTLL-R8 cells. Nonspecific binding was determined by incubating the CTLL-R8 cells with the radioligand in the presence of a 100-fold molar excess of unlabeled rMIP-1α. A plot of specific counts bound as a function of radioligand concentration (FIG. 24A), indicates that binding is dose-dependent and saturable. Scatchard plot analysis (FIG. 24B) of the direct binding data yielded an apparent dissociation constant (Kd) of approximately 1.5×10$^{-9}$M and indicated the presence of approximately 1200 binding sites per cell. In another series of experiments with unstimulated CTLL-R8 cells, affinity, calculated as a Kd value, was almost the same as that of the Con A-stimulated ones; but, the number of binding sites per cell was approximately 600 (Table 3). LPs-stimulated RAW 264.7, which produced a significant amount of nMIP-1α, was also found to carry a receptor for MIP-1α (MIP-1α-R), 380 per cell, with a Kd value of 0.9×10$^{-9}$ M. This value is comparable to that of CTLL-R8 (Table 3). FIG. 24C shows representative results of competitive binding experiments in which cold rMIP-1α competed with $^{125}$I-labeled rMIP-1α. In such experiments, duplicate cultures of Con A-stimulated CTLL-R8 cells were incubated for 1 hr at 0° C. with $^{125}$I-rMIP-1α plus increasing concentrations of unlabeled rMIP-1α. The rMIP-1α inhibited the binding of $^{125}$I-rMIP-1α to the receptors (FIG. 24C) while human rIL-1α and rIL-2 showed no inhibition when tested at concentrations of up to 60.0 nM (data not shown).

TABLE 3

Summary of Results Obtained in Direct Binding Experiments.[a]

| Cells tested | Stimulator | Kd(M) | Receptor (sites/cell) |
|---|---|---|---|
| CTLL-R8 | None | 1.52 ± 0.36 × 10$^{-9c}$ | 590 |
|  | Con A[b] | 1.46 ± 0.32 × 10$^{-9}$ | 1191 ± 229[c] |

TABLE 3-continued

Summary of Results Obtained in Direct Binding Experiments.[a]

| Cells tested | Stimulator | Kd(M) | Receptor (sites/cell) |
|---|---|---|---|
| RAW 264.7 | None | — | —[d] |
|  | LPS[e] | $0.91 \times 10^{-9}$ | 378 |

[a]Each cell culture was incubated for 2 hrs at 0° C. with varying concentrations of $^{125}$INT-rMIP-1α in the presence or absence of 100-fold molar excess uniodinated ligand (see Materials and Methods).
[b]CTLL-R8 cells were stimulated with Con A (5 μg/ml) for 16 hrs.
[c]Results are the Mean ± SEM from two independent experiments.
[d]Undetectable.
[e]RAW 264.7 cells were stimulated with LPS (1 μg/ml) for 18 hrs.

rMIP-1α Inhibition of CTLL-R8 Cell Proliferation

Next, the effect of rMIP-1α on the growth of the CTLL-R8 cells was examined. FIG. 25A shows an inhibition of CTLL-R8 cell proliferation by rMIP-1α. CTLL-R8 cells ($1 \times 10^5$/well) were plated in a 96-well plate in 0.1 ml of αMEM containing 5% FBS. After 8 hrs of incubation, rMIP-1α was added at the concentrations indicated; 8 hrs later the cells were labeled for 8 hrs by addition of 1 μCi/well [$^3$H] thymidine. The sources of rMIP-1α were purified form (−) or culture supematant of C127-L2G25B48 ( . . . ). Points are averages of triplicates and error bars are SEMs. FIG. 25B shows a blocking of rMIP-1α effect by anti-rMIP-1α IgG. Experiments were similar to those in (A), except the number of cells were $3 \times 10^5$/well. rMIP-1α and anti-rMIP-1α IgG were mixed at the concentration indicated prior to addition to the CTLL-R8 cells. (The control wells did not receive rMIP-1α nor anti-rMIP-1α IgG). Each column indicates mean [$^3$H]-thymidine incorporation of triplicates and error bars are SEMs. Note that a higher level of anti-rMIP-1α blocks the growth inhibitory effect of rMIP-1α.

As shown in FIG. 25A, the addition of rMIP-1α showed a dramatic and dose-dependent inhibition of CTLL-R8 cell growth. The rMIP-1α contained in the culture supernatant of C127-L2G25B48 and that in the purified preparation showed comparable effect on the growth inhibition of CTLL-R8 cells at the range of rMIP-1α concentration shown in FIG. 25A. The concentration of rMIP-1α causing a half maximal inhibition was approximately 10 ng/ml. When rMIP-1α was reacted with antiMIP-1α IgG before addition to the CTLL-R8 cells, the growth inhibitory activity of the rMIP-1α was blocked in an antibody concentration dependent fashion (FIG. 25B). These data indicate that rMIP-1α has a suppressive activity on CTLL-R8 cells.

Discussion $^{125}$I-rMIP-1α binds to CTLL-R8 and RAW 264.7 with similarly high affinity. Scatchard analysis shows only one class of high affinity sites with apparent Kds of approximately $1.5 \times 10^9$M for CTLL-R8 cells and $0.9 \times 10^{-9}$ M for RAW 264.7. Unlike other receptor systems such as IL-2-R (63), there is no evidence for high- and low-affinity MIP-1α-R on CTL or macrophage cell lines.

The growth inhibition of CTLL-R8 was a second example of the suppressive activity associated with rMIP-1α, following the example of the myelosuppressive activity on the rare populations of progenitor cells in bone marrow (64). The concentration of rMIP-1α which produces 50% of maximal effect is approximately 1.2 nM. The Kd for $^{125}$I-rMIP-1α binding, which corresponds to the concentration of $^{125}$I-rMIP-1α required to saturate 50% of its binding sites, is 0.9–1.5 mM. The data from the two separate studies is in good agreement such that a 50% occupancy of the receptors produces half maximal inhibitory activity in CTLL-R8 cells. The myelosuppressive activity of rMIP-1α was also detected within the range of nanomolar concentration.

The CTLL-R8 was a cloned CTL and lost the killing activity in the course of in vitro maintenance. The cells are no longer dependent on exogenous IL-2 for growth. It is not known whether the cells make their own IL-2 or other growth factors. Therefore, whether rMIP-1α inhibits an IL-2-induced activation of CTL as demonstrated with TGF-β is not known. It will be interesting to examine whether MIP-1α acts on T-lymphocytes in general or on a subset of T-lymphocytes. It will be also important to determine whether MIP-1α has any immunosuppressive effects in animals.

rMIP-1α has a tendency to aggregate itself as its natural form (38). Apparently, ionic interactions between acidic and basic regions of the molecule lead to the formation of large aggregates in solutions at physiological ionic strength. The aggregates can be disrupted by increasing the ionic strength with 500 mM NaCl.

The extent of aggregates of rMIP-1α was evaluated by filtration through Centricon-30 (30 kd cut-off filters; Amicon, Beverly, Mass.). Western blot analysis of the filtrate showed that approximately 5% rMIP-1α was smaller than 30 kDa when the C127-L2G25B48 culture medium was tested immediately after harvest. After the conditioned medium had been stored at 4° C. for 2 weeks, no rMIP-1α could be detected in the filtrate of Centricon-30.

The data reflects specific binding of the small fraction of unaggregated rMIP-1α. It is not known if the aggregated material is still capable of binding to the receptor. The inherent tendency of aggregation may lead to deviations from normal receptor binding kinetics. The fact that 50% receptor occupancy is required to achieve a half maximal inhibition may be due in part to the aggregation problem because this is considerably more than is necessary for other cytokines. The potential caveat should be considered with regard to the estimation of the number of receptors and their affinity. Likewise, this property may lead to the considerable underestimation of the bioactivity of MIP-1α. In spite of these limitations, it is clear that CTLL R-8 cell has specific receptors for MIP-1α and responds to this cytokine.

A search was done for cells of bone marrow origin which may bear receptors for rMIP-1α. Bone marrow stem cell lines, KG-1a (65), 416B (66), and DU528 (67) cells, failed to bind rMIP-1α even though the total bone marrow cells showed a low level of rMIP-1α binding (data not shown).

The pathways mediating the growth inhibition by rMIP-1α need to be fully explored by molecular cloning of the receptor and by elucidation of the nature of receptor-mediated signal transduction. Having responsive, homogenous cell line now offers the possibility of studying signal transduction, not possible previously with normal bone marrow due to the rareness (approximately ⅟500 to ⅟1000) of myeloid progenitors in the heterogeneous population of marrow and the difficulty of getting a high enough yield of purified progenitors.

Myelosuppressive Effects In Vivo of Purified Recombinant Murine Macrophage Inflammatory Protein-1 Alpha Hematopoietic stem and progenitor cell proliferation and differentiation is regulated by cytokines derived from accessory cells (36). These cytokine mediators have been implicated in the enhancement and/or suppression of myelopoiesis stimulated by colony stimulating factors (CSFs). A member of this group is the heparin-binding murine (mu) macrophage inflammatory protein, MIP-1, originally identified for its capacity to cause a localized inflammatory reaction after injection into the footpads of C3H/HeJ mice (38). MIP-1 is part of a larger family of molecules variously termed, small inducible proteins and intercrine cytokines (39) (40, 68). Purified natural preparations of muMIP-1 are composed of two distinct peptides, MIP-1α and MIP1β. Natural muMIP-1, as well as recombinant (r) muMIP-1α and rmuMIP-1 have enhancing activity for the more mature murine bone marrow granulocyte-macrophage progenitor cells (CFU-GM) stimulated by murine granulocyte-macrophage (CSF) (GM-CSF) or murine macrophage CSF (M-CSF) and human marrow CFU-GM stimulated by human GM-CSF. Enhancing activity is most apparent when sub-optimal amounts of CSF are used to stimulate CFU-GM (69). Neither natural nor recombinant preparations of the muMIP-1 peptides have any effect on colony formation by erythroid progenitor cells (BFU-E) stimulated with erythropoietin alone. However, MIP-1α suppresses day 12 CFU-S ex vivo and CFU-A (70), as well as murine and human growth factor-stimulated multipotential progenitor cells (CFU-GEMM) and sub-populations of BFU-E and CFU-GM in vitro (71). MIP-1α suppresses progenitors that are stimulated to proliferate by combinations of cytokines, indicating that MIP-1α may act as a suppressive cytokine on more immature progenitor cells, which are stimulated by multiple cytokines, as opposed to more mature progenitor cells which are stimulated by single CSFs. The present studies were undertaken to evaluate the efficacy of action in vivo of exogenously administered purified rmuMIP-1α, and to compare this with effects of rmuMIP-1β.

Materials and Methods

Mice

C3H/HeJ mice were purchased from Jackson Laboratories, Bar Harbor, ME and housed in a conventional animal facility. C3H/HeJ mice were injected intravenously (i.v.) with either 0.1 ml sterile pyrogen-free saline, purified nnuMIP-1α, or purified rmuMIP-1β diluted in sterile pyrogen-free saline. C3H/HeJ mice are relatively insensitive to the effects of bacterial endotoxin and thus would not respond to small amounts of endotoxin, below detectability of the limulus assay, that might be present in the MIP preparations.

Cytkines rmuMIP-1α and rmuMIP-1β were expressed in *Saccharomyces cerevisiae* and purified to homogeneity according to methods established for the natural proteins. rmuMIP-1α from T lymphocytes was used. The recombinant L2G25B protein, a T cell-derived MIP-1α, was produced using a bovine papilloma virus expression system. The protein was purified through Q-Sepharose (Pharmacia), preparative SDS-polyacrylamide gel, and SDS-buffer elution method (72). The final product was dissolved in 6 mol/L guanidine HCl and renatured. rmuMIP-1α from both macrophage and T lymphocyte derivation were equally active in vitro and in vivo and the results using both preparations have been combined in this paper.

Analysis of Hematopoietic Progenitor Cells In Vitro

The in vitro assays for FU-GM, BFU-E, and CFU-GEMM were performed as described (73). CFU-GM colony formation (>50 cells/group) was stimulated in 0.3% agar culture medium by using 10% (vol/vol) pokeweed mitogen mouse spleen cell-conditioned medium (PWMSCM) as a stimulus. BFU-E and CFU-GEMM colony formation were stimulated in 0.9% methyl cellulose culture medium with 1 unit erythropoietin (Amgen, Thousand Oaks, Calif.), 0.1 mmol/L hemin (Eastman Kodak, Rochester, N.Y.), and 1% PWM-SCM. Bone marrow and spleen cells were plated at respective concentrations of $7.5 \times 10^4$ and $1.0 \times 10^6$ cells/ml. Cells were incubated in a humidified environment at lowered (5%) oxygen tension and colonies were scored after five to seven days of incubation. For the dose-response study, mice were sacrificed 24 hours after treatment. This has previously shown to be an appropriate time to evaluate for the suppressive effects of other cytokines (47, 74).

Cycling Status of Hematopoietic Progenitor Cells

The proportion of progenitors in DNA synthesis (S-phase of the cell cycle) was estimated as reported previously. The high-specific activity (20 Ci/mmol), tritiated-thymidine (50 uCi/ml, New England Nuclear, Boston, Mass.) kill technique was used and is based on calculation in vitro of the reduction in the number of colonies formed after pulse exposure of cells for 20 minutes to "hot" tritiated thymidine as compared with control (McCoy's medium or a comparable amount of "cold" thymidine).

Statistical Analysis

Three plates were scored for each CFU-GM sample, and three to four plates were scored for each BFU-E/CFU-GEMM sample. Each mouse was evaluated separately. Results are expressed as a mean ±1 SEM, and these are derived from the averages of each of the individual mice within a group. The probability of significant differences between groups was determined with the use of Student's t test (2-tailed).

Results

Figure 26A:
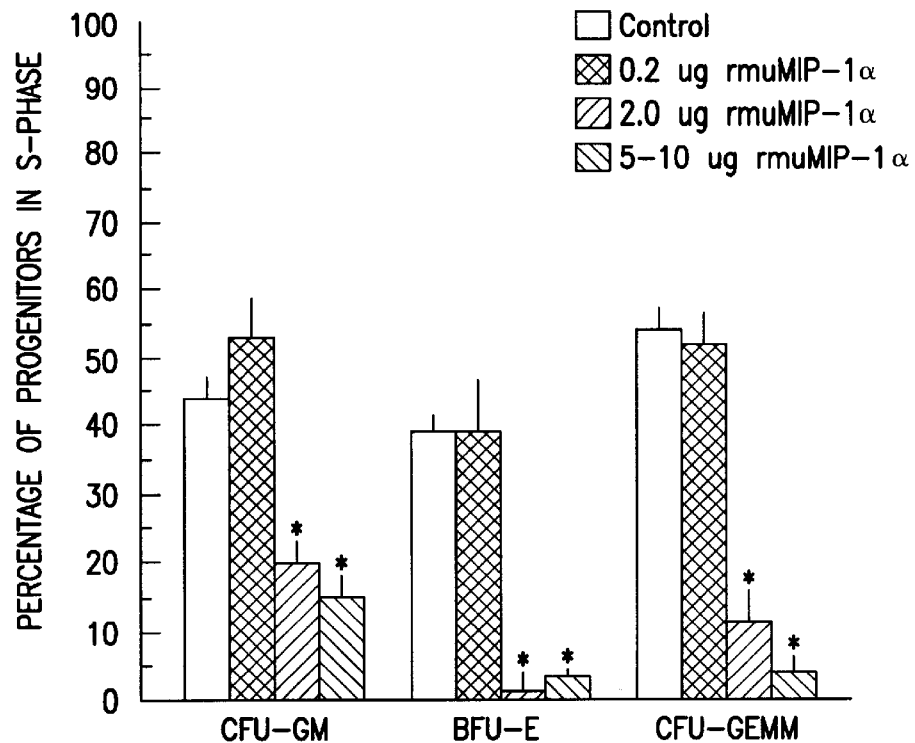
Figure 26B:
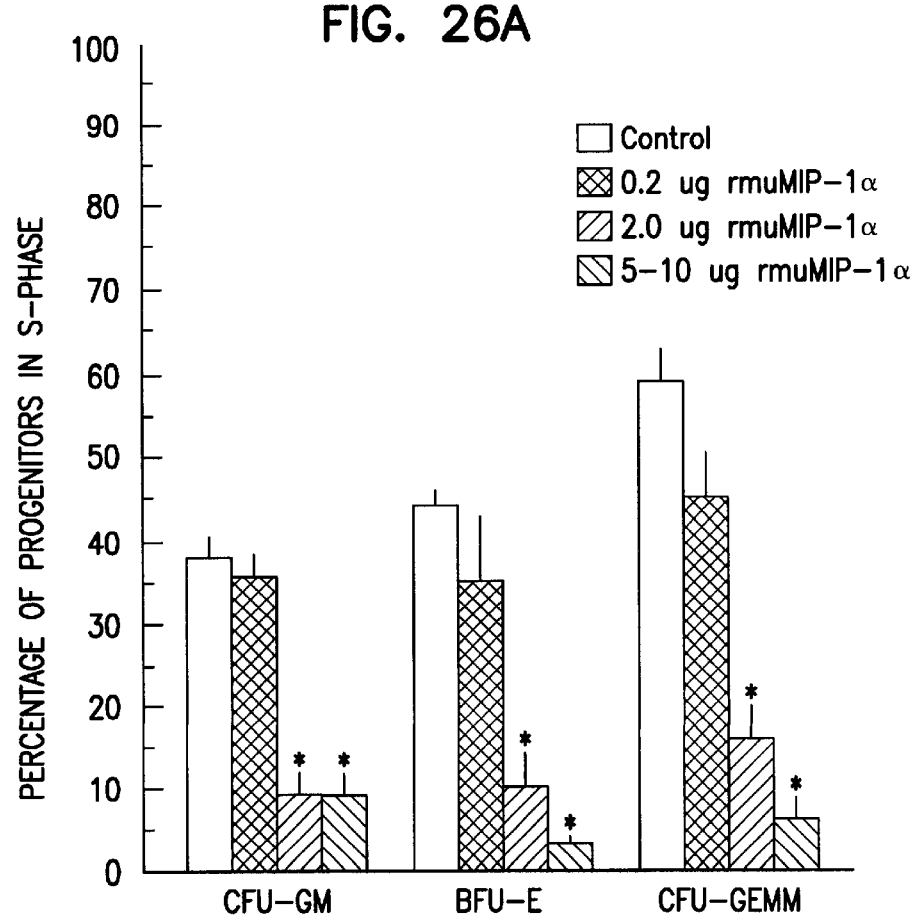

Influence In Vivo of Varying Dosages of rmuMIP-1α on Cycling Status and Absolute Numbers of Hematopoietic Progenitor Cells C3H/HeJ mice were assessed 24 hours after a single dose i.v. injection of 0.2 to 10.0 ug rmuMIP-1α for effects on the cycling rates (percentage of cells in S-phase of the cell cycle) of femoral bone marrow (FIG. 26A) and splenic (FIG. 26B) CFU-GM, BFU-E, and CFU-GEMM. FIG. 26 shows the influence of varying the dosages of rmuMIP-1α on the cycling rates (percentage of cells in S-phase) of myeloid progenitor cells in the marrow (A) and spleen (B) of C3H/HeJ mice. Results shown are the mean±S.E.M. of mice used in one to five experiments. Number of mice/group (number of experiments): BM—CFU-GM: control, 28(8); 0.2 μg 13(3); 5–10 μg 20 (6). BM—BFU-E/CFU-GEMM: Control 20(6); 0.2 μg 4(1); 2.0 μg 4(1); 5–10 μg 20(6). Spleen—CFU-GM: Control 28(8); 0.2 μg 4(1); 2.0 μg 13(3); 5–10 μg 20(6). Spleen—BFU-E/CFU-GEMM: Control 17(5); 0.2 μg 4(1); 2.0 μg 4(1); 5–10 μg 17(5). Significantly different from control: *, p<0.001; other values not significantly different, p>0.05. Bone marrow and splenic CFU-GM, BFU-E and CFU-GEMM in mice receiving sterile pyrogen-free saline were in rapid cycle (38% to 59% of the cells in S-phase), while the marrow and splenic CFU-GM, BFU-E, and CFU-GEMM of mice receiving 2.0 to 10 ug rmuMIP-1α were placed into a slow or non-cycling state. No significant effects were apparent in the mice receiving 0.2 and 1.0 ug (data not shown).

Figure 27A:
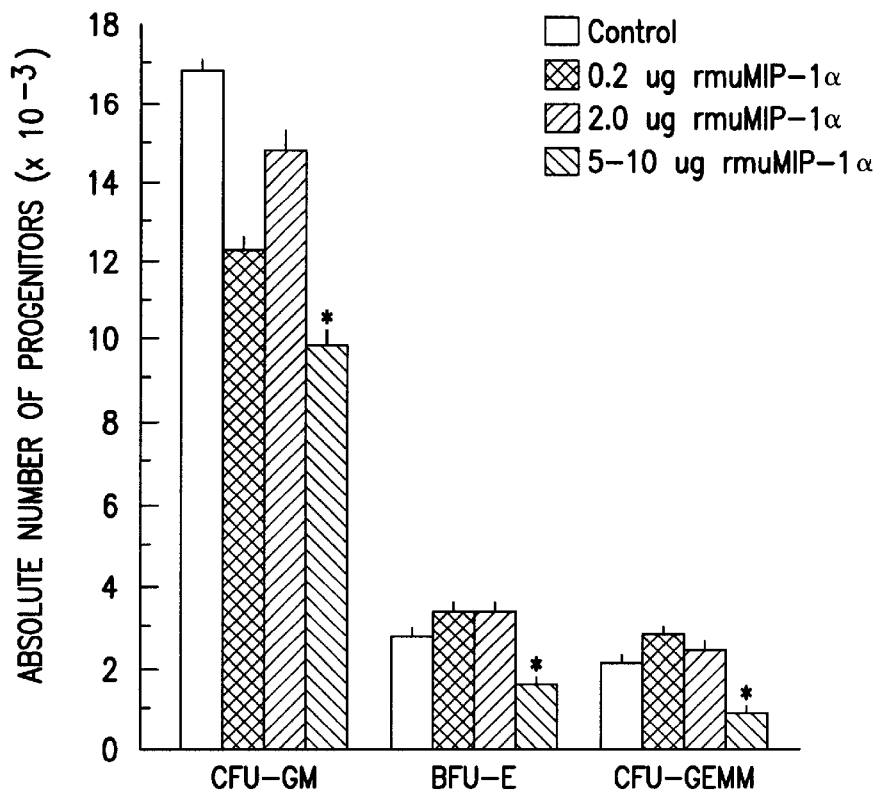
Figure 27B:
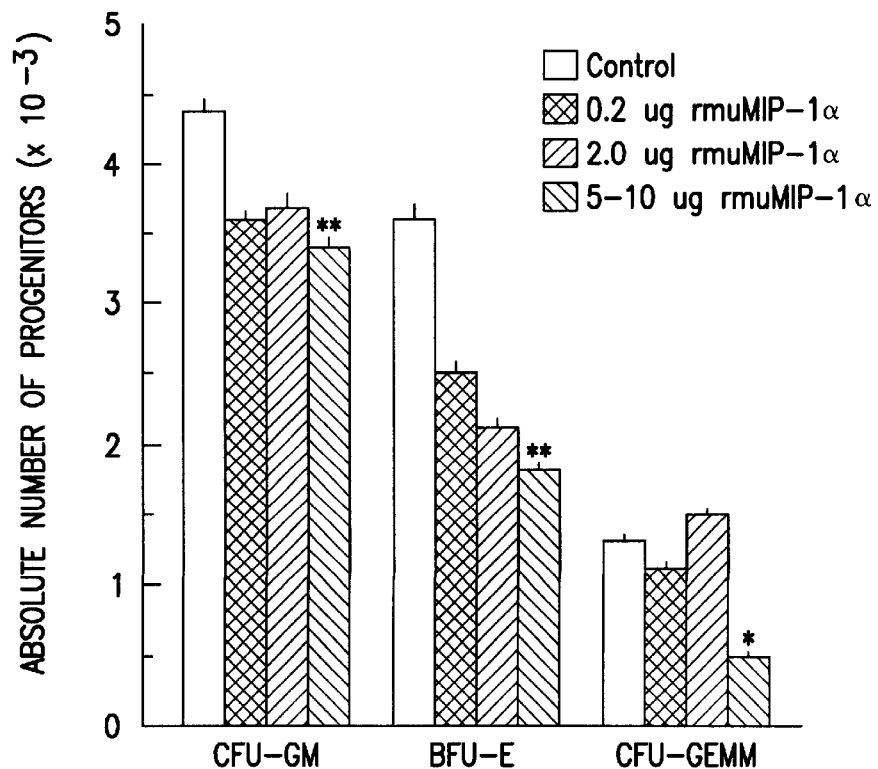

When the absolute numbers of progenitor cells were evaluated, 5.0 to 10 ug rmuMIP-1α had the greatest suppressive effect on marrow (FIG. 27A) and splenic (FIG. 27B) CFU-GM, BFU-E, and CFU-GEMM. FIG. 27 shows the influence of varying dosages of rmuMIP-1α on the absolute numbers of myeloid progenitor cells in the marrow (A) and spleen (B) of C3H/HeJ mice. Mice and conditions are the same as those shown in FIG. 26. Significantly different from control: **, p<0.05; *, 0<0.001. The absolute numbers of nucleated cells in both the bone marrow and spleen were not significantly effected (p>0.05) as compared to control mice. (Control cellularities for femoral marrow and spleen were respectively 14±0.4 and 86±5, each in millions.)

Figure 28A:
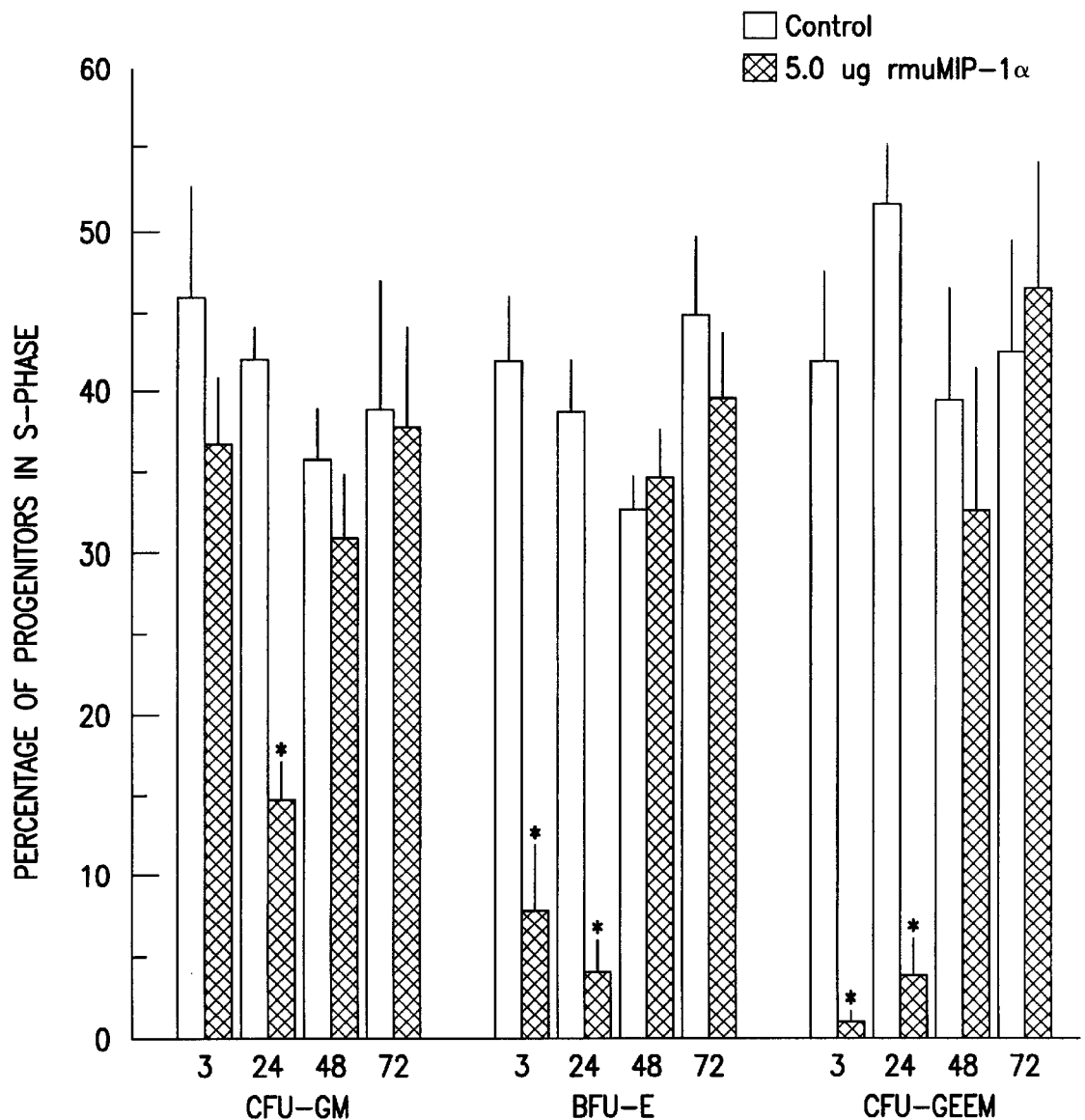
Figure 28B:
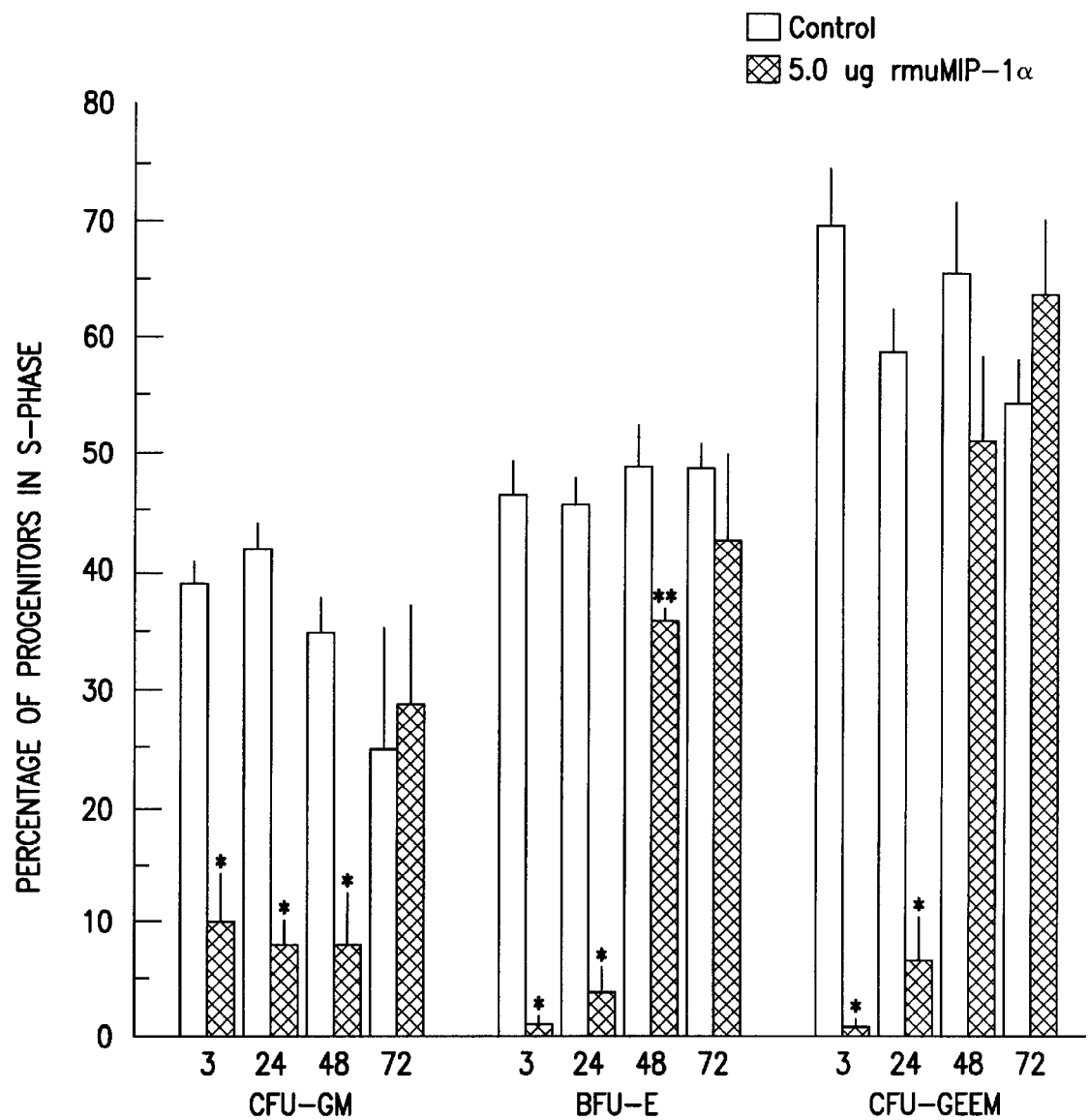

Time Sequence Study of the Effects of rmuMIP-1α on the Cycling Status and Absolute Numbers of Hematopoietic Progenitor Cells A time sequence study of the effects of a single i.v. injection of 5.0 ug rmuMIP-1α demonstrated that the suppressive effects were time dependent and reversible (FIGS. 28 and 29). FIG. 28 shows a time sequence study of the effects of rmuMIP-1α on the cycling rates (percentage of cells in S-phase) of myeloid progenitor cells in the marrow (A) and spleen (B) of C3H/HeJ mice. Results shown are the mean±S.E.M. of mice used in two to five experiments. Number of mice/group (number of experiments) at each time point: BM—CFU-GM and BFU-E/CFU-GEMM—3 hr: 9 mice/point (2); 24 hr: 16 mice/point (5); 48 hr: 9 mice/point (2); 72 hr: 9 mice/point (2). Spleen—CFU-GM: 3 hr: 9 mice/point (2); 24 hr: 16 mice/point (5); 48 hr: 9 mice/point (2); 72 hr: 9 mice/point (2). Spleen—BFU-E/CFU-GEMM: 3 hr: 3 mice/point (1); 24 hr: 16 mice/point (5); 48 hr: 3 mice/point (1). Significantly different from control: **, p<0.05; *, p<0.001. In the bone marrow (FIG. 28A) and spleen (FIG. 28B), mice injected with 5.0 ug rmuMIP-1α had CFU-GM, BFU-E, and CFU-GEMM that were placed into a slow or non-cycling state (<15% of the cells in S-phase) within 3 to 24 hours, compared to mice injected with saline (33% to 70% of the cells in S-phase), and returned to that of control values within 48 hours.

Figure 29A:
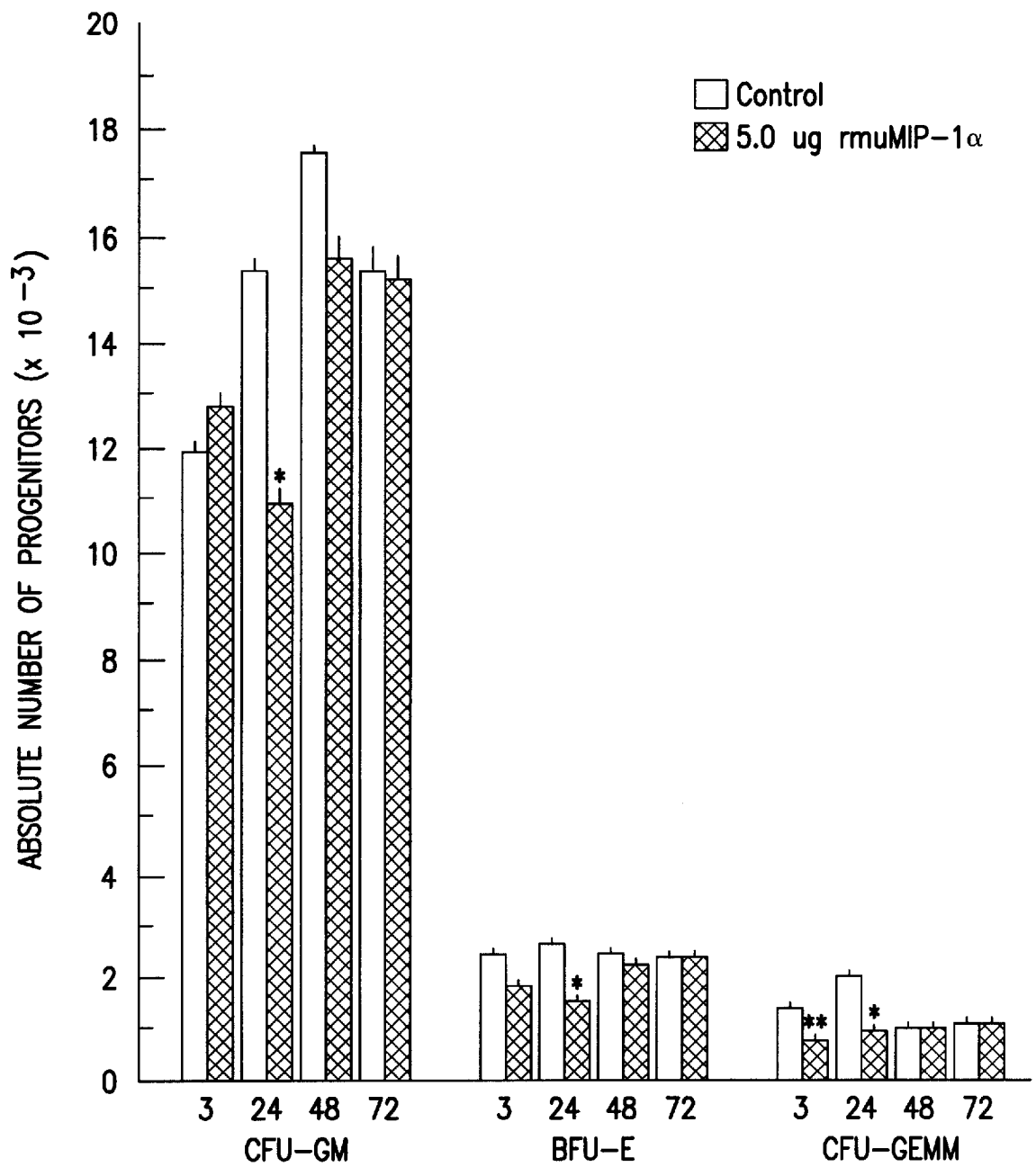
Figure 29B:
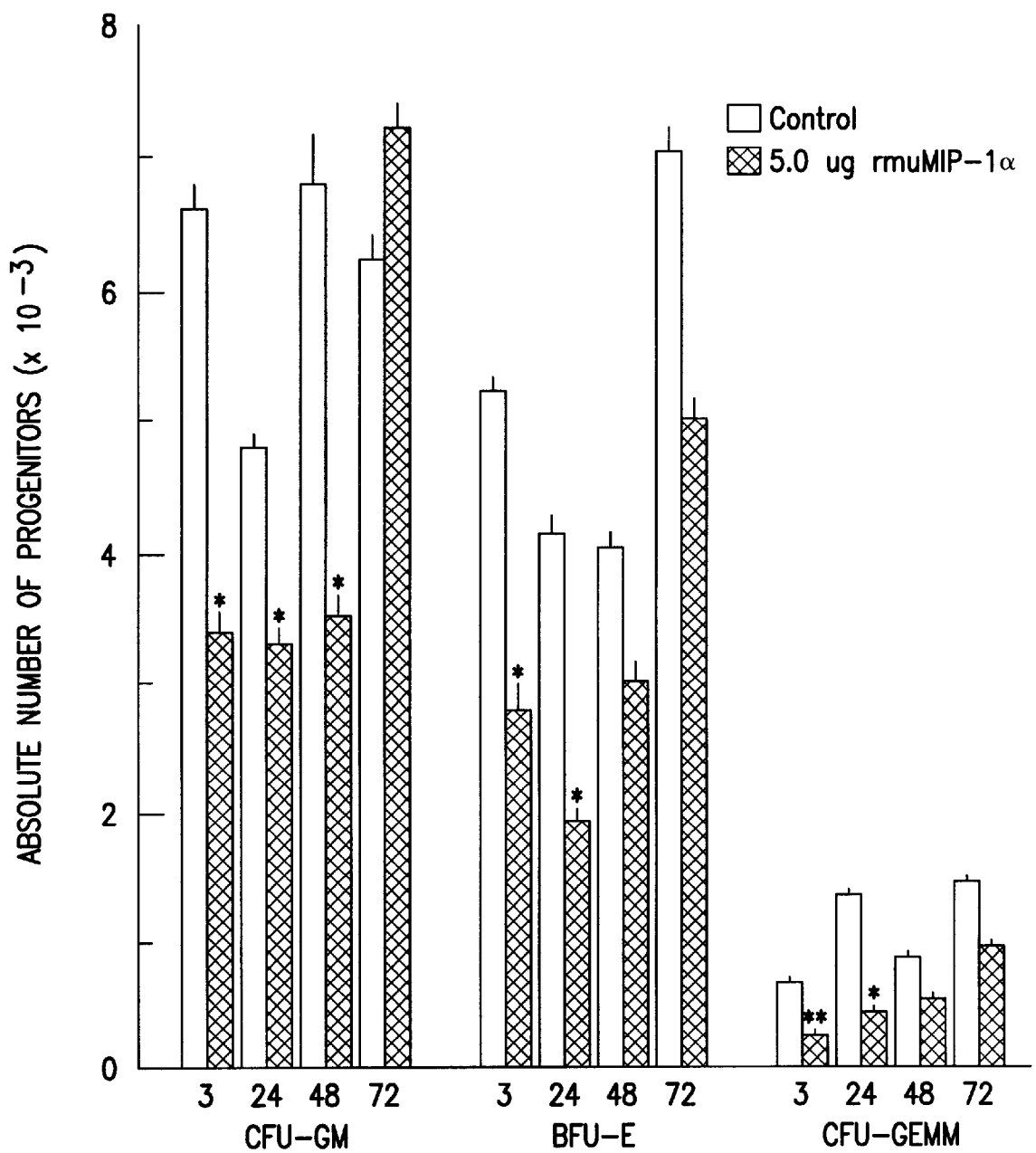

FIG. 29 shows a time sequence study of the effects of rmuMIP-1α on the absolute numbers of myeloid progenitor cells in the marrow (A) and spleen (B) of C3H/HeJ mice. Mice and conditions are the same as those shown in FIG. 28. Significantly different from control: **, p<0.05; *, p<0.001. The absolute numbers of marrow CFU-GEMM were significantly decreased within 3 hours, however, marrow CFU-GM and BFU-E were not significantly decreased until 24 hours after administration of rmuMIP-1α (FIG. 29A). Significant suppressive effects on the absolute numbers of splenic CFU-GM and BFU-E, and CFU-GEMM (FIG. 29B) were apparent within 3 hours, and diminished by 72 hours, after the administration of rmuMIP-1α.

Influence of rmuMIP-1α on Peripheral Blood Nucleated Cell Counts

Circulating leukocyte counts were evaluated in C3H/HeJ mice from 3 to 72 hours after a single injection of 5.0 ug rmuMIP-1α (Table 4). While no significant differences in the total number of peripheral leukocytes were apparent, there was a 50% decrease in the number of circulating polymorphonuclear neutrophils (PMN) at 48, but not at 3, 24, or 72, hours. No significant alteration in the number of peripheral lymphocyte or monocyte counts were apparent at any of the time points evaluated.

TABLE 4

Influence In Vivo of rmuMIP-1α on Circulating Levels of Nucleated Leukocytes

| | Nucleated Cells × $10^{-6}$/ml | | | |
|---|---|---|---|---|
| | WBC | PMN | Mono | Lymph |
| 3 hr | | | | |
| saline | 9.7 ± 0.7 | 2.5 ± 0.2 | 0.2 ± .05 | 6.9 ± 0.5 |
| rmuMIP-1α | 8.2 ± 0.5 | 2.2 ± 0.2 | 0.3 ± .04 | 5.5 ± 0.3 |
| 24 hr | | | | |
| saline | 7.8 ± 0.5 | 2.2 ± 0.2 | 0.2 ± 0.2 | 5.4 ± 0.3 |
| rmuMIP-1α | 7.5 ± 0.5 | 2.2 ± 0.2 | 0.2 ± 0.2 | 5.1 ± 0.3 |
| 48 hr | | | | |
| saline | 7.0 ± 0.5 | 2.2 ± 0.2 | 0.1 ± .03 | 4.6 ± 0.3 |
| rmuMIP-1α | 6.5 ± 0.4 | 1.1 ± .04* | 0.1 ± .03 | 5.3 ± 0.4 |
| 72 hr | | | | |
| saline | 6.7 ± 0.4 | 1.9 ± 0.2 | 0.2 ± .02 | 4.5 ± 0.2 |
| rmuMIP-1α | 6.8 ± 0.7 | 2.0 ± 0.2 | 0.2 ± .04 | 4.6 ± 0.4 |

Mice were injected i.v. with sterile pyrogen-free saline or 5.0 ug rmuMIP-1α in a volume of 0.1 ml. Results shown are averages of six mice each from a total of two experiments for each time point.
*Significant decrease from the saline-treated group, p < 0.001.

Comparative Study of rmuMIP-1α vs rmuMIP-1β

In order to evaluate the specificity of action in vivo of MIP-1α on myelosuppression, the effects of rmuMIP-1α were compared to that of rmuMIP-1β. FIG. 30 shows the comparative influence of rmuMIP-1α and rmuMIP-1β on the cycling rates (percentage of cells in S-phase) of myeloid progenitor cells in the marrow (A) and spleen (B) of C3H/HeJ mice. Results shown are the mean±1 S.E.M. from three experiments, with a total of nine mice/group evaluated 24 hrs after i.v. administration of saline, rmuMIP-1α, or rmuMIP-1β. Significantly different from control: *, p<0.001; other numbers are not significantly different from control, p>0.05. C3H/HeJ mice were administered either a single i.v. injection of saline, 5.0 ug rmuMIP-1α, or 5.0 ug rmuMIP-1β and evaluated 24 hours later for responses in the cycling of bone marrow and splenic CFU-GM, BFU-E, and CFU-GEMM (FIG. 30) and the absolute numbers of progenitor cells in the bone marrow and spleen (FIG. 31). FIG. 31 shows the comparative influence in vivo of rmuMIP-1α and nmuMIP-1β on the absolute numbers of myeloid progenitor cells in the marrow (A) and spleen (B) of C3H/HeJ mice. Mice and conditions are the same as those shown in FIG. 30. Significantly different from control: **, p<0.05; *, 0 <0.001. RmuMIP-1α, but not rmuMIP-1β, decreased the cycling rates and absolute numbers of femoral marrow and splenic CFU-GM, BFU-E, and CFU-GEMM.

Discussion

The present studies have extended those previously published regarding the in vitro and ex vivo myelosuppressive effects of MIP-1α by demonstrating this activity in vivo after a single i.v. injection of rmuMIP-1α in C3H/HeJ mice. In vitro, MIP-1α exerts a selective and apparently direct-acting ability to suppress multiple growth factor-stimulated proliferation of CFU-GEMM and earlier, more immature sub-populations of BFU-E, and CFU-GM. In the mouse, the spleen and the marrow are major hematopoietic organs. In vivo administration of rmuMIP-1α rapidly decreased the cycling rates and absolute numbers of myeloid progenitor cells in both the bone marrow and the spleen. These effects were dose-dependent, time related, reversible, and were not seen with rmuMIP-1β, a biochemically similar molecule to rmuMIP-1α but not significantly active in vitro as a suppressor. A reversible 50% decrease in the circulating levels of mature neutrophilic granulocytes was apparent 48 hours after the injection of rmuMIP-1α, consistent with the above noted suppressive effects on the myeloid progenitor cells.

This adds rmuMIP-1α to the list of other cytokines with myelosuppressive activity in vivo, which includes lactoferrin, H-ferritin, inhibin (75) and transforming growth factor (TGF)-β (76). While it is not possible to determine the mechanisms by which these myelosuppressive agents act based on results obtained in vivo, in vitro studies suggest differences in their modes of action (77). Lactoferrin suppresses the release of growth factors, including IL-1, from mononuclear phagocytes in vitro, but has no direct suppressive effects on progenitor cell proliferation/differentiation. Administration of CSFs to mice in vivo overcomes the myelosuppressive effects of lactoferrin administration to these mice. H-ferritin has direct myelosuppressive effects in vitro on both early and more mature myeloid progenitors, an effect at least in part due to the capacity of H-ferritin to manifest ferroxidase activity. Inhi in suppresses in vitro colony formation of BFU-E and CFU-GEMM by exerting its effects on a monocyte/T-lymphocyte axis presumably by decreasing production/release of growth factors. TGF-β has direct myelosuppressive effects on early progenitor cells and enhancing activity on more mature progenitors. In vitro, MIP-1α has enhancing activity directly on myeloid progenitors, and direct acting suppressive effects on earlier progenitor cells; these differential activities of MIP-1α are similar to those noted by others for TGF-β. Under the conditions chosen in this series of in vivo experiments, the suppressive effects of MIP-1α were dominant; no enhancement of myelopoiesis was noted in the mouse model reported herein. The suppressive effects of rmuMIP-1α in vivo may be mediated by direct actions at the level of the myeloid progenitors, and possibly also on earlier cells, which would be consistent with the activities of this molecule in vitro and ex vivo. Alternatively, or in addition, MIP-1α may have indirect myelosuppressive effects in vivo, mediated through actions on accessory cells. At present there is no evidence for accessory cell mediated effects of MIP-1α in vitro, although MIP-1α has suppressive effects on a mouse T-cell line in vitro. The interacting network of cytokine mediated effects on production/release of cytokines by accessory cells leaves open the possibility of indirect MIP-1α effects in vitro and in vivo.

We have found that purified rmuMIP-1 a exists in both monomeric and polymerized form when placed into phosphate buffered saline.[4] Under these conditions most MIP-1α exists primarily in polymerized form, but it is the monomeric form that is the active myelosuppressive component of the MIP-1α preparation. The polymerized form of MIP-1α does not appear to interfere with the suppressive activity of MIP-1α in vitro. This suggests that rmuMIP-1α is more active in vitro than previously reported, and that when enough monomeric MIP-1α can be isolated to test an in vivo model it will probably be more active on a weight basis than was demonstrated for the total MIP-1α preparation used in the present study.

Regardless of the mechanisms of action of rmuMIP-1α in vivo, the dosage-dependent, time-related and reversible myelosuppressive effects of nmuMIP-1α show that MIP-1α can be used in protecting normal hematopoietic progenitors during chemotherapy and/or radiation therapy. Preclinical studies in accordance with standard procedures would determine maximum effective dosages in a chemotherapy/radiation therapy setting, alone or in combination with other therapies. In general, optimal dosages would be determined for mice and then the dosages would be scaled up for use with human patients. Since MIP-1α has proinflammatory actions in mice, patients would need to be closely monitored for side effects after administration of MIP-1α in vivo.

Macrophage Inflammatory Protein-1α Inhibits the AntiCD3 mAb-Mediated Proliferation of T Lymphocytes Macrophage inflammatory protein-1α (MIP-1α) is a member of so-called intercrine cytokine family which produces a wide range of biological activities (40). The reported bioactivities include a localized inflammatory reaction (38), a prostaglandin-independent pyrogen (57,78), a potential role in wound healing (79), and a suppression of immature bone marrow stem cell (37,80). The MIP-1α cDNA was isolated from the activated T cell cDNA library by differential screening procedure (49,52). Since then its effect on T cells and immune regulation has been studied. MIP-1α inhibited the proliferation of a T cell line, CTLL-R8 (81), and the T cell line carried high affinity (a Kd of $1.5 \times 10^9$ M) receptors for MIP-1α. The number of receptors was increased when the T cells were stimulated with concanavalin A. In the present study, the effect of MIP-1α and the mode of modulation of its receptors in the resting splenic T cells is examined.

Materials and Methods

Separation of Murine Spleen T Cells

The resting murine splenic T cells were enriched by nylon wool and Percoll gradient centrifugation (82). Briefly, the spleen cells of female BALB/c mice (Harlan, Indianapolis, Ind.) were adjusted to $1.5 \times 10^8$/ml in RPMI 1640 containing 2% fetal bovine serum (FBS). A 10 ml nylon wool column was prewashed with phosphate buffered saline (PBS) and RPMI 1640 containing 2% FBS, and incubated at 37° C. for 20 min before use. The spleen cells were loaded onto the column and washed the column with the above medium. The eluted cells subsequently were fractionated by centrifuging the cells at 2000×g at 4° C. for 30 min on 50–100% Percoll step gradient. The resting T cell fraction was recovered from the interface between the 50% and 80% Percoll. The enrichment of T cells were examined with EPICS Profile Analyzer (Coulter Corporation); ~91% were Thy $1.2^+$, ~52% were $L^3T^{4+}$ and 24% were $Lyt^+$.

AntiCD3 mAb-Mediated T Cell Activation

AntiCD3 monoclonal antibody (mAb) (clone 2C11) was immobilized on cell culture dishes or plates at 10 μg/ml concentration for 3 hrs at 37° C. The enriched resting T cells were added to antiCD3 mAb coated wells and cultured for indicated periods of time.

Iodination of Murine (m) Recombinant (r)MIP-1α

3 μg of mrMIP-1α was used for [$^{125}$I] labeling with the Bolton-Hunter reagent (NEN), according to a modified procedure described by Rizzino and Kozokoff (83). mrMIP-1α was purified from serum-free culture supernatant of C127-L2G25B48 cells which carried an MIP-1α. cDNA in a bovine papilloma viral expression vector. For certain experiments commercial mrRMIP-1α (R and D systems, Minneapolis, Minn.) was used. Essentially the same results were achieved with the R & D product. The [$^{125}$I]mrMIP-1α was separated from free [$^{125}$I] by the use of a Sephadex-G25 column (Pharmacia Fine Chemicals, Piscataway, N.J.) that was pre-equilibrated with 0.2% gelatin in 5 mM acetic acid. The 0.3 ml fractions were collected and 10 μl of each fraction were precipitated by 15% TCA on glass microfine filters and the radioactivity was measured with a gamma counter (Gamma 4000 Beckman). The specific activity of the [$^{125}$I]mrMIP-1α was $1.0 \times 10^8$ cpm/ug.

Receptor Binding Assay

All receptor binding assays were carried out with enriched resting splenic T cells. Prior to binding assay, the cells were washed with acidic buffer (10 mM sodium citrate pH 4.0/ 0.14 M NaCl/0.1% BSA) for 20 secs at 0° C. to remove the endogenous ligands that might have bound to the receptors (62). The cells were resuspended in binding buffer (Hank's balanced salt solution/25 mM HEPES pH 7.5/1% BSA) and the cell number was adjusted to $8\times10^6$/ml. The T cells were incubated with varying concentrations of [$^{125}$I]mrMIP-1α in the presence or absence of 100-fold molar excess of unlabeled mrMIP-1α at 4° C. for 2 hrs with gentle rotation. The reaction was stopped by adding 0.5 ml of cold binding buffer. 100 ul aliquot was separated into bound and free [$^{125}$I]mrMIP-1α by centrifugation through 1.5/1.0 (V/V) mixture of dibutyl phtholate/dioctyl phtholate at 14,000 rpm for 3 min (84). The tubes were frozen and the cell pellets were separated from the supernatant by slicing the tube. The radioactivities of both cell pellets and supernatants were counted. Specific binding was calculated by subtracting counts bound in the presence of an excessive amount of unlabeled ligand from the total counts bound in the absence of unlabeled ligand.

Internalization of Receptor-Bound mrMIP-1α

The splenic T cells were incubated with [$^{125}$I]mrMIP-1α for 2 hr at 4° C. After incubation cells were cultured in RPMI-1640 with 10% FBS. Aliquots of cell suspension were added to wells coated with antiCD3 mAb or uncoated wells. At indicated times, the cells and medium were collected. The medium was mixed with 1:1 volume of 20% trichloroacetic acid (TCA) on ice. TCA soluble and insoluble fractions were separated by centrifugation at 2.000×g at 4° C. for 20 min. The cell pellets were resuspended in 10 mM Glycine-HCl buffer (pH 2.5) to remove surface-bound [$^{125}$I]mrMIP-1α (85). The cell pellets were counted to determine the internalized radioactivity.

Northern Blot Analysis

Total RNA from mouse splenic T cells stimulated with antiCD3 mAb was isolated using a guanidinium thiocyanate-phenol-chloroform extraction procedure (86). Twenty μg of total RNA from each sample were fractionated on 1.4% formaldehyde-denaturing agarose gels and transferred to GeneScreen Plus membrane (New England Nuclear, Boston, Mass.). L2G25B cDNA which encodes murine MIP-1α was radiolabeled using the method of random hexanucleotide priming. Filter was prehybridized and hybridized at 42° C. in 50% formamide, 5×SSC, 0.1% SDS, 150 μg/ml salmon sperm DNA, and 10% dextran sulfate. Filter was washed at room temperature twice in 2×SSC for 20 min each, once in 2×SSC at 68° C. for 60 min and again at room temperature for 30 min in 0.2×SSC and 0.1% SDS.

Immunoblot Analysis

Mouse splenic T cells were cultured in antiCD3 mAb-coated petri dishes with serum free medium (HB 101) (Irvine Scientific, Santa Ana, Calif.). The culture medium was concentrated by TCA precipitation. The proteins were fractionated on 15% polyacrylamide SDS gels and transferred electrophoretically onto Immobilon P (Millipore, Bedford, Mass.). The membrane was stained with rabbit anti-rMIP-1α antibodies and alkaline phosphatase-conjugated secondary antibodies (Zymed, Inc., San Francisco, Calif.).

Biotinylation of MIP-1α and Immunocytochemistry

One μg of mrMIP-1α was biotinylated with 1 μg of Aminohexanoyl-Biotin-N-hydroxysuccinimide (AM-BNHS, Zymed Lab, Inc.) in 20 μl of 0.1 M sodium bicarbonate, pH 8.4 at room temperature. Following addition of 60 μl of 1% gelatin, the biotinylated mrMIP-1α was separated from free biotin by Sephadex G-10 column (1×5 cm). The elution buffer was 0.1% gelatin in 5 mM acetic acid. The peak fraction of biotinylated mrMIP-1α was used for the next experiment. The T cells, which had been stimulated by antiCD3 mAb for 42 hrs were collected, washed with acid buffer and resuspended to $5\times10^5$ cells/0.2 ml in binding buffer. For competitive binding assays, the stimulated T cells were incubated with 5 ng of biotinylated mrMIP-1α and 50-fold excess of cold mrMIP-1α for 2 hrs 4° C. with continuous mixing. The cells were washed and resuspended in 0.1% BSA in PBS. The cells were mounted on slide glass by cytospinner (Cytospin 2, Shandon, UK). The cells were fixed in 2.5% gluteraldehyde (Sigma) in PBS for 10 min, washed with a buffer containing 50 mM Tris-HCl pH 7.5 and 0.15 M NaCl. The cells were stained with strept-ABC-AP complex (Dako) and AP red substrate (Zymed Kit, Calif.). Hematoxylin was used as counter staining of the nuclei. The cover slides were mounted with an aqueous mounting medium, glycerol-polyvinyl alcohol (Zymed).

[$^3$H] thymidine Incorporation

The resting splenic T cells ($2\times10^5$) were plated in a 96-well plate which had been coated with antiCD3 mAb. Ten ng of purified mrMIP-1α was added to each well. mrMIP-1α was added to the splenic T cells prior to, simultaneously or after the stimulation with antiCD3 mAb. The cells were cultured for 18 hrs, then labeled for 6 hrs with 1 μCi/well [$^3$H] thymidine. The cells were harvested by MB48R cell harvester (Biomedical Research and Development Laboratory, Gaithersburg, Md.). The level of [$^3$H] thymidine incorporation was determined in a scintillation counter in triplicate samples. In order to measure the blocking activity of anti-mrMIP-1α IgG, the mrMIP-1α was reacted with the antibodies for 60 min at 4° C. before addition to the T cells.

Measurement of IL-2 Production in AntiCD3 mAb-Stimulated T Cells

The murine splenic T cells were incubated for 30 mins with or without mrMIP-1α (50 ng/ml). The T cells ($1\times10^7$/ml) were then cultured in antiCD3 mAb-coated culture dishes (35 mm) with 1 ml of RPMI 1640 containing 10% FBS. The culture medium was collected at different time points. The IL-2 content was assayed on the CTLL-2 indicator cell line in 96 well plate. For IL-2 assays, the T cell culture supernatant was added on $5\times10^3$/well of starved CTLL-2 cells. The CTLL-2 cells were cultured for 48 hrs in which the last six hrs were pulsed with 1 μCi of [$^3$H] thymidine.

Results

Murine Resting Splenic T Cells Carry Receptors for MIP-1α

The proliferation of a T cell line, CTLL-R8 cells was inhibited by MIP-1α. Since the CTLL-R8 cells do not require IL-2 or antigen receptor stimulation for proliferation, it is difficult to investigate which signaling pathway the MIP-1α interferes. Murine resting splenic T cells were chosen and the activation of the T cells was achieved through TCR/CD3 complex. To study the effect of mrMIP-1α on T cells it was first examined whether the splenic T cells carry receptors for mrMIP-1α. As illustrated in FIG. 32, [$^{125}$I]mrMIP-1α bound to splenic T cells in a dose-dependent and a saturable manner. FIG. 32 shows the [$^{125}$I]mrMIP-1α binding curve and Scatchard plot analysis. Resting murine splenic T cells were incubated with various concentrations of [$^{125}$I]mrMIP-1α, in the presence or absence of 100-fold molar excess of unlabeled ligand. Insert: Scatchard plot analysis. The ordinate indicates the ratio of bound to free ligand concentration and abscissa, the femtomoles bound per $8\times10^5$ cells. The Kd obtained in this experiment was $0.4\times10^{-9}$ M. The binding was specifically inhibited by a 100-fold molar excess of unlabeled mrMIP-1α. A Scatchard analysis of the binding of [$^{125}$I]mrMIP-1α to the splenic T cells (FIG. 32 insert) indicated the existence of a class of high affinity receptor sites; a dissociation constant (Kd) of approximately $0.4 \times 10^{-9}$ M. The resting splenic T cells carried 680 receptors per cell.

MIP-1α Receptors Are Rapidly Internalized After Binding to the Ligands

It was hypothesized that MIP-1α will inhibit the proliferation of splenic T cells. First it was examined whether the number of receptors for MIP-1α changed when the T cells were stimulated with antiCD3 mAb because it was observed previously the number of MIP-1 α receptors doubled when the CTLL-R8 cells were stimulated with concanavalin A. Interestingly, when the T cells were stimulated with antiCD3 mAb, the [$^{125}$I]mrMIP-1α binding was reduced steadily.

FIG. 33 shows the specific binding of [$^{125}$I]mrMIP-1α to antiCD3 mAb-stimulated splenic T cells. The resting mouse splenic T cells were isolated through nylon wool and percoll gradient centrifugation. Aliquots of cells ($1.2 \times 10^7$/ml) were cultured in 35 mm culture dishes with the immobilized antiCD3 mAb for 0, 1/2, 2, 16, and 48 hrs. At each time point, the cells were harvested and the receptor binding assay was performed with [$^{125}$I]mrMIP-1α in the absence or presence of 100-fold excess cold mrMIP-1α. ■-specific binding of [$^{125}$I]mrMIP-1α (cpm).

At two hrs of stimulation only 10% of binding of unstimulated T cells were observed (FIG. 33). The binding was recovered 16 hrs after the stimulation (FIG. 33). Two potential explanations were put forward for such low bindings after T cells were stimulated with antiCD3 mAb; 1) the affinity of the receptor to the ligands was reduced; or 2) the receptors were internalized after binding to endogenous MIP-1α which were produced when the T cells were stimulated. First, the Kd value was examined before and 30 min after the antiCD3 mAb stimulation to evaluate the changes in receptor-ligand affinity. The Kd value of both cases were almost identical (data not shown), ruling out the possibility of changing receptor affinity. Second, the kinetics of receptor internalization were compared between unstimulated and stimulated T cells. As shown in FIG. 34, the T cells internalized their MIP-1α receptors within 30 min after the ligand binding.

FIG. 34 shows the internalization of MIP-1α receptor in murine splenic T cells. The resting T cells were allowed to bind to [$^{125}$I]mrMIP-1α at 4° C. for 2 hr. Cells were washed 3 times and divided into 12 aliquots ($5 \times 10^6$/ml) and cultured in antiCD3 mAb-coated dishes or on medium-coated dishes. After the indicated times, aliquots of cells and supernatants were withdrawn. The mrMIP-1α bound to the receptors was removed by acid treatment. Subsequently, the radioactivity in the cell pellet was determined. This represented internalized [$^{125}$I]mrMIP-1α. ●, cells stimulated with antiCD3 mAb; ●, cells without stimulation. Levels of free [125I] were determined in the TCA-soluble fraction of supernatant. ■, supernatant from antiCD3 mAb-stimulated cells; □, supernatant from non-stimulated cells.

The kinetics of MIP-1α receptor internalization of unstimulated T cells was similar to that of stimulated T cells. Therefore, it was suspected that the rapid internalization of the receptor might be the reason that the binding of [$^{125}$I] mrMIP-1α was reduced. This data also strongly supports the idea that MIP-1α is produced when the T cells are stimulated with antiCD3 mAb and the receptors have been internalized after binding its own ligands.

Therefore, it was examined whether the T cells produce MIP-1α after stimulated by antiCD3 mAb. As shown in FIG. 35, T cells produce MIP-1α mRNA as early as 30 min after the stimulation. FIG. 35 shows a northern analysis of mrMIP-1α mRNA. Cytoplasmic RNA was purified from T cells 0, 1/2, 3, 6, and 16 hrs of antiCD3 mAb stimulation. 20 μg of total RNA were loaded in each lane. L2G25B is a murine MIP-1α cDNA. Ethidium bromide-stained 28S ribosomal RNA is shown (bottom) to indicate that a similar amount of RNA was loaded in each lane. MIP-1α was detected as early as 6 hrs after the stimulation and was accumulated at least until 48 hrs after the stimulation (FIG. 36). FIG. 36 shows a western blot analysis of mMIP-1α protein secreting in supernatant after antiCD3 mAb-stimulation. The left 5 lanes (1–5) represent standard concentration of mrMIP-1α, 1 ng, 2.5 ng, 5 ng, 10 ng, and 50 ng, respectively. Lanes 6, 7, 8, and 9 represent the mrMIP-1α from the medium cultured for 2, 6, 16 and 48 hrs, respectively. The production of MIP-1α was estimated as 0.3 ng/10$^6$/day. We concluded that an autocrine loop may exist in which the induction of MIP-1α and its secretion into the supernatant would result in the binding of MIP-1α and its secretion into the supernatant would result in the binding of MIP-1α to its receptor and hence internalization of the complex. At 16 hrs of the stimulation, [$^{125}$I]mrMIP-1α binding was recovered although MIP-1α was abundantly present in the medium. It is possible that receptor affinity is decreased by 16 hrs of stimulation or the MIP-l1 in the medium is a form that is incapable of binding.

The Majority of T Cells Carry MIP-1α Receptors

Whether all the T cells or restricted subsets of T cells carried MIP-1α receptors was examined. The mrMIP-1α was biotinylated and the binding was detected with alkaline phosphatase-conjugated streptavidin. As shown in FIG. 37 approximately ninety percentage of cells in the microscopic field showed binding to MIP-1α. The primary T cells were stimulated by antiCD3 mAb for 48 hrs. Five ng of biotinylated mrMIP-1α were applied to the T cells. After incubation for 2 hrs the cells were washed with PBS and cytospun onto the microscopic slides. The strept-ABC-AP and red fast substrate were used to stain the biotinylated mrMIP-1α on the cell membrane. A shows the red fine granules on the cell membrane. B 50-fold excess cold mrMIP-1α abolished the staining. Among the stained cells 70% was L3T4$^+$ and 30% were Lyt 2.2$^+$. The data indicated that T cells uniformly expressed MIP-1α receptors, indicating that MIP-1α may be a broad regulator of T cell finction.

mrMIP-1α Inhibits AntiCD3 mAb-Mediated T Cell Proliferation

Since the mouse splenic T cells carried receptors for MIP-1α, and previously, the rMIP-1α inhibited the growth of CTLL-R8 cells, a T cell line, it was expected that MIP-1α inhibited the antiCD3 mAb-mediated T cell proliferation. Initially, when mrMIP-1α was added after the T cells were stimulated, the T cell proliferation was not noticeably affected. Therefore, the mrMIP-1α was added before the T cell stimulation. FIG. 38 shows the inhibition of murine splenic T cell proliferation by mrMIP-1α. Enriched splenic T cells ($2 \times 10^5$/well) were plated in a 96-well plate in 0.2 ml of RPMI 1640 containing 10% FBS. mrMIP-1α (50 ng/ml) was added before and after the stimulation of T cells with antiCD3 mAb. The T cells were incubated for 30 hrs and pulsed for 6 hrs with 1 μCi [3H] thymidine per well. Each column indicates means [$^3$H] thymidine incorporation of triplicate cultures and the SEM is on the top of each column. ■, antiCD3 mAb-stimulated T cells in the presence of mrMIP-1α □, antiCD3 mAb-stimulated T cells in the absence of mrMIP-1α. B. Blocking of mrMIP-1α effect by anti-mrMIP-1α IgG. Experimental conditions were the same as those in A except that the cells were cultured for 18 hrs. mrMIP-1α and anti-mrMIP-1α IgG were mixed at the concentration indicated before addition to the murine splenic T cells. The control wells did not receive mrMIP-1α or anti-mrMIP-1α IgG. Each column indicates mean [$^3$H] thymidine incorporation of triplicates and SEM is on the top of each column.

Figure 38A:
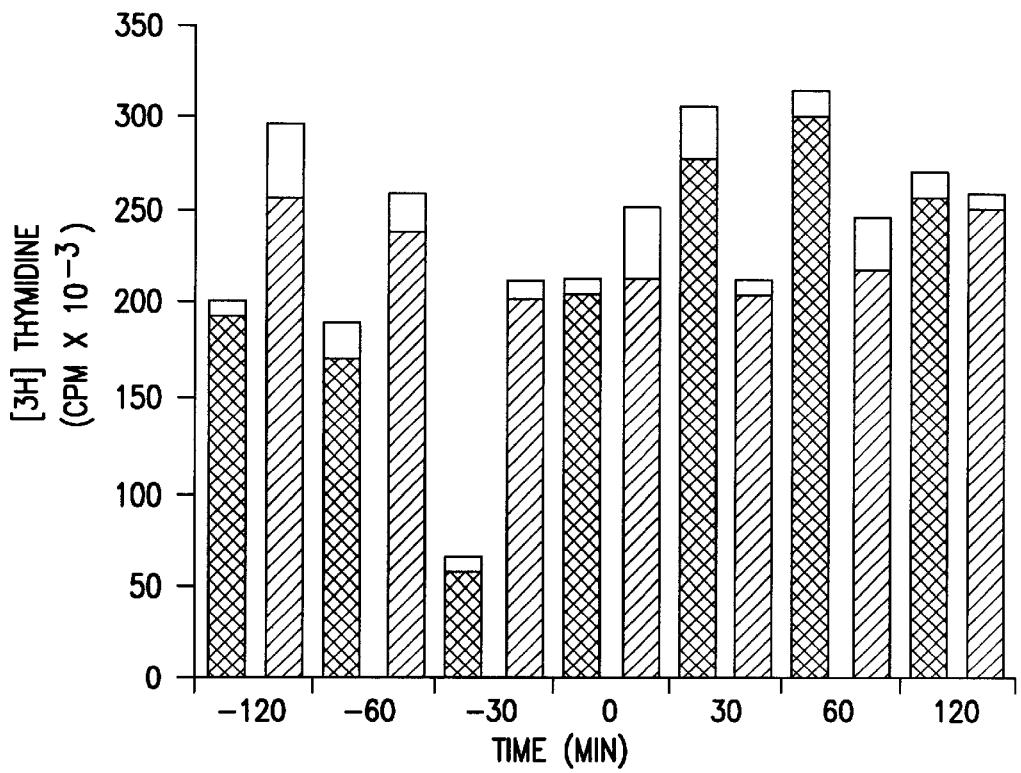
Figure 38B:
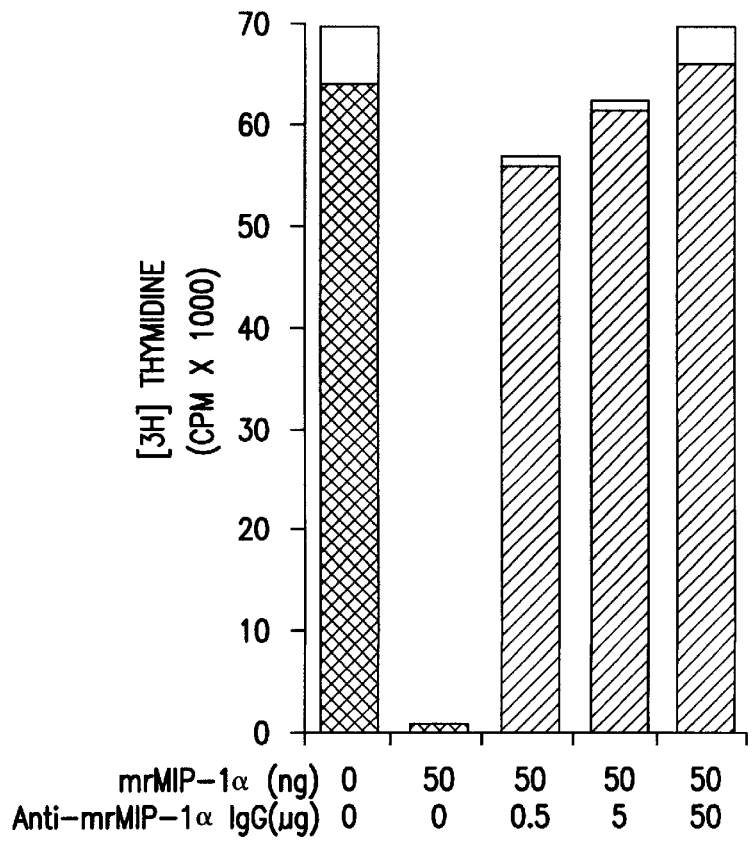

As shown in FIG. 38A, the T cell proliferation was inhibited dramatically when the mrMIP-1α was added 30 min prior to the T cell stimulation with antiCD3 mAb. A slight inhibition of the T cell proliferation was also observed when the mrMIP-1α was added 1 hr and 2 hrs prior to the stimulation. To document the specificity of the mrMIP-1α activity, the mrMIP-1α was treated with rabbit polyclonal anti mrMIP-1α IgG prior to the addition to the T cells. As shown in FIG. 38B, the antibodies blocked the growth inhibitory activity of mrMIP-1α in an antibody concentration-dependent fashion. These data indicate that mrMIP-1α produced a negative effect on T cell growth. The inhibitory activities appeared to be only when the MIP-1α met T cells before the T cells were committed to proliferate.

mrMIP-1α Inhibits the Production of IL-2

The next set of experiments asked whether the T cell suppressive effect of mrMIP-1α was associated with the level of IL-2 secretion. To this end, the amount of IL-2 was measured in the culture medium of the T cells which were stimulated with antiCD3 mAb with or without mrMIP-1α. As shown in FIG. 39 the amount of IL-2 measured by CTLL-2 responses was reduced up to 80% (for example, 16 hrs post incubation) when the T cells were treated with mrMIP-1α. FIG. 39 shows the effect of mrMIP-1α on antiCD3 mAb-mediated IL-2 secretion for 30 min prior to stimulation. The T cells (1×10$^7$) were cultured in anti-CD3 mAb-coated culture dishes (35 mm) with 1 ml of RPMI-1640 with 10% FBS. The culture medium was collected at 2, 6, 16 and 26 hrs for post-incubation. The murine splenic T cells either were incubated with or without mrMIP-1α (50 ng/ml) for 30 min prior to stimulation. The culture supernatant (5 μl) were assayed for IL-2 content on CTLL-2 indicator cell line (5×10$^3$/0.1 ml). All the assays were performed in triplicate. This data indicate that the negative effect of MIP1α on T cells may be mediated at least in part by suppressing IL-2 production required for autocrine T cell growth.

FIG. 40 shows the effect of mrMIP-1α pretreatment on anti-CD3 mAb-mediated IL-2 mRNA accumulation. 13 μg of total RNA from splenic T cells stimulated anti-CD3 mAb (left panel) for 2 hr (lane 1), 6 hr (lane 2) and 16 hr (lane 3) and pretreated with mrMIP-1α for 30 min (right panel) prior to stimulation with anti-CD3 mAb for 2 hr (lane 1), 6 hr (lane 2) and 16 hr (lane 3) was fractionated, transferred to GeneScreen Plus membrane, and probed with $^{32}$P-labeled murine IL-2 probe. γ-actin probe was used to show that each lane contains an almost equal amount of RNA (bottom lanes). Hybridization signals are indicated for IL-2 mRNA.

As shown in FIG. 40, the level of IL-2 mRNA reflected the differences in the amount of IL-2 in the T cell culture medium. The IL-2 mRNA content in the MIP-1α treated T cells was approximately 5-fold lower than that in the MIP-1α-untreated T cells after 6 hrs of anti-CD3 mAb stimulation. The differences in the IL-2 mRNA level were not noticeable at 2 hr and 16 hr of anti-CD3 mAb stimulation.

Discussion

We have demonstrated that mrMIP-1α inhibits the proliferation of resting murine splenic T cells induced by an anti-CD3 mAb. The negative regulation by MIP-1α occurred during the initial stage of T cell activation, for if T cells are pretreated with MIP-1α 30 min prior to anti-CD3 stimulation in the presence of accessory cells, these T cells do not proliferate. The effect of MIP-1α appears to be transient, for if T cells are treated 2 hr prior to stimulation, these cells are able to proliferate. After anti-CD3 stimulation, MIP-1α receptors are downregulated on these cells and MIP-1α is secreted. MIP-1α may affect T cell proliferation at multiple points during activation, for MIP-1α binding sites reappear at 16 hr post stimulation.

Since anti-CD3 stimulation of T cells induces the production of MIP-1α, MIP-1α may directly or indirectly affect the response of other lymphoid cells in the vicinity. Sherry and colleagues have shown that MIP-1 stimulated the secretion of TNF, IL-1α and IL-6 in murine macrophages. The effect of MIP-1α on B cells and whether B cells secrete MIP-1α is not known at this time. B cells can respond to immunosuppressive factors, for T cell-dependent and independent B cell activation were blocked by TGF-β (87). The finction of MIP-1α in the local vicinity of an immune response may be to block bystander lymphocyte activation. It has been shown that activated T cells can polyclonally activate B cells in an antigen non-specific manner. MIP-1α could hinder polyclonal activation during that point in time where activated T cells acquire the property of being capable of polyclonally activating resting B lymphocytes. Yet, because of the transient effect of MIP-1α, the temporarily suppressed resting lymphocyte could soon after still respond to their specific antigen if it entered the host. The growth inhibitory effect appears to be in part associated with the suppression of IL-2 production because mrMIP-1α reduced the production of IL-2 and IL-2 mRNA up to 80%. However, it has not been determined whether the IL-2 expression is inhibited at the transcriptional or post-transcriptional stages. Genes or biochemical parameters involved in the negative regulation by MIP should be determined to understand the mechanism involved in negative regulation of T cells and its significance in immune responses.

FIG. 33 shows that the receptors for MIP- I a were not internalized at 16 hr post-stimulation even though a large quantity of MIP-1α was present in the medium. We do not have an explanation for this at the present time. One possibility is that the MIP-1α accumulated at 16 hrs is inactive. We and others have observed that MIP-1α monomers are susceptible to aggregation. In addition, we have shown that only the monomeric form and not the aggregated form of MIP-1α is biologically active. The aggregation was concentration-dependent. Therefore, perhaps when the concentration of MIP-1α reaches a certain level, it aggregates to a degree of total inactivity. If this is the case, the aggregation property might be a control mechanism of MIP-1α function. Recently, Taga et al. (88) reported T cell inhibitory effect of IL-10. IL-10 also suppressed the production of IL-2. IL-10 appears to selectively impair the ability of macrophages to provide costimulatory signals. It is of great interest whether mrMIP-1α interferes with the biochemical pathways generated by TCR occupancy or by co-stimulation. TGF-β is another T cell inhibitory cytokine that appears to inhibit IL-2 production and formation of high affinity IL-2 receptor. TGF-β has been demonstrated to suppress the generation of LAK activity and to suppress the lytic potential by abrogating perforin expression which is believed to be a major lytic molecule. It has been reported that TGF-β has been demonstrated to suppress the generation of LAK activity and to suppress the lytic potential by abrogating perforin expression which is believed to be a major lytic molecule. It has been reported that TGF-β prevents phosphorylation of the retinoblastoma gene product, which results in arresting cells in the late G$_1$ phase of the cell cycle.

Whether IL-10, TGF-1β and MIP-1α interfere with the signaling of T cell growth in a similar or different way remains to be determined.

An Inducible Receptor-Like Molecule, 4-1BB1, is Expressed in Infiltrating Mononuclear Cells of Diabetic NOD Mice A series of T-cell subset-specific cDNAs were isolated from cloned murine T-cells by employing a modified differential screening procedure (89). The nucleotide sequence and expression properties of some of the cDNA species have been reported (90). One of the genes not previously characterized, 4-1BB, was studied further. The transcript of 4-1BB was inducible by concanavalin A in mouse splenocytes, T-cell clones, and hybridomas. The expression of 4-1BB transcripts was inhibited by cyclosporin A. The 4-1BB mRNA was inducible by antigen receptor stimulation but was not inducible by IL-2 stimulation in the cloned T-cells (91). The 4-1BB cDNA encodes a peptide of 256 amino acids containing a putative leader sequence, a potential membrane anchor segment, and other features of known receptor proteins. Therefore, the expression pattern of 4-1BB resembles those of lymphokine mRNAs while the sequence appears consistent with those of receptor proteins.

The deduced amino acid sequence of 4-1BB is similar to tumor necrosis factor receptor (92). The 4-1BB protein is also a member of the nerve growth factor receptor super family, for the deduced amino acid sequence of 4-1BB predicts a cysteine-rich extracellular domain (93). Shaw et al. (94) mapped the amino acid sequence involved in the $p56^{lck}$ binding in the cytoplasmic domains of $T_4$ and $T_8$ antigens. The 4-1BB protein contains the consensus amino acid sequence which can bind to the $p56^{lck}$ in the putative cytoplasmic domain.

We are interested in determining the biological finction of this molecule. In this context, an antiserum was prepared which recognizes the 4-1BB protein and determined the protein expression in various tissues of normal and pathologic mice.

As a diseased tissue, the pancreas of the diabetic NOD mouse was chosen for study. The NOD mouse has become an important model of Type I, or insulin-dependent diabetes mellitus (95). In both humans and NOD mice, an autoimmune pathogenesis is suggested by the presence of lymphocytic infiltrations in the pancreatic islets that appear to result in selective β-cell destruction (96). The infiltrating T-lymphocytes appear to be activated by triggering agents, possibly auto-antigens, upon infiltration into the pancreas. As a first step to understanding the biological functions of this molecule, the possibility that 4-1 BB is expressed in the infiltrating mononuclear cells in the pancreatic islets of NOD mice was explored.

Materials and Methods

Cells

CTLL-R8, a mouse cytolytic T-cell line (97), was grown in DMEM (Gibco Laboratories, Grand Islands, N.Y.) containing 100 units/ml of penicillin, 100 μg of streptomycin, 4 units/ml of rIL-2 (Boehringer-Mannheim, Indianapolis, Ind.) and 10% FBS. RAW 264.7, a murine macrophage cell line (38), and EL-4, a mouse thymoma cell line were cultured in DMEM, containing 10% FBS, 25 mM Hepes, 1 mM sodium pyruvate, 100 units/ml of penicillin and 1 00 μg/ml of streptomycin. COS-1 cells were grown in DMEM containing 10% FBS, 100 units/ml of penicillin, and 100 μg/ml of streptomycin.

Antibody Preparation

Five oligopeptides representing different regions of the deduced 4-1BB protein (4-1BBP) sequence were synthesized (Applied Biosystems, Foster City, Calif.). Two sequences, named 4-1BB-0 and 4-1BB-11, stimulated the production of antibodies. The amino acid sequence of the oligopeptide 4-1BB-0 was a 12-mer from amino acids 105–115 of the deduced 4-1BBP. Oligopeptide 4-1BB-11 was a 25-mer from amino acids 133–157 of the deduced 4-1BBP. A tyrosine residue at the C-terminus of the oligopeptide 4-1BB-0 was added for labeling with [$^{125}$I] if needed. The peptides were conjugated to keyhole limpet hemocyanin (KLH) using a heterobifunctional cross linker, m-maleimidobenzoyl-N-hydroxysuccinimide ester (98).

Rabbits were immunized with peptide-KLH (100 μg per dose) emulsified in Freund's complete adjuvant. The rabbits received one intracutaneous injection in 4 foot pads and one intramuscular injection two weeks apart. After two weeks, the rabbits received three consecutive intravenous injections (50 μg per dose) without adjuvant. The serun was obtained 5 days after the final injection, and the titer was measured by ELISA using the peptide as the antigen.

Flow Cytometry $1 \times 10^7$ CTLL-R8 cells were incubated with preimmune or IgG fraction of anti-4-1BB-rabbit serum on ice for 30 min. Cells were washed three times in RPMI 1640 containing 5% FBS. Then the cells were incubated on ice for 30 min with fluorescein isothiocyanate (FITC)-conjugated goat anti-rabbit immunoglobulin. The cells were washed again with phosphate buffered saline (pH 7.4) containing 10% bovine serum albumin. Flow cytometry was performed using an EPICS 753 (Coulter) fluorescence-activated cell sorter.

Immunocyiochemistry and Histology

The cells were cultured on sterile cover slides coated with poly-L lysine. For some experiments, CTLL-R8 cells were stimulated with concanavalin A (5 μg/ml) for various lengths of time. The cells on coverslips were washed three times with phosphate-buffered saline (PBS), pH 7.4, for 5 min and fixed by treating with 3.7% formaldehyde in PBS at room temperature for 10 min and with methanol at −20° C. for 4 min. Subsequently, the cells were treated with acetone at −20° C. for 1 min.

To prepare nonpathologic tissue slides, C57B1/6 mice were perfused with 4% paraformaldehyde in PBS through the heart. After perfusion, organs were excised and cut in blocks of 1–2 mm thickness. The organs included the brain, heart, lung, thymus, liver, spleen, pancreas, and kidney. These tissue blocks continued to be fixed in 4% paraformaldehyde for 24 hrs. The tissue blocks were further cut with a vibratome into slices of 40 gm thickness. Lung specimens were cut with a cryostat after being frozen in Tissue-Tek O.C.T. (Miles Scientific, Naperville, Ill.).

Streptavidin-biotinylated alkaline phosphatase complex (ABC-Ap) (DAKO Corporation, Denmark) was used to stain cells or frozen sections of lung. A positive reaction was indicated by red staining with a fast red. Horseradish peroxidase-antiperoxidase (PAP) was used to stain the vibratome sections of other organs. The anti-4-1BB-0 rabbit serum was used as primary antibodies and pre-immune rabbit sera were used as controls. Meyer's hematoxylin or methyl green was used for counter staining.

To study the immuno-cytochemistry of the NOD mouse pancreas, the pancreas was fixed in Camoy's B solution (75% ethanol and 25% glacial acetic acid) and was processed to make a paraffin block. The paraffin sections were deparaffinized, rehydrated in graduated alcohols and immersed in PBS, while frozen sections were used after fixation in cold acetone. Appropriately diluted antibodies were incubated with the sections for 3 hrs at room temperature, followed by washing in PBS for 5 min and incubation with FITC-labeled protein A (1:40 diluted in PBS) with 0.05% Evan's blue) for another 3 hrs at room temperature. Pictures were taken with an Olympus BH-2 fluorescent microscope. Parallel with immunofluorescence staining, the sections were stained with hematoxylin and eosin, allowing the grading of insulitis to be scored as described elsewhere (99).

NOD Mouse

The colony of NOD mice was obtained from the Second Department of Internal Medicine, Kobe University School of Medicine, Kobe, Japan. These animals were maintained on regular mouse chow and tap water ad libitum at the University of Calgary. At the age of 10 weeks. the 5 NOD mice were treated with cyclophosphamide (Homer, Montreal, Quebec, Canada) at the dose of 150 mg/Kg body weight twice at 3-day intervals. At the age of 26 weeks, they were sacrificed and pancreata were excised.

Immunoblot Analysis

Cells grown in petri dishes were washed in PBS and lysed by adding TNE buffer (50 mM Tris HCl, pH 8.0, 1% NP-40, 2 mM EDTA) on ice for 2 hrs. The TNE buffer contained the protease inhibitors aprotinin and leupeptin at 100 µg/ml each. The cell lysate was harvested and centrifuged for 5 min. The supernatant containing approximately 1 mg/ml of protein was denatured by boiling for 2 min in a sample buffer consisting of 62.5 mM Tris HCl, pH 6.8, 10% glycerol, 1% SDS, 1% P-mercaptoethanol and 0.001% bromphenol blue. The proteins were resolved on 12% SDS-PAGE (polyacrylamide gel electrophoresis) and transferred electrophoretically onto an Immobilon membrane (Millipore, Bedford, Mass.). The membranes were blocked to prevent nonspecific antibody binding by incubating in 5% nonfat dry milk in TBST (50 mM Tris HCl, pH 7.4, 0.15 M NaCl and 0.05% Tween-20) for 1 hr at room temperature. The membranes were then treated with primary antibodies or primary antibodies treated with oligopeptides at room temperature for 1 hr. After four washes with TBST, the membranes were incubated with a secondary antibody against rabbit IgG(H+L)-alkaline phosphatase conjugate (Zymed, Inc., S. San Francisco, Calif.) at 1:100 dilution as recommended by the manufacturer. The rabbit antiserum absorbed by an oligopeptide was prepared as follows. The rabbit antiserum was incubated with various concentrations of the oligopeptide (0, 0.1, 1.0, and 10 µg/ml) in TBST buffer and 1% dry nonfat milk, then microcentrifuged at 14,000 rpm for 20 min, and the supernatant was used as a primary antibody after further dilution in TBST.

The reactive bands were visualized by incubating the membrane with chromogenic substrates, p-nitrobluetetrazolinum chloride (NBT) and 5-bromo-4-chromo-3-indolyl-phosphate (BCIP) (Bio Rad, Richmond, Calif.) in 0.1 M Tris, pH 9.5, 0.1 M NaCl, and 5 mM $MgCl_2$.

Construction of the Expression Plasmid of Truncated 4-1BB

The putative extracellular domain of 4-1BB cDNA was amplified by polymerase chain reaction (PCR) (100). An XhoI site was created at the 5' end of the forward primer and a stop codon, (TAA), and an Eco RI site were created in the reverse primer. The PCR product was digested with XhoI and EcoRI and the ~0.6 kb fragment was purified. The XhoI-Eco RI fragment (P4-1BBs) was inserted into the PXM vector (101).

Production of the Recombinant Truncated 4-1BB Protein

COS-1 cells were grown to 30–50% confluency and were transfected with the truncated 4-1BB in the PXM vector using the DEAE dextran method (102). Forty-four hours post transfection, the culture medium was replaced with serum-free medium (Opti MEM, Gibco Laboratories, Grand Island, N.Y.). The culture medium was harvested twice every 24 hrs. The proteins in the conditioned medium were precipitated with 4 volumes of acetone at −20° C. and resuspended in a mixture consisting of a chromatography buffer (50 mM Tris, pH 7.4, 0.15 M NaCl and 0.05% Tween −80), 5 M urea and 1% β-mercaptoethanol. After the removal of undissolved particles by brief microcentrifugation, the supernatant was subjected to Sephadex G-200 chromatography. The fractions that were reactive with rabbit anti-4-1BB-0 antiserum in Western blot analysis, were pooled. The truncated, thus soluble 4-1BB protein (4-1BBPs) was further enriched through fractionation with Q-Sepharose column (Pharmacia Fine Chemicals) with a linear gradient of NaCl from 0.0 to 1.0 M. The amino-terminal sequence of 4-1BBPs was determined by an automatic peptide sequencer PI 2090 (Proton Instrument, Tarzana, Calif.) after the protein was transferred to Immobilon-p (Millipore, Bedford, Mass.).

Northern Blot Analysis

Mouse organs were sliced into 1 mm thick pieces. A portion of each organ was stimulated by incubating in DMEM containing PMA (phorbol 12-myristate 13-acetate, 20 ng/ml) for 24 hrs. A portion of the spleen was treated with concanavalin A (10 µg/ml) in DMEM. The remaining portion of each organ was incubated in DMEM plus 10% FBS without PMA or concanavalin A for 24 hrs. The tissues were frozen in −70° C. and pulverized in liquid nitrogen before extracting RNA. RNA was extracted from the tissues and cells by the guanidinium-phenol extraction procedure (103). The RNA was fractionated on a 1.4% formaldehyde denaturing agarose gel, transferred to a GeneScreen Plus membrane, and hybridized to $^{32}P$-labeled probes.

Results

Specificity of Antioligopeptide Antisera to 4-1BB and Fxpression of 4-1BB Protein The only information previously available on the 4-1BB was the nucleotide sequence of the cDNA and the predicted amino acid sequence. In order to study the 4-1BB protein (4-1BBP), polyclonal antibodies were raised against oligopeptides representing five different portions of the predicted 4-1BBP. To aid in proving that the putative antisera contain antibodies which uniquely recognize the 4-1BBP, a search for cell lines that express 4-1BB mRNA was made. CTLL-R8 cells produced a high level of 4-1BB mRNA while a macrophage cell line, Raw 264.7 or unstimulated EL-4 cells did not produce detectable amounts of 4-1BB mRNA (FIG. 41). FIG. 41 shows the expression of 4-1BB on RNA in CTLL-R8. Cytoplasmic RNA was prepared from mouse CTL line, CTLL-R8 (lane A), macrophage cell line, RAW 264.7 cells (lane B) and unstimulated EL-4 cells (lane C). Ten micrograms of total RNA was fractionated on a formaldehyde/agarose gel, transferred to a GeneScreen Plus, and hybridized to 4-1BB cDNA probe. Arrows indicate the specific signals. Positions of 28S and 18S rRNA markers are indicated.

We then tested whether any of the antibodies recognized the three cell lines differentially. Two antisera among five tested had a positive reaction to CTLL-R8 cells while the antibodies did not stain RAW 264.7 or EL-4 cells. One anti-oligopeptide antiserum, anti-4-1BB-0, stained CTLL-R8 cells at a higher dilution (1:1600) than did the other one, anti-4-1BB-11. The staining pattern of CTLL-R8 cells revealed a diffuse granular distribution in the cytoplasm and uniform staining on the cell membrane (data not shown). When the lysates of CTLL-R8, RAW 264.7 and EL-4 cells, were prepared and an immunoblot analysis performed with the anti-4-1BB-0 serum, a unique band of 40 kD was recognized in the CTLL-R8 cells but not in the RAW 264.7 or EL-4 cells (FIG. 42).

FIG. 42 shows an immunoblot analysis of CTLL-R8 cell lysates with anti-4-1-BB-0 serum. Lanes A and B contain approximately 20 μg of CTLL-R8 cell lysate. Lanes C and D contain approximately 20 μg protein of RAW 264.7 and EL-4 cell lysate, respectively. Lane A reacted with preimmune rabbit serum. Lanes B, C and D reacted with anti-4-1BB-0 serum (1:1600). The arrow indicates the 40 kD protein band on Lane B.

To prove further the specificity of the antioligopeptide antisera, an expression plasmid was prepared containing a truncated 4-1BB cDNA. The membrane anchor and cytoplasmic domains were eliminated from the 4-1BB cDNA. The truncated cDNA was inserted into the PXM vector and expressed in COS-1 cells. The culture medium of the transfected COS-1 cells was concentrated and fractionated by Sephadex G-200 chromatography. An aliquot of each fraction was run on SDS-PAGE, transferred to the Immobilon membrane (Millipore, Bedford, Mass.), and treated with the anti-oligopeptide antiserum, anti-4-IBB-0. A peak of protein was found which reacted with the anti-4-1BB-0. There was no detectable amount of the 4-1BBP in the COS-1 cell lysate. The soluble 4-1BBP (4-1BBPs) fraction was further purified through Q-sepharose column. The molecular size of the 4-1BBPs was approximately 23 kD on a 10% SDS-PAGE.

Next, a series of immunoblots was prepared containing the 4-1BBPs. The blots were stained with unabsorbed or absorbed anti-4-1BB-0 antiserum. FIG. 43 shows an immunoblot analysis of the 4-1BBPs. Lanes A, B, C and D contain the cell culture supernatant of COS-1 cells which were transfected with truncated 4-1BB expression plasmids. Lane A reacted with unabsorbed anti-4-1BB-0 serum. Lanes B to D reacted with anti-4-1BB-0 serum absorbed by 0.1 gg/ml (lane B), 1 μg/ml (lane C) and 10 μg/ml (lane D) of the 4-1BB-0 peptide. The arrow with the 23 kD indicates the bands seen on lanes A and B. FIG. 43, lane A, shows the 4-1BBPs band (23 kD) from the COS-1 cell medium reacted with anti-4-1BB-0. The 4-1BBPs band gradually disappeared when the anti-4-1BB-0 was absorbed by the increasing amount of the oligopeptide 4-1BB-0. As shown in FIG. 43, lane B, the antibodies to the 4-1BB protein were not absorbed completely by 0.1 μg/ml of the 4-1BB-0 peptide. However, when the concentration of 4-1BB-0 was increased to 1.0 μg/ml (lane C) and 10 μg/ml (land D), the anti-4-1BB-0 antibodies were completely absorbed, showing no 4-1BBPs bands.

We finally determined the amino-terminal sequence of the purified 4-1BBPs. The sequence was Val-Gln-Asn-Ser-X-Asp. The amino acid sequence at positions 1, 2, 3, 4 and 6 was identical to that of the mature 4-1BBP predicted from the cDNA sequence. Amino acid at position 5 which is supposed to be Cys was not determined. These results indicate that the deduced amino acid sequence and assignment of signal sequence are correct. When the potential transmembrane domain was removed from the complete 4-1BB molecule, the protein was secreted. These results suggest that 4-1BBP is likely to be associated with the cellular membrane as predicted by the primary structure.

The 4-1BBP expression was analyzed by flow cytometry and cell sorting using an EPICS 753 fluorescence-activated cell sorter (Coulter). FIG. 44 shows representative histograms of IgG fraction of anti-4-1BB-O related fluorescence intensity of CTLL-R8 cells. X-axis represents fluorescence intensity and Y-axis, cell numbers. A: Unsorted CTLL-R8 cells stained with IgG fraction of anti-4-1BB-O. B and C: The stained population in A was separated from the rest of the cells, cultured for 8 days, and stained with either preimmune (B) or IgG fraction of anti-4-1BB-O (C). Flow cytometry and cell sorting were performed with an EPICS 753 fluorescence-activated cell sorter (Coulter).

Figure 44A:
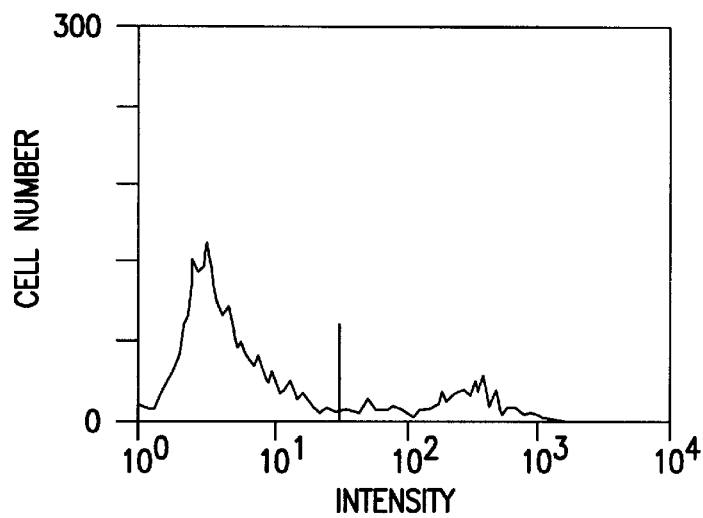
Figure 44B:
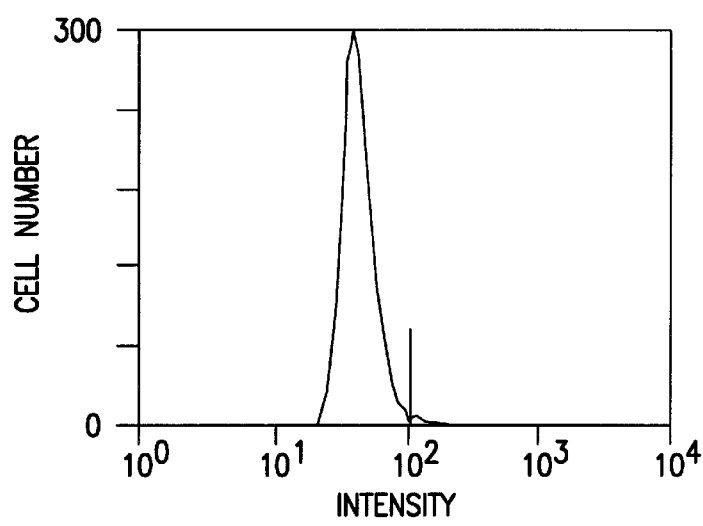
Figure 44C:
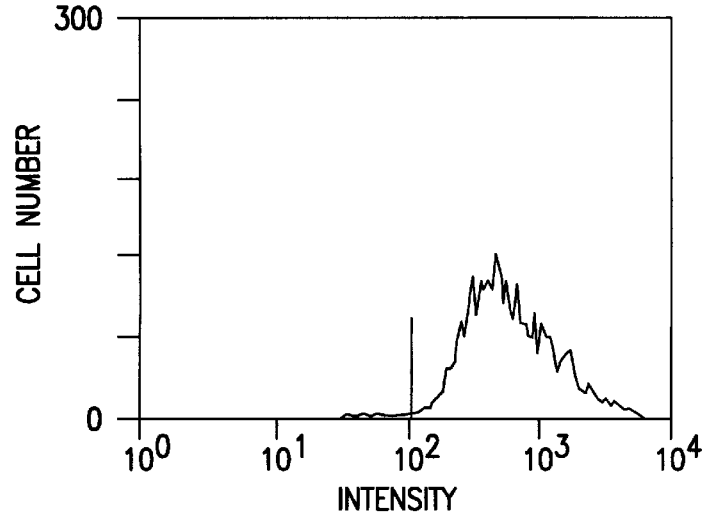

When the CTLL-R8 cells were stained with IgG fraction of the anti-4-1BB-O rabbit serum, approximately 21% of the cells were labeled (FIG. 44A). Next, a sort for the 4-1BB+ cells was performed and these cells were cultured in the presence of 20 units/ml of rIL-2. These cells were cultured for 8 days before testing 4-1BBP expression by flow cytometry again. When these cells were stained with anti-4-1BB-O serum, 98.3% of this cell population was labeled (FIG. 44C), while preimmune serum stained the cells at background level (FIG. 44B). These results indicated that the 4-1BB protein was expressed on the cell surface and perhaps represented a receptor.

The Tissue Distribution of 4-1BB. RNA was extracted from tissues of various organs and tested for the expression of 4-1BB mRNA. 4-1BB mRNA was detected in the spleen, kidney, and heart; but no RNA was detectable in the liver, adrenal gland, or pancreas. The RNA level was markedly elevated when the spleen and heart were treated with PMA, but other organs did not show 4-1BB RNA induction after PMA treatment (FIG. 45).

FIG. 45 shows the expression of 4-1BB RNA in mouse tissues. The total RNA from the spleen (lanes A, B, and C), heart (lanes D and E), and kidney (lanes F and G), was fractionated on formaldehyde-denaturing agarose gel, transferred to GeneScreen Plus, and hybridized to a $^{32}$P-labeled 4-1BB cDNA probe. Each lane contains 20 μg of RNA. Lane A: unstimulated spleen RNA, lane B: concanavalin A-stimulated spleen RNA, lane C: PMA-stimulated spleen RNA, lane D: unstimulated heart RNA, lane E: PMA-stimulated heart RNA, lane F: unstimulated kidney RNA, and lane G: PMA-stimulated kidney RNA. Positions of 28S and 18S rRNA markers are indicated. An arrow indicates the specific hybridization signal.

The 4-1BBP was detected in the medullary tubules and medullary rays of the kidney (data not shown). A small number of mononuclear cells in the alveolar septae of the lungs and some lymphocytes in the spleen showed weak staining. The pancreas, liver, testes, and ovary expressed neither 4-1BB mRNA nor 4-1BBP. The detailed description of tissue distribution of the 4-1BBP will be published elsewhere.

4-1BB Expression in Infiltrating Mononuclear Cells

In serial sections of the pancreata, 40 islets were observed after hematoxylin-eosin staining. FIG. 46 shows the histology of NOD mouse pancreata and immunofluorescent staining of islets showing different stages of insulitis. Pancreas sections of A, C, and E were stained with the standard hematoxylin and eosin staining technique, while those of B, D, and F were stained with anti-4-1BB-0 serum and FITC-conjugated protein A. B, D, and F are the corresponding islets to A, C, and E, respectively. A and B: early-stage insulitis, C and D: intermediate-stage insulitis, and E and F: late-stage insulitis. Note the strong immunofluorescent staining in the mononuclear cells at the periphery of islets showing the early stage of insulitis, while the staining is not apparent in the islets showing the late stage of insulitis.

Among those islets, 10 showed no insulitis and 12 showed signs of early insulitis in which lymphocytes had infiltrated only to the periphery of each islet (FIG. 46A). The remaining 18 islets showed intermediate or late stage insulitis in which the lymphocytes had infiltrated into the islets and showed signs of islet destruction (FIGS. 46C and 6E). The serial sections were then stained with anti-4-1BB-0. None of the 10 intact islets showed 4-1BB expression (Table 5). However, mononuclear cells accumulated at the periphery of the islets were stained with the anti-4-1BB-0 serum in the early stage of insulitis (FIG. 46B). All 12 of the early insulitis islets demonstrated the same staining pattern (Table 5). 4-1BB expression diminished gradually in the mononuclear cells during the intermediate to late stages of insulitis (FIGS. 46D and 6F). Seven of the 18 islets of intermediate to late stage insulitis showed weak staining in the infiltrating mononuclear cells, and the remaining 11 islets showed no staining. These results indicate that the 4-1BB protein is most likely associated with T-cell functions during the early phase of activation. Such an early expression of 4-1BB protein is well corroborated with the finding that 4-1BB mRNA was detectable as early as 30 min after the T-cells are stimulated with lectins or antibodies to T-cell receptors.

TABLE 5

Expression of the 4-1BB protein in the insulitis lesion of NOD mice according to the grade of insulitis.

| Stage of Insulitis | No. | 4-1BB Expression | | |
|---|---|---|---|---|
| | | Strong | Weak | None |
| Intact islets | 10 | 0 | 0 | 6 |
| Early | 12 | 12 | 0 | 0 |
| Intermediate/Late | 18 | 0 | 7 | 11 |

The insulitis lesion was arbitrarily classified as early, intermediate, and late-stage insulitis according to the morphological criteria as follows. Early insulitis was defined as an accumulation of mononuclear cells at the periphery of or just within the islet. In intermediate insulitis, the mononuclear cells infiltrated the center of the islets but left the architecture of the islets relatively well-preserved. In late insulitis, the architecture of islets was distorted, and infiltration by mononuclear cells was markedly increased. The expression of the 4-1BB protein was scored as strong, weak or none. The strong expression indicates that more than 50% of the infiltrating mononuclear cells were positive (FIG. 45B), while weak expression means only a few cells were positive (FIG. 45D).

Discussion

The 4-1BB cDNA was isolated based upon its preferential expression in T-cells. The present study demonstrates that 4-1BB is expressed constitutively in renal medullar cells and that expression is induced in the spleen and heart by PMA treatment. In the spleen, T-cells are likely to respond to PMA or concanavalin A and are probably responsible for the increase of 4-1BB mRNA. However, it is not known which cells in the heart respond to PMA to produce 4-1BB mRNA.

The earlier studies showed that the protein backbone of the natural 4-1 BBP is composed of 233 amino acids with an Mr of 25 kD. This protein therefore must undergo an extensive post-translational modification to be 40 kD protein. The deduced 4-1BBP contains both N- and O-glycosylation sites. Occasionally anti-4-1BB-0 serum recognizes 38 and 34 kD extra bands, which are believed to represent 4-1BBP with different degrees of glycosylation. The protein backbone of truncated 4-1BB is composed of 162 amino acids with an Mr of 18 kD. Since the truncated form produced by COS-1 cells resolves at 23 kD, this form of 4-1BB also undergoes post-translational modification. In fact, when the 4-1BBPs were produced in baculoviral expression system 4-1BBPs constituted three bands of 18 kD, 20 kD and 23 kD which, are believed to represent 4-1BBPs with different degrees of glycosylation (unpublished observation).

The primary structure of 4-1BB, the flow cytometric analysis of 4-1BBP expression, and the secretion of 4-1BBPs indicate that the 4-1BBP is associated with the cellular membrane. Why a certain population of CTLL-R8 cells expressed 4-1BB constitutively is not known. Perhaps a group of cells has changed its properties during the long in vitro maintenance. CTLL-R8 was a cloned CTL which lost killing activity in the course of in vitro maintenance.

To determine the functions of this receptor-like molecule, one may have to find the ligands. The truncated, thus secretory and soluble, 4-1BBPs may have value in determining the function of 4-1BB. If the 4-1BBPs compete for the membrane form of 4-1BB with the specific ligand, the 4-1BBPs may function as a specific inhibitor.

We believe that the infiltrating mononuclear cells which are stained by anti-4-1BB-0 antibodies are activated T-lymphocytes because only splenocytes stimulated with Con A or anti-TCR antibody expressed 4-1BB mRNA. Detailed studies on the surface markers of infiltrating cells that are stained by anti-4-1BB-0 antibodies are underway. It is interesting that 4-1BBP is expressed in the early phase of insulitis and disappears when T-cells infiltrate into islets. The 4-1BBP may be a receptor which transduces signals from the membrane to the nucleus necessary for the immediate early phase of inflammation or antigen recognition. This is in contrast to the expression of other molecules such as perforin (104). Perforin, a potential molecule for tissue damage (105), is produced when T-cells infiltrate the islets. The expression of perforin in the early stage of insulitis was almost undetectable (unpublished observations).

The dynamic functions of T cells in a successful immune system are accomplished through mediators which are produced when T cells are activated. These mediators are in the form of cell surface receptors and soluble secretory molecules. Identification of new mediators and the demonstration of their functions can lead to the discovery of unknown functions of T cells and to the development of ways to manipulate the immune system in the treatment of disease. Expression of a Novel T-cell Molecule, 4-1BB, in the Brain The responses of both the immune and nervous systems to environmental change are mediated by soluble secretory proteins and receptors. Although, to date few biological molecules which are shared by these systems have been identified, the linking of the immune and nervous systems has been the focus of much speculation and had stimulated widespread interest.

A series of T-cell subset-specific cDNAs were cloned from cloned helper and cytolytic T-lymphocytes by employing a modified differential screening procedure. The transcript of one of the clones, 4-1BB, was detected in the T-lymphocytes when the T-cells were activated by either an antigen receptor stimulation or concanavalin A (Con A). This induced expression was inhibited by cyclosporin A. The predicted 4-1BBP contained an unusually large number of cysteines. These residues were arranged with a spacing similar to those in several groups of proteins including the epidermal growth factor receptor. The potential 4-1BB sequence showed similarities with the sequences of the tumor necrosis factor receptor and the nerve growth factor receptor (106). The receptor feature of 4-1BB and the resemblance to the nerve growth factor receptor prompted us this investigation with the brain. Using Northern blot analysis of mRNA and immunocytochemistry for detecting 4-1BB protein (4-1BBP), and it was unexpectedly found that the 4-1BB protein has a high and constitutive expression in the brain, an organ which contains abundant receptor elements and is ontogenically separate from the immune system. The following report deals with the expression of 4-1BB in the nervous system and focuses on its distribution in the brain and in the peripheral nerves.

Method and Materials

Northern Blot Analysis

Mouse organs were sliced into pieces of 1 mm thickness, and a portion of each organ was incubated in PMA (Phorbol Myristic Acetate, 20 ng/ml) containing Dulbecco's minimum essential medium (DMEN, GIBCO) and 10% fetal bovine serum (FBS) for 24 hrs. A portion of spleen was treated with ConA (10 μg/ml) in DMEM and 10% FBS. The remaining portion of each organ was incubated in DMEM and 10% FBS without PMA or ConA for 24 hrs. The tissues were frozen at −70° C. and pulverized in liquid nitrogen before extracting RNA. RNA was extracted from the tissues and cells by guanidinium-phenol extraction procedure (86). The RNA was fractionated on a 1.4% formaldehyde denaturing agarose gel, transferred to a GeneScreen Plus membrane, and hybridized to a $^{32}$P-labeled 4-1BB cDNA probe.

Antibody Preparation

An oligopeptide representing amino acids 105–115 of the deduced 4-1BBP sequence was synthesized (Applied Biosystem). The sequence was NH$_2$-CRPGQELTKSGY-COOH. A tyrosine residue at the C-terminus of the peptide was added for possible radioactive labeling with [$^{125}$I]. The peptide was conjugated to keyhole limpet hemocyanin (KLH) with a heterobifinctional cross linker, m-maleimidobenzoyl-n-hydroxysuccinimide ester (107).

Rabbits were immunized with peptide-KLH (100 μg/dose) emulsified in Freund's complete adjuvant. In two week intervals they received on intracutaneous injection in each of four foot pads and one intramuscular injection. After two weeks, the rabbits received three consecutive I.V. injections without adjuvant. The serum was obtained five days after the final injection and the titer was measured by ELISA using peptide as the antigen. The specificity of these antibodies to 4-1BBP (anti 4-1BB-O) was shown in previous studies.

Immunocyochemistry

The procedure for immunocytochemistry was published previously (108). In brief, C57B1/6 mice were perfused with formaldehyde made fresh intracardially under deep anesthesia from 4% paraformaldehyde and 0.1 M phosphate-buffered saline (PBS). Brains and muscle from the gluteal region were then removed, left in the same fixative overnight, and sliced into 40 um sections for immunocytochemical staining. The 4-1BB (1:200) antiserum was used for positive staining, and antiserum preabsorbed with 4-1BB (10 μg/ml) was used as control. The Stemberger's peroxidase-anti-peroxidase (PAP) indirect-enzyme method was used for staining. The PAP reaction was done with 0.003% H$_2$O$_2$ and 0.05% 3'3-diaminobenzidine. The primary and secondary antibodies were diluted with PBS containing 0.2% Triton-X100 and 1% normal sheep serum. The primary antibodies were incubated overnight and the secondary antibodies were incubated for one hour. Rabbit antiserum against purified mouse laminin (E. Y. Labs, San Mateo, Calif.) was used as a control antiserum.

Results

Similarity of 4-1BBP to Other Known Proteins

The 4-1BBP shows a similarity to the nerve growth factor receptor, the tumor necrosis factor receptor, CD40, and the Shope fibroma virus T2 proteins as described by Smith et al. (106). A search was made for the proteins which contain regions similar to those of 4-1BBP and found two other potential proteins which were encoded by seven in absentia (sina) and by DG17. Sina genes are required by the R7 photoreceptor cell of the Drosophila eye for correct R7 cell development (109). The N-terminal cysteine-rich region of the sina protein is extensively similar to the 4-1BBP (FIG. 47) and is also similar to the protein product of the Dictyostelium DG1 7 gene, whose expression is specifically induced during aggregation by cAMP (110).

FIG. 47 shows a comparison of the 4-1BBP amino acid sequence with the amino acid sequence in sina of Drosophila and DG17 of Dictyostelium. The amino acids which are shared are boxed. Numbers represent the positions of the left-most residues relative to the N-terminus. Gaps (−) are introduced to allow for maximal alignment.

This region forms the pattern of $C-X_2-C-X_9-H-X_3C-X-C$; and the cysteines are histidine are conserved in a similar space in 4-1BB, sina, and DG17 proteins. Ten of 24 amino acids between the 4-1BB and sina proteins are identical. Between 4-1BB and DG17 proteins, 11 of 24 amino acids are identical, and 3 of 24 are conservative substitutions. The conserved pattern suggests that these amino acids are functionally important.

4-1BB mRNA Expression

As shown in FIG. 48, 4-1BB RNA was detected in the brain (lanes A and B), and heart (lanes C and D) and the spleen (lanes G, H, and I) while 4-1BB RNA was not detected in the pancreas (lanes E and F). FIG. 48 shows a northern blot analysis of kidney and brain RNA. Total cytoplasmic RNA from brain (A and B), heart (C and D) and spleen (E, F, and G) were fractionated on 1.2% formaldehyde denaturing agarose gel and hybridized to [$^{32}$P]-labeled 4-1BB cDNA probe. Lane A: unstimulated brain RNA; Lane B: PMA-stimulated brain RNA; Lane C: unstimulated heart RNA; Lane D: PMA-stimulated heart RNA; Lane E: unstimulated spleen RNA; Lane F: PMA-stimulated spleen RNA, and Lane G: ConA-stimulated spleen RNA. Positions of 28S and 18S are indicated by 28 and 18, respectively. The arrow I indicated 4-1BB RNA from brain and the arrow II indicated 4-1BB RNA from spleen and heart.

4-1BB RNA was inducible in the heart and the spleen (lanes D and H) by PMA, and by ConA in the spleen (lane I), but was not inducible in the brain. The size of the brain 4-1BB RNA (FIG. 48, Arrow II) is smaller than that of 4-1BB RNA's from other tissues (FIG. 48, Arrow I). In addition, the mRNA level in the brain is lower than that in other tissues. Such a result is surprising since this protein is detected at a high level in the brain. This may indicate that the 4-1BB mRNA has a long half-life and may undergo several rounds of translation.

Immunocytochemistry: a) General Distribution of 4-1BB Immunoreaction in the Brain Brain tissue (FIGS. 49 and 50) exhibited the most intense 4-1BB immunoreactive staining of all tissue examined, including liver, kidney, and muscle. Generally, dark staining products are densely distributed in the gray matter where neuronal soma, dendrite, and fiber terminals reside (FIG. 48). Except the neuronal soma and distinct fiber bundles, most of the gray matter was stained. In the brain region, where only glial cells accumulate, no staining was identified. Thus, definitive localization of 4-1BB-like protein in the brain was strictly limited to the gray matter. No staining was observed in the major fiber bundle such as corpus callosum, cingulum bundle, internal capsule bundle, fimbria-fornix, medial longitudinal fascicularis, or media forebrain bundle.

FIG. 49 shows 4-1BB immunostaining in the cortex (a, b, and d) striatum (a, d, and e) at progressively enlarged magnifications. 4-1BB staining is seen in the majority of gray matter but is absent in neuron and glial cell bodies, white matter, and in fiber bundles (see corpus callosum, CC in a, and internal capsules, IC and d and e). Granular shape of 4-1BB staining (arrows) is seen around the neuronal bodies (stars in c and e) but not around glial bodies within fiber bundles (d and e). The 4-1BB positive granules in the striatum (e) resemble the dopamine terminals.

FIG. 50 shows distinct 4-1BB immunopositive reaction in the cerebellum at three progressively enlarged magnifications (a, b, and c). The 4-1BB positive reaction is most intense in molecular layer (M), lighter on Purkinje layer (P), and forms glomerulus-like patches (arrows) in the granular layer (G). It is generally absent in the cell bodies of Purkinje, granular layer (G). It is generally absent in the cell bodies of Purkinje, granular neurons, and glial cells. It is completely absent in axons in the fiber bundle in the white matter (W). The majority of the 4-1BB stainings are accumulated in the terminal regions, where synapsis occurs. It was negatively stained when the antiserum was preabsorbed with antigen, 4-1BB peptide (d). Scales: a=200 um, b, d=100 um, and c=30 um.

High magnification (100× oil lens) of light microscopic photographs showed that these distinctly stained 4-1BB immunoreactive products are granular in shape with a size of 0.46–0.55 um. These 4-1BB granules seem to reside among neurons and on the surface of neuronal soma (FIG. 49) and perhaps also on the dendrites/proximal axons. The density of the 4-1BB-like granules varies from region to region, and density distribution is often coincident with that of neuronal fiber terminals. The most intense 4-1BB positive staining was seen in the striatum and closely resembles dopamine-fiber terminals in the striatum (FIGS. 49 d, e).

Immuncytochemistry: b) Specific Regions

Unique distribution of 4-1BB-like staining was observed in a number of brain regions. In the cortex, 4-1BB-like granules were packed in the molecular layer and were distributed with sparse accumulation in layers II to VI (FIG. 49 a, b, c). They were relatively homogeneous among layers except in the frontal cortex, where a band of dense immunoreaction was located in layer IV, and in the temporal cortex, where a dense but relatively narrower band was located within the molecular layer (not shown).

The most densely distributed immunoreactive granules were in the striatum (FIG. 49 d) and in the molecular layers of the cortex (FIG. 49 a, b, c), hippocampus, and cerebellum (FIG. 50). In the cerebellum, the staining pattern was unique in that the 4-1BB-like granules were densely packed in the molecular layer, loosely distributed in the Purkinje layer, accumulated as islands in the sea of granules and Golgi cells in the granular layer, and were almost blank in the fiber bundle area (FIG. 50 a, b, c, and d). The 4-1BB-like granules formed islands and did not seem to border cell bodies as seen in other brain regions. The morphology strongly resembled the glomerulus in the cerebellum. The similar island-like accumulation of 4-1BB-like immunoreactive granules also existed in the nucleus of the stria medularis (not shown).

Discussion 4-1BB, although expressed constitutively in the brain, is produced in the T-cells only when T-cells are activated; therefore, the main site of function may be the brain and not T-lymphocytes. Such a common expression of 4-1BBP may provide a clue to the communication pathway between the immune and nervous systems. 4-1BBP contains a putative zinc finger structure of the yeast elF-2B protein (111) and shared a conserved region with the sina and DG17 proteins. The sina protein is localized in the nucleus, suggesting that it has a regulatory function in cells. The 4-1BBP has been detected at the cellular membrane, cytoplasm, and the nuclear membrane (unpublished observation). The fact that the amino acid sequence of 4-1BB contains features like a zinc finger motif, a nuclear protein, and a receptor domain may indicate that 4-1BB can commute from the cell surface to the nucleus. Determining the ligand of 4-1BBP and its functions is, therefore, critical to further defining the functions of 4-1BBP.

The reasons that the size of brain 4-1BB RNA is smaller than that of 4-1BB RNA from other tissues are not known. It is possible that brain expresses in RNA species similar to 4-1BB sequence, not the 4-1BB gene transcripts. The brain molecules detected by anti-4-1BB-O antibodies, therefore, may well be a cross-reacting protein which contains certain antigen epitopes similar to those of 4-1BBP. Nevertheless, the identification of the brain molecule detected by anti-4-1BB-O antibodies would be important because of the unique patterns of expression.

The mRNA expression and abundant immunostaining of 4-1BB-like protein in the brain indicate that 4-1BB is actively expressed and constitutes a significant component of the brain. Such abundant expression is not seen in the muscle or liver. Much of the evidence indicated that 4-1BB can be a receptor or nerve terminal in the brain and peripheral nervous system: a) morphological examination of the immunostain shows that the 4-1BB-like protein is located in the gray matter, particularly in the regions of dendrites, fiber terminals, and around the cell body of the brain, while being almost entirely absent from the white matter where synapses do not occur; b) the granule-shape morphology resembles the fiber terminals of GABA-ergic neurons on the substantial nigra, dopaminergic neurons on striatum, and synapsin, a synaptic membrane specific protein in the brain; c) while generally absent in the neuronal body and completely absent in and around glial cells, the protein was densely accumulated in many terminal regions of the brain; d) variable densities in regions such as cerebellum, striatum, and cortex coincided with dense fiber terminals; e) peculiar rosette patterns in the cerebellum and stria terminalis morphologically resembled the glomerulus, a specific synaptical complex in the cerebellum.

Recently, two neurotrophic factors, brain-derived neurotrophic factor (BDNF) (112), and neurotrophin-3 (NT-3) (113), were identified in addition to the nerve growth factor (NGF). These three factors closely resembled one another with 57 of the 119 residues (48%) are shared by all three proteins. Six cysteines found in these factors were absolutely conserved, and the regions of greatest similarity were mainly clustered around these cysteine residues. IF BDNF and NT-3 utilize their own receptors, the receptor might have similar structural properties to NGF receptor. The structural similarity of 4-1BB to the NGF receptor allowing a suspicion that 4-1BBP actually encodes one of such known or yet unknown neurotrophic factors.

APPENDIX TO REFERENCES INCORPORATED BY REFERENCE

1. Glasebrook, A. and Fitch, F., *J. Exp. Med.*, 151, 876–895 (1980).
2. Lancki, D. W., Lorber, M. I., Loken, M. R. and Fitch, F. W., *J. Exp. Med.*, 157, 921–935 (1983);
   Moldwin, R. L., Lancki, D. W., Herold, K. C. and Fitch, F. W., *J. Exp. Med.*, 163, 1566–1582 (1986).
3. Gillis, S., Ferm, M. M., Ou, W. and Smith, K. A., *J. Immunol.*, 120, 2027–2032 (1978).
4. Chirgwin, J. M., Przybyla, A. E., MacDonald, R. J. and Rutter, W. J., *Biochemisiry*, 18, 5294–5299 (1979).

5. Aviv, H. and Leder, R., *Proc. Natl. Acad. Sci USA,* 69, 1408–1412 (1972).
6. Land, H., Grez, M., Hauser, H., Lindenmaier, W. and Schutz, G., *Nucleic Acids Res.,* 9, 2251–2266 (1981).
7. Huynh, T. V., Young, R. A. and Davis, R. W., *DNA Cloning: A Practical Apprach,* ed., Glover, D. (IRL, Arlington, Va.), Vol 1., pp. 49–78 (1985).
8. Davis, R. W., Botstein, D. and Roth, J. R., *Advanced Bacterial Genetics,* (Cold Spring Harbor Laboratory, Cold Spring Harbor, N.Y.), pp. 106–107 (1980).
9. Maniatis, R., Fritsch, E. F. and Sambrook, J., *Molecular Cloning: A Laboratory Manual* (Cold Spring Harbor Laboratory, Cold Spring Harbor, N.Y.), pp. 382–389 (1982).
10. Lehrach, H., Diamond, D., Wozney, J. M. and Boedtker, H., *Biochemisry,* 16, 4743–4751 (1977).
11. Feinberg, A. P. and Vogelstein, B., *Anal. Biochem.,* 132, 6–13 (1983).
12. Grass-Bellard, M., Oudet, P. and Chambon, P., *Eur. J. Biochem.,* 36, 32–38 (1973).
13. Southern, E., *J. Mol. Biol.,* 98, 503–517 (1975).
14. Farrar, J., Fuller-Farrar, J., Simon, P., Hilfiker, M., Stadler, B. and Farrar, W., *J. Immunol.,* 125, 2555–2558 (1980).
15. Kim, K., Kanellopoulos-Langevin, C., Merwin, R., Sach, D. and Asofsky, R., *J. Immuol.,* 122, 549–554 (1979).
16. Henkart, P., Millards, P., Reynolds, C. and Henkart, M., *J. Exp. Med.,* 160, 75–93 (1984).
17. Kwon, B. S. and Weissman, S. M., *J. Virol.,* 52, 1000–1004 (1984).
18. Henkart, P. A., Millard, P. J., Reynolds, C. W. and Henkart, M. P., *J. Exp. Med. ,* 160, 75–93 (1984).
19. Messing, J., Crea, R. and Seeburg, P., *Nucleic Acids Res.,* 9, 309–322 (1981).
20. Sanger, F., Nicklen, S. and Coulson, A., *Proc. Natl. Acad. Sci. USA,* 74, 5463–5467 (1977).
21. Biggin, M., Gison, T. and Hung, G., *Proc. Natl. Acad. Sci USA,* 80, 3963–3965 (1983).
22. Zurawski, G., Benedik, M., Kamb, B. J., Abrams, J. S., Zurawaki, S. M. and Lee, F. D., *Science,* 232, 772–775 (1986).
23. Kinachi, T., *Nature,* 325, 70–73 (1986).
24. Gershenfeld, H. K. and Weissman, I. L., *Science,* 232, 854–858 (1986).
25. Lobe, C. G., Finlay, B. B., Paranchych, W., Paetkau, V. M. and Bleackley, R. C., *Science,* 232, 858–861 (1986).
26. Kwon, B., Kestler, D., Lee, E., Wakulchik, M. and Young, J., *J. Exp. Med.,* (In press) (1988).
27. Blobel, G. and Dobberstein, B., *J. Cell. Biol.,* 67, 852–862 (1975);
    Steiner, D., Quinn, P., Chan, S., Marsh, J. and Tager, H., *Ann. N.Y. Acad. Sci.,* 34, 1–16 (1980).
28. Shaw, G. and Kamen, R., *Cell,* 46, 659–667 (1986).
29. Obaru, K., Fukuda, M., Maeda, S. and Shimada, K., *J. Biochem.,* 92, 885–894 (1986).
30. Kozak, M., *Nucleic Acids Res.,* 12, 857–872 (1984).
31. Hedrick, S., Nielsen, E., Kavaler, J., Cohen, D. and Davis, M., *Nature,* 308, 153–158 (1984);
    Cohen, D., Steinberg, A., Paul, W. and Davis, M., *Nature,* 314, 37–374 (1985).
32. Prystowsky, M., Ely, J., Beller, D., Eisenber, L., Goldman, J., Goldman, M., Goldwasser, E., Ihle, J., Quintans, J., Remold, M., Vogel, S. and Fitch, F., *J. Immunol.,* 129, 2337–2344 (1982).
33. Morris, P., *Transplantation,* 32, 349 (1981);
    Orosz, C., Fidelus, R., Roopenian, D., Widmer, M., Ferguson, R. and Bach, F., *J. Immunol.,* 129, 1865 (1982);
    Hess, A., Tutschka, P., Pu, Z. and Santos, G., *J. Immunol.,* 128, 360 (1982).
34. Kronke, M., Leonard, W., Depper, J., Arya, S., Wong-Stahl, F., Gallo, R., Waldmann, T. and Greene, W., *Proc, Natl. Acad. Sci USA,* 81, 5214 (1984);
    Elliott, J., Lin, Y., Mizel, R., Bleackley, R., Harnish, D. and Paetkau, V., *Science,* 226, 1439 (1984); and Granelli-Piperno, A., Inaba, K. and Steinman, R., *J. Exp. Med.,* 160, 1792 (1984).
35. Wiskocil, R., Weiss, A., Imboden, J., Kamin-Lewis, R. and Stobo, J., *J. Immunol,* 134, 1599 (1985).
36. Broxmeyer, H. E. and Williams, D. E., The production of myeloid blood cells and their regulation during health and disease; *CRC Crit. Rev. Oncol./Hematol.,* 8, 173 (1988);
    Broxmeyer, H. E., Interacting effects of cytokines on hematopoietic stem and progenitor cells. In Hematopoietic Growth Factors in Clinical Applications, Mertelsmann, R., Herrmann, F., eds, Marcel Dekker, Inc., New York, N.Y., 3 (1990).
37. Broxmeyer, H. E., Sherry, B., Lu, L., Cooper, S., Carow, C., Wolpe, S. D. and Cerami, A., Myelopoietic enhancing effects of murine macrophage inflammatory proteins and human bone marrow granulocyte/macrophage progenitor cells. *J. Exp. Med,* 170, 1583 (1989);
    Broxmeyer, H. E., Sherry, B., Lu, L., Cooper, S., Oh, K. O., Tekamp-Olson, P., Kwon, B. S. and Cerami, A., Enhancing and suppressing effects of recombinant murine macrophage inflammatory proteins on colony formation in vitro by bone marrow myeloid progenitor cells. *Blood,* 26, 1110 (1990);
    Graham, G. J., Wright, E. G., Hewick, R., Wolpe, S. D., Wilke, N. M., Donaldson, D., Lorimore, S. and Pragnell, I. B., Identification and characterization of an inhibitor of hematopoietic stem cell proliferation. *Nature,* 344, 442 (1990).
38. Wolpe, S. D., Davatelis, G., Sherry, B., Beutler, B., Hesse, D. G., Hguyen, H. T., Moldawer, T. L., Nathan, C. F., Lowry, S. F. and Cerami, A., Macrophages secrete a novel heparin-binding protein with inflammatory and neutrophil chemokinetic properties. *J. Exp. Med.,* 167, 570 (1988);
    Davatelis, G., Tekamp-Olson, P., Wolpe, S. D., Hermsen, K., Luedke Gallegos, C., Cort, D., Merryweather, J. and Cerami, A., Cloning and characterization of a cDNA for murine macrophage inflammatory protein (MIP), a novel monokine with inflammatory and chemokinetic properties. *J. Exp. Med.,* 167, 1939 (1988);
    Sherry, B., Tekamp-Olson, P., Gallegos, C., Bauer, D., Davatelis, G., Wolpe, S. D., Masiarz, F., Cort, D. and Cerami, A., A resolution of the two components of macrophage inflammatory protein 1, and cloning and characterization of one of these components, macrophage inflammatory protein 1 beta. *J. Exp. Med.,* 168, 2251 (1988);
    Wolpe, S. D., Sherry, B., Juers, D., Davatelis, G., Yurt, R. W. and Cerami, A., Identification and characterization of macrophage inflammatory protein 2. *Proc. Natl. Acad. Sci. USA,* 86, 612 (1989);
    Tekamp-Olson, P., Gallegos, C., Bauer, D., McClain, J., Sherry, B., Fabre, M., Van Deventer, S. and Cerami, A., Cloning and characterization of cDNAs for murine macrophage inflammatory protein 2 and its human homologues. *J. Exp. Med.,* 172, 911 (1990).
39. Wolpe, S. D. and Cerami, A., Macrophage inflammatory proteins 1 and 2: members of a novel superfamily of cytokines. *FASEB J.,* 3, 2565 (1989).

40. Oppenheim, J. J., Zachariae, C. O. C., Mukaido, N. and Matsushima, K., Properties of the novel proinflammatory supergene "intercrine" cytokine family. *Ann. Rev. Immunol.*, 9, 617 (1991).
41. Curtis, B. M., Williams, D. E., Broxmeyer, H. E., Dunn, J., Farrah, T., Jeffrey, E., Clevenger, W., de Roos, P., Martin, U., Friend, D., Craig, V., Gayle, R., Price, V., Cosman, D., March, C. J. and Park, L. S., Enhanced hematopoietic activity of a human GM-CSF/IL-3 fusion protein. *Proc. Natl. Acad. Sci. USA*, in press (1991).
42. Williams, D. E., Eisenman, J., Baird, A., Rauch, C., Van Ness, K., March, C. J., Park, L. S., Martin, U., Mochizuki, D. Y., Boswell, H. S., Burgess, G. S., Cosman, D. and Lyman, S. D., Identification of a ligand for the c-kit proto-oncogene. *Cell*, 63, 167 (1990);

Anderson, D. M., Lyman, S. D., Baird, A., Wignall, J. M., Eisenman, J., Rauch, C., March, C. J., Boswell, H. S., Gimpel, S. D., Cosman, D., and Williams, D. E., Molecular cloning of a mast cell growth factor, a hematopoietin that is active in both membrane bound and soluble forms. *Cell*, 63, 235 (1990);

Broxmeyer, H. E., Hangoc, G., Cooper, S., Anderson, D., Cosman, D., Lyman, S. D., and Williams, D. E., Influence of murine mast cell growth factor (Skit ligand) on colony formation by mouse marrow hematopoietic progenitor cells. *Exp. Hematol*, 19, 143 (1991);

Broxmeyer, H. E., Cooper, S., Lu, L., Hangoc, G., Anderson, D., Cosman, D., Lyman, S. D., and Williams, D. E., Effect of murine mast cell growth factor (c-kit proto-oncogene ligand) on colony formation by human marrow hematopoietic progenitor cells. *Blood*, 77, 2142 (1991).

43. Zsebo, K. M., Wypych, J., McNiece, I. K., Lu, H. S., Smith, K. A., Karkare, S. B., Sachdev, R. K., Yus_enkoff, V. N., Birkett, N. C., Williams, L. R., Satyagal, V. N., Tung, W., Bosselman, R. A., Mendiaz, E. A., and Langley, K. E., Identification, purification, and biological characterization of hematopoietic stem cell factor from buffalo rat liver-conditioned medium. *Cell*, 63, 195 (1990);

Martin, F. H., Suggs, S. V., Langley, K. E., Lu, H. S., Ting, J., Okino, K. H., Morris, C. F., McNiece, I. K., Jacobsen, F. W., Mendiaz, E. A., Birkett, N. C., Smith, K. A., Johnson, M. J., Parker, V. P., Flores, J. C., Patel, A. C., Fisher, E. F., Erjavec, H. O., Herrera, C. J., Wypych, J., Sachdev, R. K., Pope, J. A., Leslie, I., Wen, D., Lin, C.-H., Cupples, R. L., and Zsebo, K. M., Primary structure and functional expression of rat and human stem cell factor DNAs. *Cell*, 63, 203 (1990).

44. Nocka, K., Buck, J., Levi, E., and Besmer, P., Candidate ligand for the c-kit transmembrane kinase receptor: KL, a fibroblast derived growth factor stimulated mast cells and erythroid progenitors. *EMBO J*, 9, 3287 (1990);

Huang, E., Nocka, K., Beier, D. R., Chu, T. Y., Buck, J., Lahm, H. W., Wellner, D., Leder, P., and Besmer, P., The hematopoietic growth factor KL is encoded by the SL locus and is the ligand of the ckt receptor, the gene product of the W locus. *Cell*, 63, 225 (1990).

45. Broxmeyer, H. E., Bognacki, J., Dorner, M. H., and deSousa, M., The identification of leukemia-associated inhibitory activity (LIA) as acidic isoferritins: A regulatory role for acidic isoferritins in the production of granulocytes and macrophages. *J. Exp. Med.*, 153, 1426 (1981);

Pelus, L. M., Association between colony forming units' granulocyte-macrophage expression of Ia-like (HLA-DR) antigen and control of granulocyte and macrophage production. A new role for prostaglandin E. *J. Clin. Invest.*, 70, 568 (1982);

Broxmeyer, H. E., Lu, L., Bicknell, D. C., Williams, D. E., Cooper, S., Levi, S., Salfield, J., and Arosio, P., The influence of purified recombinant human acidic and basic isoferritins on colony formation in vitro by granulocyte-macrophage and erythroid progenitor cells. *Blood*, 68, 1257 (1986);

Moore, R. N., Joshi, J. G., Deanna D. G., Pitruzello, F. J., Horohov, D. W., and Rouse, B. T., Characterization of a two-signal-dependent, $Ia^+$ mononuclear phagocyte progenitor subpopulation that is responsive to inhibition by ferritin. *J. Immunol*, 136, 1605 (1986).

46. Williams, D. E., Cooper, S., and Broxmeyer, H. E., The effects of hematopoietic suppressor molecules on the in Airs proliferation of purified murine granulocyte-macrophage progenitor cells (CFU-GM) *Cancer Res.*, 4, 1548 (1988).

47. Broxmeyer, H. E., Cooper, S., Levi, S., and Arioso, P., Mutated recombinant human heavy-chain ferritins and myelosuppressive in vitro and in vixo: A link between ferritin feroxidase activity and biological function. *Proc. Natl. Acad. Sci. USA*, 88, 770 (1991).

48. Broxmeyer, H. E., Suppressor molecules and regulation of myelopoiesis: biology and possible clinical uses. *Amer. J. Ped, Hematol/Oncol.*, in press (1991).

49. Kwon, B. S. and Weissman, S. M., cDNA sequence of two inducible T-cell genes. *Proc. Natl. Acad. Sci. USA*, 86, 1963 (1989);

Kwon, B. S., Kestler, D. P., Eshbar, Z., Oh, K. O., and Wakulchik, M., Expression characterizatics of two potential T-cell mediator genes. *Cell. Immunol.*, 121, 414 (1989).

50. Broxmeyer, H. E., Cooper, S., Lu, L., Miller, M. E., Langefeld, C. D., and Ralph, P., Enhanced stimulation of human bone marrow macrophage colony formation in vitro by recombinant human macrophage colony stimulating factor in agarose medium at low oxygen tension. *Blood*, 7, 323 (1990).

51. Kronenberg, M., Siu, G., Hood, L., and Shastri, N., Molecular genetics of the T-cell antigen receptor and T-cell antigen recognition. *Ann. Rev. Immunol.*, 4, 529; Smith, K., Interleukin 2. *Ann. Rev. Immunol.*, 2, 319 (1984).

52. Kwon, B. S., Kim, G. S., Prystowsky, M. B., Lancki, D. W., Sabath, D. E., Pan, J., and Weissman, S. M., Isolation and initial characterization of multiple species of T-lymphocyte subset cDNA clones. *Proc. Natl. Acad. Sci. USA*, 84, 2896 (1987), incorporated by reference and disclosed herein.

53. Kwon, B. S., and Weisman, S. M., cDNA sequences of two inducible T-cell genes. *Proc. Natl. Acad. Sci. USA*, 86, 1963 (1989), incorporated by reference and disclosed herein;

Kwon, B. S., Kestler, D. P., Zelig, E., Oh, K. O., and Wakulchik, M., Expression characteristics of two potential T-cell mediator genes. *Cell. Imunol.*, 121, 414 (1989).

54. Davatelis, G., Tekamp-Olson, P., Wolpe, S. D., Hermsen, K., Luedke, C., Gallegos, C., Coit, D., Merryweather, J., and Cerami, A., Cloning and characterization of a cDNA for murine macrophage inflammatory protein (MIP), a novel monokine with inflammatory and chemokinetic properties. *Journal of Experimental Medicine*, 167, 1939 (1988);

Sherry, B., Tekamp-Olson, P., Gallegos, C., Bauer, D., Davatelis, G., Wolpe, S., Masiarz, F., Coit, D. and Cerami, A., Resolution of the two components of macrophage inflammatory protein 1, and cloning and characterization of one of those components, macrophage inflammatory protein 1β. *Journal of Experimental Medicine,* 168, 2251 (1988).

55. Obaru, K., Fukuda, M., Maeda, S., and Shimada, K., A cDNA clone used to study mRNA induction in human tonsillar lymphocytes by a tumor promoter. *J. Biochem,* 99, 885 (1986);

Lipes, M. A., Napolitano, M., Jeang, K. T., Chang, N. T., and Leonard, W. J., Identification, cloning and characterization of an immune activation gene. *Proc. Natl. Acad. Sci. USA,* 85, 9704 (1990);

Zipfel, P. F., Balke, J., Irving, S. G., Kelly, K., and Siebenlist, U., Mitogenic activation of human T cells induces two closely related genes which share structural similarities with a new family of secreted factors. *J. Immunol.,* 142, 1582 (1989);

Miller, M. D., Hata, S., Malefyt, R. D. W., and Krangel, M. S., A novel polypeptide secreted by activated human T lymphocytes. *J. Immunol.,* 143, 2907 (1989).

56. Oppenheim, J. J., Zachariae, C. O. C., Mukaida, N., and Matsushima, K., Properties of the novel proinflammatory supergene "intercrine" cytokine family. *Annu. Rev. Immunol.,* 2, 617 (1991).

57. Davatelis, G., Wolpe, S. D., Sherry, B., Dayer, J. M., Chicheportiche, R., and Cerarni, A., Macrophage inflammatory protein-1: a prostaglandin-independent endogenous pyrogen. *Science,* 243, 1066 (1989).

58. Young, J. D.-E., Podack, E. R., and Cohn, Z. A., Properties of a purified pore-forming protein (perforin 1) isolated from H-2-restricted cytotoxic T cell granules. *J. Exp. Med.,* 164, 144 (1986).

59. Tsudo, M., Karasuyama, H., Kitamura, F., Tanaka, T., Kubo, S., Yamamura, Y., Tamatani, T., Hatakeyama, M., Taniguchi, T., and Miyasaka, M., The IL-2 receptor β-chain (p70): ligand binding ability of the cDNA-encoding membrane and secreted forms. *J. Immunol.,* 145, 599 (1990).

60. Hager, D. A., and Burgess, R. R., Elution of proteins from sodium dodecyl sulfate-polyacrylamide gels, removal of sodium dodecyl sulfate, and renaturation of enzymatic activity: results with sigma subunit of *Escherichia coli* RNA polymerase, wheat germ DNA topoisomerase, and other enzymes. *Anal, Biochem.,* 109, 76 (1980).

61. Chin, J., Cameron, P. M., Rupp, E., and Schmidt, J. A., Identification of a high-affinity receptor for native human interleukin 1, and interleukin la on normal human lung fibroblasts. *J. Exp. Med.,* 165, 70 (1987);

Chin, J., Rupp, E., Cameron, P. M., MacNaul, K. L., Lotke, P. A., Tocci, M. J., Schmidt, J. A., and Bayne, E. K., Identification of a high-affinity receptor for interleukin Ioa and interleukin 1, on cultured human rheumatoid synovial cells. *J. Clin. Invest.,* 82, 420 (1988).

62. Tsudo, M., Kozak, R. W., Goldman, C. K., and Waldmann, T. A., Demonstration of a non-Tac peptide that binds interleukin 2: a potential participant in a multichain interleukin 2 receptor complex. *Proc. Natl. Acad. Sci. USA,* 83, 9694 (1986).

63. Ortaldo, J. R., Mason, A. T., O'Shea, J. J., Smyth, M. J., Fals, L. A., Kennedy, I. C. S., Longo, D. L., and Ruscetti, F. W., Mechanistic studies of transforming growth factors inhibition of IL-2-dependent activation of CD3-large granular lymphocyte functions. *J. Immunol.,* 146, 3791 (1991).

64. Graham, G. J., Wright, E. G., Hewick, R., Wolpe, S. D., Wilkie, N. M., Donaldson, D., Lorimore, S., and Pragnell, I. B., Identification and characterization of an inhibitor of haemopoietic stem cell proliferation. *Nature,* 344, 442 (1990).

65. Koeffler, H. P., Induction of differentiation of human acute myelogenous leukemia cells: Therapeutic implications. *Blood,* 62, 709–721 (1983).

66. Scolnick, E. M., Weeks, M. O., Shih, T. Y., Ruscetti, S. K., and Dexter, T. M., Markedly elevated levels of an endogenous sare protein in a hematopoietic precursor cell line. *Mol Cell. Biol.,* 1, 66 (1982).

67. Kurtzberg, J., Bigner, S. H., and Hershfield, M. S., Establishment of the Du.528 human lymphohematopoietic stem cell line. *J. Exp. Med.,* 162, 1561 (1985).

68. Schall, T., Biology of the rantes/sis cytokine family. *Cytokine,* 3, 165 (1991).

69. Graham, G. J., Wright, E. G., Hewick, R., Wolpe, S. D., Wilkie, N. M., Donaldson, D., Lorimore, S., Pragnell, I. B., Identification and characterization of an inhibitor of haematopoietic stem cell proliferation. *Nature,* 344, 442 (1990);

Bodine, D. M., Crosier, P. S., Clark, S. C., Effects of hematopoietic growth factors on the survival of primitive stem cells in liquid suspension culture. *Blood,* 78, 91 (1991).

70. Broxmeyer, H. E., Sherry, B., Cooper, S., Ruscetti, F. W., Williams, D. E., Arosio, P., Kwon, B. S., Cerami, A., Macrophage inflammatory protein (MIP)-1β abrogates the capacity of MIP-1α to suppress myeloid progenitor cell growth. *J. Immunol.,* 147, 2586 (1991).

71. Oh, K. O., Zhou, Z., Kim, K.K., Samanta, H., Fraser, M., Kim, Y. J., Broxmeyer, H. E., Kwon, B., Identification of cell surface receptors for murine macrophage inflammatory protein-1α. *J. Imnunol.,* 147, 2978 (1991).

72. Broxmeyer, H. E., Williams, D. E., Cooper, S., Shadduck, R. K., Gillis, S., Waheed, A., Urdal, D. L., Bicknell, D. C., Comparative effect in vivo of recombinant murine interleukin-3, natural murine colony stimulating factor-1, and recombinant murine granulocyte-macrophage colony-stimulating factor on myelopoiesis in mice. *J. Clin. Invest.,* 79, 721 (1987).

73. Gentile, P. S., and Broxmeyer, H. E., Suppression of mouse myelopoiesis by administration of human lactoferrin in vivo and the comparative action of human transferrin. *Blood,* 61, 982 (1983);

Broxmeyer, H. E., Williams, D. E., Hangoc, G., Cooper, S., Gentile, P., Shen, R-N., Ralph, P., Gillis, S., Bicknell, D. C., The opposing actions in yiv on murine myelopoiesis of purified preparations of lactoferrin and the colony stimulating factors. *Blood Cells,* 13, 31 (1987);

Broxmeyer, H. E., Williams, D. E., Geissler, K., Hangoc, G., Cooper, S., Levi, S., Arosio, P., Suppressive effects in vivo of purified recombinant human H-subunit (acidic) ferritin on murine myelopoiesis. *Blood,* 73, 74 (1988).

74. Hangoc, G., Carow, C., Schwall, R., Mason, A. J., Broxmeyer, H. E., Influence of recombinant human inhibin in vivo on myelopoiesis in C3H/HeJ mice. *Blood,* 76, 96a (1990).

75. Goey, H., Keller, J. R., Back, T., Longo, D. L., Russcetti, F. W., Wiltrout, R. H., Inhibition of early_rine hemopoietic progenitor cell proliferation after in vivo locoregional administration of transforming growth factor-β1. *J. Immunol.,* 143, 877 (1989);

Jansen, R., Damia, G., Usui, N., Keller, J., Futami, H., Goey, H., Back, T. T., Longo, D. L., Ruscetti, F. W., Wiltrout, R. H., Effects of recombinant transforming growth factor $\beta_1$ on hematologic recovery after treatment of mice with 5-fluorouracil. *J. Immunol.,* 147, 3342 (1991);

Migdalska, A., Molineux, G., Demuyck, H., Evans, G. S., Ruscetti, F., Dexter, T. M., Growth inhibitory effects of transforming growth factor $\beta_1$ in vivo. *Growth Factors,* 4, 239 (1991).

76. Reviewed in Broxmeyer, H. E., Iron-binding proteins and the regulation of hematopoietic cell proliferation/ differentiation, in *Iron in Immunity, Cancer and Inflammation,* M. deSousa and J. H. Brock, eds, John Wiley and Sons Ltd., London, p. 199 (1989);

Broxmeyer, H. E., Suppressor cytokines and regulation of myelopoiesis. Biology and possible clinical uses. *Amer., J. Ped. Hematol/Oncol.,* 14, 22 (1991);

Ruscetti, F. W., Jacobsen, S. E., Birchenhall-Roberts, M., Broxmeyer, H. E., Engelmann, G. L., Dubois, C., Keller, J. R., Role of transforming growth factor-$\beta$1 in regulation of hematopoiesis. *Ann. N.Y. Acad. Sci.,* 628, 31 (1991);

Keller, J. R., Jacobsen, S. E. W., Dubois, C. M., Hestdal, K., Ruscetti, F. W., Transforming growth factory: a bidirectional regulator of hematopoietic cell growth. *Int. J. Cell Cloning,* 10, 2 (1991).

77. Minano, F. J., Sancibrian, M., Vizcaino, M., Paez, X., Davatelis, G., Fahey, T., Sherry, B., Cerami, A., and Myers, R. D., Macrophage inflammatory protein-1: unique action on the hypothalamus to evoke fever. *Brain Res. Bul.,* 24, 849–852 (1990).

78. Fahey III, T. J., Sherry, B., Tracey, K. J., van Deventer, S., Jones II, W. G., Minei, J. P., Morgello, S., Shires, G. T., and Cerami, A., Cytokine production in a model of wound healing: the appearance of MIP-1, MIP-2, cachectin/TNF and IL-1. *Cytokine,* 2, 92–99 (1990).

79. Graham, G. J., Wright, E. G., Hewick, R., Wolpe, S. D., Wilke, N. M., Donaldson, D., Lorimore, S., and Pragnell, I. B., Identification and characterization of an inhibitor of haematopoietic stem cell proliferation. *Nature,* 344, 442 (1990);

Broxmeyer, H. E., Sherry, B., Cooper, S., Ruscetti, F. W., Williams, D. E., Arosio, P., Kwon, B. S., and Cerami, A., Macrophage inflammatory protein (MIP)-1$\alpha$ abrogates the capacity of MIP-1$\alpha$ to suppress myeloid progenitor cell growth. *J. Immunol.,* 14, 2586–2594 (1991).

80. Oh, K.-O., Zhou, Z., Kim, K.-K., Samanta, H., Fraser, M., Kim, Y.-J., Broxmeyer, H. E., and Kwon, B. S., Identification of cell surface receptors for murine macrophage inflammatory protein-1$\alpha$. *J. Immunol.,* 147, 2978–2983 (1991).

81. Mishell, B. B. and Shiigi, S. M., *Selected methods in cellular immunology.* 182–185. W.H. Freeman and Company, N.Y., incorporated herein by reference;

DeFranco, A. L., Raveche, E. S., Asofsky, R. and Paul, W. E., Frequency of B lymphocytes responsive to anti-immunoglobulin. *J. Exp. Med.,* 155, 1523 (1982).

82. Rizzino, A., and Kazokoff, P., lodination of peptide growth factors: platelet-derived growth factor and fibroblast growth factor. *Meth. Enzy.,* 44, 467 (1991).

83. Mirazawa, K., Mantel, C., Lu, L., Morrison, D. C., and Broxmeyer, H. E., Lactoferrin-lipopolysaccharide interactions effect on lactoferrin binding to monocyte/ macrophage-differentiated HL-60 cells. *J. Immunol.,* 146, 723 (1991).

84. Monté, D., Wietzebin, J., Pancré, V., Merlin, G., Greenberg, S. M., Kusnierz, J. P., Capron, A., and Aurioult, C., Identification and characterization of a functional receptor for interferon-r on a megakaryocytic cell line. *Blood,* 78, 2062 (1991).

85. Chomczynski,__., and Sacchi, N., Single-step method of RNA isolation by acid guanidium thiocyanate-phenol-chloroform extraction. *Anal. Riochem.,* 162, 156 (1987).

86. Kehrl, J. H., Wakefield, L. M., Roberts, A. B., Jakowlew, S., Alvarez-Mon, M., Derynck, R., Sporn, M. B., and Fauci, A. S., Production of transforming growth factor $\beta$ by human T lymphocytes and its potential role in the regulation of T cell growth. *J. Exp. Med.,* 163, 1037 (1986);

Smeland, E. B., Blomhoff, H. K., Holte, H., Ruud, E., Beiske, K., Funderud, S., Godal, T., and Ohlsson, R., Transforming growth factor Type $\beta$ (TGF$\beta$) inhibits $G_1$ to S transition, but not activation of human B lymphocytes. *Exp. Cell. Res.,* 171, 213 (1987).

87. Taga, K., and Tosato, G., IL-10 inhibits human T cell proliferation and IL-2 production. *J. Immunol.,* 148, 1143 (1992).

88. Kwon, B. S., Kim, G. S., Prystowsky, M. B., Lancki, D. W., Sabath, D. E., Pan, J., and Weissman, S. M., Isolation and initial characterization of multiple species of T-lymphocyte subset cDNA clones. *Proc. Natl. Acad. Sci. USA,* 84, 2896–2900 (1989).

89. Kwon, B. S., and Weissman, S. M., cDNA sequences of two inducible T-cell genes. *Proc. Natl. Acad. Sci. USA,* 86, 1963–1967 (1989).

90. Kwon, B. S., Kestler, D. P., Eshhar, Z., Oh, K., and Wakulchik, M., Expression characteristics of two potential T cell mediator genes. *Cell. Immunol.,* 121, 414–422 (1989).

91. Smith, C. A., Davis, T., Anderson, D., Solam, L., Beckmann, M. P., Jerzy, R., Dower, S. K., Cosman, D., and Goodwin, R. G., A receptor for tumor necrosis factor defines an unusual family of cellular and viral proteins. *Science,* 248, 1019–1023 (1990).

92. Mallett, S., and Barclay, A. N., A new superfamily of cell surface proteins related to the nerve growth factor receptor. *Immunology Today,* 12, 220–223 (1991).

93. Shaw, A. S., Chalupny, J., Whitney, J. A., Hammond, C., Amrein, K. E., Kavathas, P., Sefton, B. A., and Rose, J. K., Short related sequences in the cytoplasmic domains of CD4 and CD8 mediate binding to the amino-terminal domain of the $p56^{lck}$ tyrosine protein kinase. *Mol. Cell. Bio.,* 10, 1853–1862 (1990).

94. Makino, S., Kunimoto, K., Muraoka, Y., Mizushima, Y., Katagiri, K., and Tochino, Y., Breeding of a non-obese, diabetic strain of mice. *Exp. Anim .,* 22, 1–13 (1980).

95. Tochino, Y., Kanaya, T., and Makino, S., Genetics of NOD mice. In *Clinico-Genetic Genesis of Diabetes Mellitus.* (Mimura, G., Baba, S., Goto, Y., Kobberling, J., Eds.), Amsterdam, Excerpta Medica, p. 285 (1982);

Foulis, A. K., Liddle, C. N., Farquharson, M. A., Richmond, J. A., and Weir, R. S., The histopathology of the pancreas in type I (insulin-dependent) diabetes mellitus: a 25-year review of deaths in patients under 20 years of age in the United Kingdom. *Diabetologia,* 29, 267–274 (1986);

Gepts, W., Pathologic anatomy of the pancreas in juvenile diabetes mellitus. *Diabetes,* 14, 619–633 (1965).

96. Palladino, M. A., Obata, Y., Stockert, E. R., and Oettgen, H. F., Characterization of interleukin 2-dependent cytotoxic T-cell clones: specificity, cell surface phenotype, and susceptibility to blocking by Lyt antisera. *Cancer Res.,* 43, 572–576 (1983).

97. Liu, F. T., Zinnecker, M., Hamaoka, T., and Katz, D. H., New procedures for preparation and isolation of conjugates of proteins and a synthetic copolymer of D-amino acids and immunochemical characterization of such conjugates. *Biochemisry,* 18, 690–693 (1979).
98. Imh, S. H., Lee, K. U., and Yoon, J. W., Studies on autoimmunity for the initiation of B-cell destruction VII. Evidence for antigenic changes on the B-cell leading to the autoimmune destruction of B-cell in BB rat. (In Press) (1990).
99. Saiki, R. K., Gelfand, D. H., Stfel, S., Scharf, S. J., Higu__hi, R., Horn, G. T., Mullis, K. B., and Erlich, H. A., Primer-directed enzymatic amplification of DNA with a thermostable DNA polymerase. *Science,* 23, 487–491 (1988).
100. Yang, Y., Ciarletta, A. B., Temple, P. A., Chung, M. P., Kovacic, S., Witek-Giannotti, J. S., Leary, A. C., Kriz, R., Donahue, R. E., Wong, G. G., and Clark, S. C., Human IL-3 (multi-CSF): identification by expression cloning of novel hematopoietic growth factor related to murine IL-3. *Cell,* 47, 3–10, (1986).
101. McCutchan, J. H., and Pagano, J. S., Enhancement of the infectivity of simian virus 40 deoxyribonucleic acid with diethylaminoethyl-dextran. *J. Natl. Cancer Inst.,* 41, 351–357 (1968).
102. Chomczynski, P., and Sacchi, N., Single-step method of RNA isolation by acid guanidinium thiocyanate-phenol-chloroform extraction. *Anal. Biochem.,* 162, 156–159 (1987).
103. Kwon, B. S., Wakulchik, M., Liu, C-C, Persechini, P.M., Trapani, J. A., Haq, A. K., Kim, Y., and Young, JD-E., The structure of the mouse lymphocyte pore-forming protein perforin. *Biochem, Biophys. Res. Commun.,* 158, 1–10 (1989).
104. Young, L. H. Y., Peterson, L. B., Wicker, L. S., Persechini, P. M., and Young, JD-E., In vivo expression of perforin by CD8+ lymphocytes in autoimmune disease. Studies on spontaneous and adoptively transferred diabetes in nonobese diabetic mice. *J. Immunol.,* 143, 3994–3999 (1989).
105. Smith, C. A., Davis, T., Anderson, D., Solam, L., Beckmann, M. P., Jerzy, R., Dower, S. K., Cosman, D., and Goodwin, R. G., A receptor for tumor necrosis factor defines an unusual family of cellular and viral proteins. *Science,* 248, 1019–1023 (1990).
106. Liu, F. T., Zinnecker, M., Hamaoka, T., and Katz, D. H., New procedures for preparation and isolation of conjugates of proteins and a synthetic copolymer of D-amino acids and immunochemical characterizations of such conjugates. *Biochemistry,* 18, 690–693 (1979).
107. Zhou, F. C. and Azmitia, E. C., Induced homotypic sprouting of serotonegic fibers in hippocampus: II, An immunocytochemical study. *Brain Res.,* 373, 337–348 (1986);
Zhou, F. C., and Buckwald, N., Connectivities of striatal grafts in the adult rat brain: A rich afference and scant nigro striatal efference. *Brain Res.,* 504, 125–130 (1989);
Zhou, F. C. and Azmitia, E. C., Neurotrophic factor for serotonergic neurons prevents degeneration of grafted raphe neurons in the cerebellum. *Brain Res.,* 507, 301–308 (1990).
108. Carthew, R. W., and Rubin, G. M., seven in absentia. A gene required for specification of R7 cell rate in the Drosophila eye. *Cell,* 63, 561–577 (1990).
109. Driscoll, D. M., and Williams, J. G., Two divergently transcribed genes of Dictyostelium discoideum are cyclic AMP-inducible and coregulated during development. *Mol. and Cell. Biol.,* 7, 4482–4489 (1987).
110. Donahue, T., Cigan, A., Pahich, E., and Valavicius, B., Mutations at a Zn(II) finger motif in the yeast elF-2β gene alter ribosomal start-site selection during the scanning process. *Cell,* 54, 621–632 (1988).
111. Maisonpierre, P. C., Belluscio, L., Squinto, S., Ip, N.Y., Furth, M. E., Lindsay, R. M., and Yancopoulos, G. D., Neurotrophin-e: A neurotrophic factor related to NGF and BDNF. *Science,* 247, 1446–1451 (1990).
112. Leibrock, J., Lottspeich, F., Hohn, A., Hofer, M., Hengrer, B., Masiakowski, P., Thoenen, H., and Barde, Y. A., Molecular cloning and expression of brain-derived neurotrophic factor. *Nature,* 341, 149–152 (1989).

The foregoing description has been directed to particular embodiments of the invention in accordance with the requirements of the Patent Statutes for the purposes of illustration and explanation. It will be apparent, however, to those skilled in this art that many modifications and changes will be possible without departure from the scope and spirit of the invention. It is intended that the following claims be interpreted to embrace all such modifications.

What is claimed is:

1. A cDNA having a nucleotide sequence as shown in FIG. 2a.

2. An isolated and purified cDNA comprising the nucleotide sequence set forth in FIG. 2a.

3. A vector comprising the cDNA of claim 2.

4. An isolated and purified DNA comprising the nucleic acid sequence set forth in FIG. 2a or the complement thereof which is labeled.

* * * * *